Figure 6:
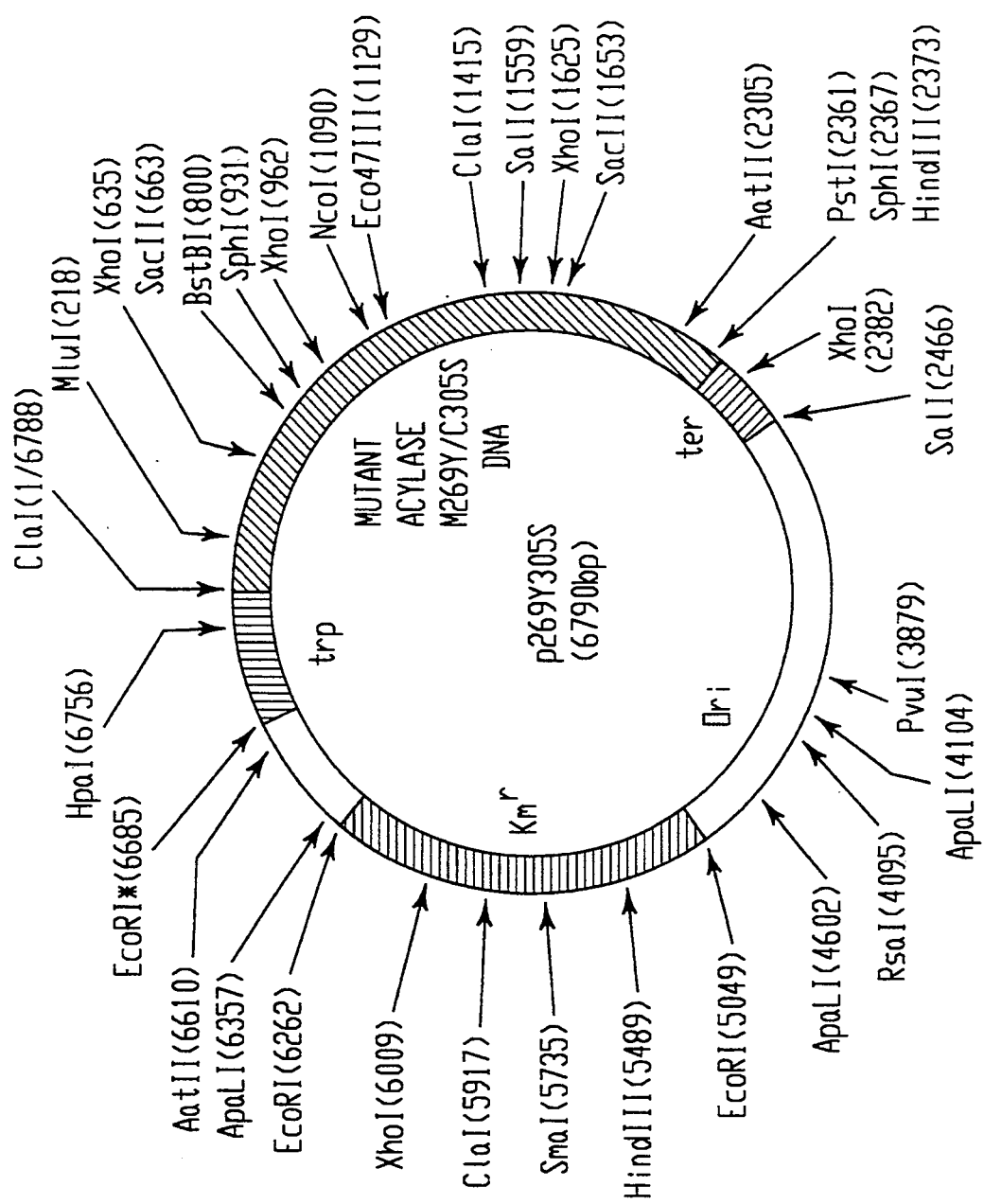

United States Patent [19]

Niwa et al.

[11] Patent Number: 5,336,613
[45] Date of Patent: Aug. 9, 1994

[54] CEPHALOSPORIN C ACYLASE

[75] Inventors: Mineo Niwa, Muko; Yoshimasa Saito, Kawanishi; Hitoshi Sasaki, Tsukuba; Yoshinori Ishii, Kobe, all of Japan

[73] Assignee: Fujisawa Pharmaceutical Co., Ltd., Osaka, Japan

[21] Appl. No.: 19,870

[22] Filed: Feb. 19, 1993

[30] Foreign Application Priority Data

Feb. 27, 1992 [GB] United Kingdom ............... 9204439

[51] Int. Cl.$^5$ .................. C12N 9/80; C12N 15/52
[52] U.S. Cl. ..................... 435/228; 435/69.1; 435/49; 435/51; 435/172.3; 435/252.3; 435/320.1; 536/23.2; 935/14
[58] Field of Search ............... 435/228, 49, 51, 172.3, 435/69.1, 252.3, 320.1, 14; 536/23.2

[56] References Cited

U.S. PATENT DOCUMENTS

| | | | |
|---|---|---|---|
| 4,752,585 | 6/1988 | Koths et al. | 435/256 |
| 4,835,260 | 5/1989 | Shoemaker | 530/397 |
| 4,959,314 | 9/1990 | Mark et al. | 435/69.1 |
| 5,192,678 | 3/1993 | Iwami et al. | 435/228 |

FOREIGN PATENT DOCUMENTS 61-152286 7/1986 Japan .

OTHER PUBLICATIONS

Bowie et al. (1990) Science 247, 1306–1310.
Ichiro Aramori et al, "Cloning and Nucleotide Sequencing of New Glutaryl 7–ACA and Cephalosporin C Acylase Genes from Pseudomonas Strains," Journal of Fermentation and Bioengineering, vol. 72, No. 4, (1991), pp. 232–243.
Ichiro Aramori et al, "Isolation of Soil Strains Producing New Cephalosporin Acylases," Journal of Fermentation and Bioengineering, vol. 72, No. 4, (1991), pp. 227–231.

Primary Examiner—Keith Baker
Attorney, Agent, or Firm—Oblon, Spivak, McClelland, Maier & Neustadt

[57] ABSTRACT

The present invention concerns a mutant cephalosporin C acylase derived from a precursor of the formula:

$$A^{1-268} - X^1 - Tyr - X^2 - A^{272-304} - X^3 - A^{306-773}$$

(SEQ ID NO:1), wherein:

$A^{1-268}$ is the same amino acid sequence as that from Thr$^1$ to Gly$^{268}$ of native CC acylase, $A^{272-304}$ is the same amino acid sequence as that from Gln$^{272}$ to Tyr$^{304}$ of native CC acylase, $A^{306-773}$ is the same amino acid sequence as that from Val$^{306}$ to Ala$^{773}$ of native CC acylase, $X^1$ is Met or other amino acid, $X^2$ is Ala or Tyr, and $X^3$ is Cys or Ser, provided that when $X^1$ is Met and $X^2$ is Ala, $X^3$ is Ser; and that the mutant cephalosporin C acylase has a property selected from the group consisting of higher enzymatic potency and higher processing efficiency, as compared to native CC acylase. The present invention also concerns DNA encoding the mutant cephalosporin C acylase, an expression vector containing the DNA, a host cell transformed with the expression vector, a process for producing the mutant cephalosporin C acylase by culturing the transformed host cell, and a process for preparing a cephalosporin C using the mutant cephalosporin C acylase.

11 Claims, 54 Drawing Sheets

```
ATG ACT ATG GCA GCT AAT ACG GAT CGC GCG GTC TTG CAG GCG GCG CTG      48
Met Thr Met Ala Ala Asn Thr Asp Arg Ala Val Leu Gln Ala Ala Leu
 -1           1                   5                  10          15

CCG CCG CTT TCC GGC AGC CTC CCC ATT CCC GGA TTG AGC GCG TCG GTC      96
Pro Pro Leu Ser Gly Ser Leu Pro Ile Pro Gly Leu Ser Ala Ser Val
             20                  25                  30

CGC GTC CGG CGC GAT GCC TGG GGC ATC CCG CAT ATC AAG GCC TCG GGC     144
Arg Val Arg Arg Asp Ala Trp Gly Ile Pro His Ile Lys Ala Ser Gly
         35                  40                  45

GAG GCC GAT GCC TAT CGG GCG CTG GGC TTC GTC CAT TCG CAG GAC CGT     192
Glu Ala Asp Ala Tyr Arg Ala Leu Gly Phe Val His Ser Gln Asp Arg
 50                  55                  60

CTT TTC CAG ATG GAG CTG ACG CGT CGC AAG GCG CTG GGA CGC GCC GCC     240
Leu Phe Gln Met Glu Leu Thr Arg Arg Lys Ala Leu Gly Arg Ala Ala
 65                  70                  75

GAA TGG CTG GGC GCC GAG GCC GAT ATC CTC GTG CGC CGG                 288
Glu Trp Leu Gly Ala Glu Ala Asp Ile Leu Val Arg Arg
 80                  85                  90          95
```

*FIG. 1A*

```
CTC GGA ATG GAA AAA GTC TGC CGG CGC GAC TTC GAG GCC TTG GGC GTC          336
Leu Gly Met Glu Lys Val Cys Arg Arg Asp Phe Glu Ala Leu Gly Val
             100                 105                 110

GAG GCG AAG GAC ATG CTG CGG GCT TAT GTC GCC GGC GTG AAC GCA TTC          384
Glu Ala Lys Asp Met Leu Arg Ala Tyr Val Ala Gly Val Asn Ala Phe
                 115                 120                 125

CTG GCT TCC GGT GCT CCC CTG CCT GAA TAC GGA TTG CTC GAA GGA GCA          432
Leu Ala Ser Gly Ala Pro Leu Pro Glu Tyr Gly Leu Leu Glu Gly Ala
             130                 135                 140

GAG CCG GAG CCC TGG GAG CCT TGG CAC AGC ATC GCG GTG ATG CGC CGG          480
Glu Pro Glu Pro Trp Glu Pro Trp His Ser Ile Ala Val Met Arg Arg
             145                 150                 155

CTG GGC CTG CTT ATG GGT TCG GTG TGG TTC AAG CTC TGG CGG ATG CTG          528
Leu Gly Leu Leu Met Gly Ser Val Trp Phe Lys Leu Trp Arg Met Leu
             160                 165                 170             175

GCG CTG CCG GTG GTC GGA GCC GCG AAT GCC GGA GCA CTG AAG CTG CGC TAT GAC  576
Ala Leu Pro Val Val Gly Ala Ala Asn Ala Gly Ala Leu Lys Leu Arg Tyr Asp
                 180                 185                 190
```

*FIG. 1B*

| | | | | | | | | | | | | | | | |
|---|---|---|---|---|---|---|---|---|---|---|---|---|---|---|---|
| GAT | GGC | CGG | GAT | TTG | CTC | TGC | ATC | CCG | GGC | GCC | GAA | GCC | GAT | | 624 |
| Asp | Gly | Arg | Asp | Leu | Leu | Cys | Ile | Pro | Gly | Ala | Glu | Ala | Asp | | |
| | | 195 | | | | | 200 | | | | 205 | | | | |
| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | 210 | | | | | 215 | | | | | 220 | | | | | |
| CTG | AAG | GCG | ATG | GGC | GGC | GAT | GCC | TCC | GAT | GCT | GCT | GCC | GGC | GGC | AGC | 720 |
| Leu | Lys | Ala | Met | Gly | Gly | Asp | Ala | Ser | Asp | Ala | Ala | Ala | Gly | Gly | Ser | |
| 225 | | | | | 230 | | | | | 235 | | | | | | |
| AAC | AAC | TGG | GCG | GTC | GCT | CCG | GGC | CGC | ACG | GCG | ACC | GGC | AGG | CCG | ATC | 768 |
| Asn | Asn | Trp | Ala | Val | Ala | Pro | Gly | Arg | Thr | Ala | Thr | Gly | Arg | Pro | Ile | |
| | 240 | | | | 245 | | | | | 250 | | | | | 255 | |
| CTC | GCG | GAT | CCG | CAT | CGC | GTC | TTC | GAA | ATC | CCG | GGC | ATG | TAT | GCG | | 816 |
| Leu | Ala | Gly | Asp | Pro | His | Arg | Val | Phe | Glu | Ile | Pro | Gly | Met | Try | Ala | |
| | | | 260 | | | | | 265 | | | | | 270 | | | |
| CAG | CAT | CAT | CTG | GCC | TGC | GAC | CGG | TTC | GAC | ATG | ATC | GGC | CTG | ACC | GTG | 864 |
| Gln | His | His | Leu | Ala | Cys | Asp | Arg | Phe | Asp | Met | Ile | Gly | Leu | Thr | Val | |
| | | 275 | | | | | 280 | | | | 285 | | | | | |

*FIG. 1C*

```
CCG GGC GTG CCG GGC TTC CCG CAC TTC GCG AAC GGC AAG GTC GCC       912
Pro Gly Val Pro Gly Phe Pro His Phe Ala Asn Gly Lys Val Ala
     290              295              300

TAT AGC GTC ACG CAT GCC TTC ATG GAC ATC CAC GAT CTC TAT CTC GAG   960
Tyr Ser Val Thr His Ala Phe Met Asp Ile His Asp Leu Tyr Leu Glu
     305              310              315

CAG TTC GCG GGG GAG GGC CGC ACT GCG CGG TTC GGC AAC GAT TTC GAG  1008
Gln Phe Ala Gly Glu Gly Arg Thr Ala Arg Phe Gly Asn Asp Phe Glu
     320              325              330              335

CCC GTC GCC TGG AGC CGG GAC CGT ATC GCC GTC CGG GGT GGC GCC GAT  1056
Pro Val Ala Trp Ser Arg Asp Arg Ile Ala Val Arg Gly Gly Ala Asp
     340              345              350

CGC GAG TTC GAT ATC GTC GAG ACG CGC CAT GGC CCG GTT ATC GCG GGC  1104
Arg Glu Phe Asp Ile Val Glu Thr Arg His Gly Pro Val Ile Ala Gly
     355              360              365

GAT CCG CGC GAT GGC GCA GCG CTC ACG CTG CGT TCG GTC CAG TTC GCC  1152
Asp Pro Arg Asp Gly Ala Ala Leu Thr Leu Arg Ser Val Gln Phe Ala
370              375              380
```

*FIG. 1D*

```
GAG  ACC  GAT  CTG  TCC  TTC  GAC  TGC  CTG  ACG  CGG  ATG  CCG  GGC  GCA  TCG   1200
Glu  Thr  Asp  Leu  Ser  Phe  Asp  Cys  Leu  Thr  Arg  Met  Pro  Gly  Ala  Ser
385                           390                      395

ACC  GTG  GCC  CAG  CTC  TAC  GAC  GCG  ACG  CGC  TGG  GGC  CTG  ATC  GAC         1248
Thr  Val  Ala  Gln  Leu  Tyr  Asp  Ala  Thr  Arg  Trp  Gly  Leu  Ile  Asp
400                           405                      410                 415

CAT  AAC  CTC  GTC  GCC  GGG  GAT  GTC  GCG  GGC  TCG  ATC  GGC  CAT  CTG  GTC   1296
His  Asn  Leu  Val  Ala  Gly  Asp  Val  Ala  Gly  Ser  Ile  Gly  His  Leu  Val
                    420                           425                      430

CGC  GCC  CGC  GTT  CCG  TCC  CGT  CCG  CGC  GAA  AAC  GGC  TGG  CTG  CCG  GTG   1344
Arg  Ala  Arg  Val  Pro  Ser  Arg  Pro  Arg  Glu  Asn  Gly  Trp  Leu  Pro  Val
               435                           440                      445

CCG  GGC  TGG  TCC  GGC  GAG  CAT  GAA  TGG  CGG  GGC  TGG  ATT  CCG  CAC  GAG   1392
Pro  Gly  Trp  Ser  Gly  Glu  His  Glu  Trp  Arg  Gly  Trp  Ile  Pro  His  Glu
          450                           455                      460

GCG  ATG  CCG  CGC  GTG  ATC  GAT  CCG  CCG  GGC  ATC  GTC  ACG  GCG              1440
Ala  Met  Pro  Arg  Val  Ile  Asp  Pro  Pro  Gly  Ile  Val  Thr  Ala
465                           470                      475
```

*FIG. 1E*

```
AAT AAT CGC GTC GTG GCC GAT GAC CAT CCC GAT TAT CTC TGC ACC GAT    1488
Asn Asn Arg Val Val Ala Asp Asp His Pro Asp Tyr Leu Cys Thr Asp
480             485                 490                 495

TGC CAT CCG CCC TAC CGC GCC GAG CGC ATC ATG AAG CGC CTG GTC GCC    1536
Cys His Pro Pro Tyr Arg Ala Glu Arg Ile Met Lys Arg Leu Val Ala
        500                 505                 510

AAT CCG GCT TTC GCC GTC GAC GAT GCC GCC ATC CAT GCC GAT ACG        1584
Asn Pro Ala Phe Ala Val Asp Asp Ala Ala Ile His Ala Asp Thr
    515                 520                 525

CTG TCG CCC CAT GTC GGG TTG CTG CGC CGG AGG CTC GAG GCG CTT GGA    1632
Leu Ser Pro His Val Gly Leu Leu Arg Arg Arg Leu Glu Ala Leu Gly
        530                 535                 540

GCC CGC GAC GAC TCC GCG GCC GAA GGG CTG AGG CAG ATG CTC GTC GCC    1680
Ala Arg Asp Asp Ser Ala Ala Glu Gly Leu Arg Gln Met Leu Val Ala
    545                 550                 555

TGG GAC GGC CGC ATG GAT GCT TCG GAG GTC GCC TCT GCC TAC AAT        1728
Trp Asp Gly Arg Met Asp Ala Ser Glu Val Ala Ser Ala Tyr Asn
560             565                 570                 575
```

*FIG. 1F*

```
GCG TTC CGC AGG GCG CTG ACG CGG CTG GTG ACG GAC CGC AGC GGG CTG    1776
Ala Phe Arg Arg Ala Leu Thr Arg Leu Val Thr Asp Arg Ser Gly Leu
            580                 585                 590

GAG CAG GCG ATA TCG CAT CCC TTC GCG GCT GTC GCC GGC GTC TCA       1824
Glu Gln Ala Ile Ser His Pro Phe Ala Ala Val Ala Pro Gly Val Ser
            595                 600                 605

CCG CAA GGC CAG GTC TGG TGG GCC GTG CCG ACC CTG CGC GAC GAC       1872
Pro Gln Gly Gln Val Trp Trp Ala Val Pro Thr Leu Arg Asp Asp
            610                 615                 620

GAT GCC GGA ATG CTG AAG GGC TGG AGC TGG GAC CAG GCC TTG TCT GAG   1920
Asp Ala Gly Met Leu Lys Gly Trp Ser Trp Asp Gln Ala Leu Ser Glu
            625                 630                 635

GCC CTC TCG GTC GCG TCG CAG AAC CTG ACC GGG CGA AGC TGG GGC GAA   1968
Ala Leu Ser Val Ala Ser Gln Asn Leu Thr Gly Arg Ser Trp Gly Glu
            640                 645                 650                 655

GAG CAT CGG CCG CGC TTC ACG CAT CCG CTT GCC ACC CAA TTC CCG GCC   2016
Glu His Arg Pro Arg Phe Thr His Pro Leu Ala Thr Gln Phe Pro Ala
            660                 665                 670
```

*FIG. 1G*

```
TGG GCG GGG CTG CTG AAT CCG GCT TCC CGT CCG ATC GGT GGC GAT GGC       2064
Trp Ala Gly Leu Leu Asn Pro Ala Ser Arg Pro Ile Gly Gly Asp Gly
        675                 680                 685

GAT ACC GTG CTG GCA AAC GGG CTC GTC CCG TCA GCC GGG CCG CAG GCG       2112
Asp Thr Val Leu Ala Asn Gly Leu Val Pro Ser Ala Gly Pro Gln Ala
        690                 695                 700

ACC TAT GGT GCC CTG TCG CGC TAC GTC TTC GAT GTC GGC AAT TGG GAC       2160
Thr Tyr Gly Ala Leu Ser Arg Tyr Val Phe Asp Val Gly Asn Trp Asp
  705                 710                 715

AAT AGC CGC TGG GTC GTC GTC TTC CAC GGC TCC GGG CAT CCG GCC AGC       2208
Asn Ser Arg Trp Val Val Val Phe His Gly Ser Gly His Pro Ala Ser
  720                 725                 730                 735

GCC CAT TAT GCC GAT CAG AAT GCG CCC TGG AGC GAC TGT GCG ATG GTG       2256
Ala His Tyr Ala Asp Gln Asn Ala Pro Trp Ser Asp Cys Ala Met Val
            740                 745                 750

CCG ATG CTC TAT AGC TGG GAC AGG ATC GCG GCA GAG GCC GTG ACG TCG       2304
Pro Met Leu Tyr Ser Trp Asp Arg Ile Ala Ala Glu Ala Val Thr Ser
        755                 760                 765
```

*FIG. 1H*

CAG GAA CTC GTC CCG GCC TGA          2325
Gln Glu Leu Val Pro Ala
    770

FIG. 1I

| | | | | | | | | | |
|---|---|---|---|---|---|---|---|---|---|
| ATG | ACT | ATG | GCA | GCT | AAT | ACG | GAT | CGC | GCG | GTC | TTG | CAG | GCG | CTG | 48
| Met | Thr | Met | Ala | Ala | Asn | Thr | Asp | Arg | Ala | Val | Leu | Gln | Ala | Leu |
| -1 | | 1 | | | 5 | | | | | 10 | | | | 15 |

| CCG | CCG | CTT | TCC | GGC | AGC | CTC | CCC | ATT | CCC | GGA | TTG | AGC | GCG | GTC | 96
| Pro | Pro | Leu | Ser | Gly | Ser | Leu | Pro | Ile | Pro | Gly | Leu | Ser | Ala | Val |
| | | 20 | | | | | 25 | | | | | 30 | | |

| CGC | GTC | CGG | CGC | GAT | GCC | TGG | GGC | ATC | CCG | CAT | ATC | AAG | GCC | TCG | GGC | 144
| Arg | Val | Arg | Arg | Asp | Ala | Trp | Gly | Ile | Pro | His | Ile | Lys | Ala | Ser | Gly |
| | | 35 | | | | | 40 | | | | | 45 | | | |

| GAG | GCC | GAT | GCC | TAT | CGG | GCG | CTG | TTC | GTC | CAT | TCG | CAG | GAC | CGT | 192
| Glu | Ala | Asp | Ala | Tyr | Arg | Ala | Leu | Phe | Val | His | Ser | Gln | Asp | Arg |
| | 50 | | | | | 55 | | | | | 60 | | | |

| CTT | TTC | CAG | ATG | GAG | CTG | ACG | CGT | CGC | AAG | GCG | CTG | GGA | CGC | GCC | 240
| Leu | Phe | Gln | Met | Glu | Leu | Thr | Arg | Arg | Lys | Ala | Leu | Gly | Arg | Ala |
| 65 | | | | | 70 | | | | | 75 | | | | |

| GAA | TGG | CTG | GGC | GCC | GAG | GCC | GCC | GAT | ATC | CTC | GTG | CGC | CGG | 288
| Glu | Trp | Leu | Gly | Ala | Glu | Ala | Ala | Asp | Ile | Leu | Val | Arg | Arg |
| 80 | | | | 85 | | | | | 90 | | | | 95 |

FIG. 2A

```
CTC GGA ATG GAA AAA GTC TGC CGG CGC GAC TTC GAG GCC TTG GGC GTC    336
Leu Gly Met Glu Lys Val Cys Arg Arg Asp Phe Glu Ala Leu Gly Val
            100                 105                 110

GAG GCG AAG GAC ATG CTG CGG GCT TAT GTC GCC GGC GTG AAC GCA TTC    384
Glu Ala Lys Asp Met Leu Arg Ala Tyr Val Ala Gly Val Asn Ala Phe
        115                 120                 125

CTG GCT TCC GGT GCT CCC CTG CCT GTC GAA TAC GGA TTG CTC GGA GCA    432
Leu Ala Ser Gly Ala Pro Leu Pro Val Glu Tyr Gly Leu Leu Gly Ala
    130                 135                 140

GAG CCG GAG CCC TGG GAG CCT TGG CAC AGC ATC GCG GTG ATG CGC CGG    480
Glu Pro Glu Pro Trp Glu Pro Trp His Ser Ile Ala Val Met Arg Arg
145                 150                 155

CTG GGC CTG CTT ATG GGT TCG GTG TGG TTC AAG CTC TGG CGG ATG CTG    528
Leu Gly Leu Leu Met Gly Ser Val Trp Phe Lys Leu Trp Arg Met Leu
160                 165                 170                 175

GCG CTG CCG GTC GTC GGA GCG AAT GCG GCG CTG AAG CTG CGC TAT GAC    576
Ala Leu Pro Val Val Gly Ala Asn Ala Ala Leu Lys Leu Arg Tyr Asp
            180                 185                 190
```

*FIG.2B*

```
GAT GGC CGG GAT TTG CTC TGC ATC CCG CCG GGC GCC GAA GCC GAT    624
Asp Gly Arg Asp Leu Leu Cys Ile Pro Pro Gly Ala Glu Ala Asp
Gly     195             200             205
```

FIG.2C

```
CGG CTC GAG GCG GAT CTC GCG ACC CTG CGG CCC GCG GTC GAT GCG CTG    672
Arg Leu Glu Ala Asp Leu Ala Thr Leu Arg Pro Ala Val Asp Ala Leu
210                 215                 220

CTG AAG GCG ATG GGC GAT GCC TCC GAT GCT GCC GGC GGA TCC              720
Leu Lys Ala Met Gly Gly Asp Ala Ser Asp Ala Ala Gly Gly Ser
    225                 230                 235

AAC AAC TGG GCG GTC GCT CCG GGC ACG GCG CGC AGG CCG ATC              768
Asn Asn Trp Ala Val Ala Pro Gly Arg Thr Ala Arg Pro Ile
240                 245                 250                 255

CTC GGC GAT CCG CAT CGC GCC GTC TTC GAA ATC CCG GGC ATG TAT GCG    816
Leu Gly Asp Pro His Arg Val Phe Glu Ile Pro Gly Met Tyr Ala
                260                 265                 270

CAG CAT CAT CTG TGC GAC CGG TTC GAC ATG ATC GGC CTG ACC GTG          864
Gln His His Leu Cys Asp Arg Phe Asp Met Ile Gly Leu Thr Val
    275                 280                 285

CCG GGC GTG CCG GGC TTC CCG CAC TTC GCG CAT AAC GGC AAG GTC GCC    912
Pro Gly Val Pro Gly Phe Pro His Phe Ala His Asn Gly Lys Val Ala
290                 295                 300
```

*FIG. 2D*

```
TAT AGC GTC ACG CAT GCC TTC ATG GAC ATC CAC GAT CTC TAT CTC GAG   960
Tyr Ser Val Thr His Ala Phe Met Asp Ile His Asp Leu Tyr Leu Glu
    305                 310                 315

CAG TTC GCG GGG GAG GGC CGC ACT GCG CGG TTC GGC AAC GAT TTC GAG  1008
Gln Phe Ala Gly Glu Gly Arg Thr Ala Arg Phe Gly Asn Asp Phe Glu
320                 325                 330                 335

CCC GTC GCC TGG AGC CGG GAC CGT ATC GCG GTC GTC CGG GGT GGC GAT  1056
Pro Val Ala Trp Ser Arg Asp Arg Ile Ala Val Arg Gly Gly Ala Asp
                340                 345                 350

CGC GAG TTC GAT ATC GTC GAG ACG CGC CAT GGC CCG GTT ATC GCG GGC  1104
Arg Glu Phe Asp Ile Val Glu Thr Arg His Gly Pro Val Ile Ala Gly
        355                 360                 365

GAT CCG CGC GAT GGC GCA GCG CTC ACG CTG CGT TCG GTC CAG TTC GCC  1152
Asp Pro Arg Asp Gly Ala Ala Leu Thr Leu Arg Ser Val Gln Phe Ala
370                 375                 380

GAG ACC GAT CTG TCC TTC GAC TGC CTG ACG CGG ATG CCG GGC GCA TCG  1200
Glu Thr Asp Leu Ser Phe Asp Cys Leu Thr Arg Met Pro Gly Ala Ser
385                 390                 395
```

FIG. 2E

```
ACC GTC GCC CAG CTC TAC GAC GCG ACG CGC GGC TGG GGC CTG ATC GAC      1248
Thr Val Ala Gln Leu Tyr Asp Ala Thr Arg Gly Trp Gly Leu Ile Asp
400             405                 410                 415
```

*FIG.2F*

```
CAT AAC CTC GTC GCC GGG GAT GTC GCG GGC TCG ATC GGC CAT CTG GTC      1296
His Asn Leu Val Ala Gly Asp Val Ala Gly Ser Ile Gly His Leu Val
            420                 425                 430

CGC GCC CGC GTT CCG TCC CGT CCG CGC GAA AAC GGC TGG CCG GTG          1344
Arg Ala Arg Val Pro Ser Arg Pro Arg Glu Asn Gly Trp Leu Pro Val
            435                 440                 445

CCG GGC TGG TCC GGC GAG CAT GAA TGG CGG GGC TGG ATT CCG CAC GAG      1392
Pro Gly Trp Ser Gly Glu His Glu Trp Arg Gly Trp Ile Pro His Glu
            450                 455                 460

GCG ATG CCG CGC GTG GCC ATC GAT CCG GGC GGC ATC GTC ATC ACG GCG      1440
Ala Met Pro Arg Val Ala Ile Asp Pro Gly Gly Ile Val Ile Thr Ala
            465                 470                 475

AAT AAT CGC GTG GTG GCC GAT GAC CAT CCC GAT TAT CTC TGC ACC GAT      1488
Asn Asn Arg Val Val Ala Asp Asp His Pro Asp Tyr Leu Cys Thr Asp
            480                 485                 490                 495

TGC CAT CCC TAC CGC GCC GAG CGC ATC ATG AAG CGC CTG GTC GCC          1536
Cys His Pro Tyr Arg Ala Glu Arg Ile Met Lys Arg Leu Val Ala
            500                 505                 510
```

FIG.2G

```
AAT CCG GCT TTC GCC GTC GAC GAT GCC GCG ATC CAT GCC GAT ACT    1584
Asn Pro Ala Phe Ala Val Asp Asp Ala Ala Ile His Ala Asp Thr
        515             520             525

CTG TCG CCC CAT GTC GGG TTG CTG CGC AGG CTC GAG GCG CTT GGA    1632
Leu Ser Pro His Val Gly Leu Leu Arg Arg Leu Glu Ala Leu Gly
        530             535             540

GCC CGC GAC GAC TCC GCG GCC GAA GGG CTG AGG CAG ATG CTC GCC    1680
Ala Arg Asp Asp Ser Ala Ala Glu Gly Leu Arg Gln Met Leu Val
        545             550             555

TGG GAC GGC CGC ATG GAT GCG GCT TCG GAG GTC GCG TCT GCC TAC AAT    1728
Trp Asp Gly Arg Met Asp Ala Ala Ser Glu Val Ala Ser Ala Tyr Asn
        560             565             570             575

GCG TTC CGC AGG GGG ATA CGG ACG CGG CTG GTG ACG GAC CGC AGC GGG CTG    1776
Ala Phe Arg Arg Gly Ala Thr Arg Leu Val Thr Asp Arg Ser Gly Leu
        580             585             590

GAG CAG GCG ATA TCG CAT CCC TTC GCG GCT GTC GCG CCG GGC GTC TCA    1824
Glu Gln Ala Ile Ser His Pro Phe Ala Val Ala Pro Gly Val Ser
        595             600             605
```

*FIG. 2H*

```
CCG CAA GGC CAG GTC TGG TGG GCC GTG CCG ACC CTG CTG CGC GAC GAC   1872
Pro Gln Gly Gln Val Trp Trp Ala Val Pro Thr Leu Leu Arg Asp Asp
    610             615             620
```

*FIG. 21*

| | | | | | | | | | | | | | | | |
|---|---|---|---|---|---|---|---|---|---|---|---|---|---|---|---|
| GAT | GCC | GGA | ATG | CTG | AAG | GGC | TGG | AGC | TGG | GAC | CAG | GCC | TTG | TCT | GAG |
| Asp | Ala | Gly | Met | Leu | Lys | Gly | Trp | Ser | Trp | Asp | Gln | Ala | Leu | Ser | Glu |
| 625 | | | | | 630 | | | | | 635 | | | | | |

1920

| GCC | CTC | TCG | GTC | GCG | TCG | CAG | AAC | CTG | ACC | GGG | CGA | AGC | TGG | GGC | GAA |
|---|---|---|---|---|---|---|---|---|---|---|---|---|---|---|---|
| Ala | Leu | Ser | Val | Ala | Ser | Gln | Asn | Leu | Thr | Gly | Arg | Ser | Trp | Gly | Glu |
| 640 | | | | 645 | | | | | 650 | | | | | 655 | |

1968

| GAG | CAT | CGG | CCG | CGC | TTC | ACG | CAT | CCG | CTT | GCC | ACG | CAA | TTC | CCG | GCC |
|---|---|---|---|---|---|---|---|---|---|---|---|---|---|---|---|
| Glu | His | Arg | Pro | Arg | Phe | Thr | His | Pro | Leu | Ala | Thr | Gln | Phe | Pro | Ala |
| | | 660 | | | | | 665 | | | | | 670 | | | |

2016

| TGG | GCG | GGG | CTG | AAT | CCG | GCT | TCC | CGT | CCG | ATC | GGT | GGC | GAT | GGC | GGG |
|---|---|---|---|---|---|---|---|---|---|---|---|---|---|---|---|
| Trp | Ala | Gly | Leu | Asn | Pro | Ala | Ser | Arg | Pro | Ile | Gly | Gly | Asp | Gly | Gly |
| | 675 | | | | | 680 | | | | | 685 | | | | |

2064

| GAT | ACC | GTG | CTG | CTG | AAC | GGG | CTC | GTC | CCG | TCA | GCC | GGG | CCG | CAG | GCG |
|---|---|---|---|---|---|---|---|---|---|---|---|---|---|---|---|
| Asp | Thr | Val | Leu | Leu | Asn | Gly | Leu | Val | Pro | Ser | Ala | Gly | Pro | Gln | Ala |
| | 690 | | | | | 695 | | | | | 700 | | | | |

2112

| ACC | TAT | GGT | GCC | CTG | TCG | CGC | TAC | GTC | TTC | GAT | GTC | GGC | AAT | TGG | GAC |
|---|---|---|---|---|---|---|---|---|---|---|---|---|---|---|---|
| Thr | Tyr | Gly | Ala | Leu | Ser | Arg | Tyr | Val | Phe | Asp | Val | Gly | Asn | Trp | Asp |
| 705 | | | | 710 | | | | | 715 | | | | | | |

2160

*FIG. 2J*

```
AAT AGC CGC TGG GTC GTC TTC CAC GGC GCC TCC GGG CAT CCG GCC AGC      2208
Asn Ser Arg Trp Val Val Phe His Gly Ala Ser Gly His Pro Ala Ser
720                 725                 730                 735

GCC CAT TAT GCC GAT CAG AAT GCG CCC TGG AGC GAC TGT GCG ATG GTG      2256
Ala His Tyr Ala Asp Gln Asn Ala Pro Trp Ser Asp Cys Ala Met Val
        740                 745                 750

CCG ATG CTC TAT AGC TGG GAC AGG ATC GCG GCA GAG GCC GTG ACG TCG      2304
Pro Met Leu Tyr Ser Trp Asp Arg Ile Ala Ala Glu Ala Val Thr Ser
        755                 760                 765

CAG GAA CTC GTC CCG GCC TGA                                          2325
Gln Glu Leu Val Pro Ala
770
```

*FIG. 2K*

FIG. 3A

| ATG | ACT | ATG | GCA | GCT | AAT | ACG | GAT | CGC | GCG | GTC | TTG | CAG | GCG | CTG | |
|-----|-----|-----|-----|-----|-----|-----|-----|-----|-----|-----|-----|-----|-----|-----|---|
| Met | Thr | Met | Ala | Ala | Asn | Thr | Asp | Arg | Ala | Val | Leu | Gln | Ala | Leu | |
| -1  | 1   |     |     |     | 5   |     |     |     |     | 10  |     |     |     | 15  | 48 |

| CCG | CCC | CTT | TCC | GGC | AGC | CTC | CCC | ATT | CCC | GGA | TTG | AGC | GCG | GTC | |
|-----|-----|-----|-----|-----|-----|-----|-----|-----|-----|-----|-----|-----|-----|-----|---|
| Pro | Pro | Leu | Ser | Gly | Ser | Leu | Pro | Ile | Pro | Gly | Leu | Ser | Ala | Ser | |
|     |     |     | 20  |     |     |     |     | 25  |     |     |     |     | 30  |     | 96 |

| CGC | GTC | CGG | CGC | GAT | GCC | TGG | GGC | ATC | CCG | CAT | ATC | AAG | GCC | TCG | GGC | |
|-----|-----|-----|-----|-----|-----|-----|-----|-----|-----|-----|-----|-----|-----|-----|-----|---|
| Arg | Val | Arg | Arg | Asp | Ala | Trp | Gly | Ile | Pro | His | Ile | Lys | Ala | Ser | Gly | |
|     |     | 35  |     |     |     |     | 40  |     |     |     |     | 45  |     |     |     | 144 |

| GAG | GCC | GAT | GCC | TAT | CGG | GCT | CTG | GCC | TTC | GTC | CAT | TCG | CAG | GAC | CGT | |
|-----|-----|-----|-----|-----|-----|-----|-----|-----|-----|-----|-----|-----|-----|-----|-----|---|
| Glu | Ala | Asp | Ala | Tyr | Arg | Ala | Leu | Ala | Phe | Val | His | Ser | Gln | Asp | Arg | |
|     | 50  |     |     |     |     | 55  |     |     |     |     | 60  |     |     |     |     | 192 |

| CTT | TTC | CAG | ATG | GAG | CTG | ACG | CGT | CGC | AAG | GCC | CTG | GGA | CGC | GCG | GCC | |
|-----|-----|-----|-----|-----|-----|-----|-----|-----|-----|-----|-----|-----|-----|-----|-----|---|
| Leu | Phe | Gln | Met | Glu | Leu | Thr | Arg | Arg | Lys | Ala | Leu | Gly | Arg | Ala | Ala | |
| 65  |     |     |     |     | 70  |     |     |     |     | 75  |     |     |     |     |     | 240 |

| GAA | TGG | CTG | GGC | GCC | GAG | GCC | GAT | ATC | CTC | GTG | CGC | CGG | |
|-----|-----|-----|-----|-----|-----|-----|-----|-----|-----|-----|-----|-----|---|
| Glu | Trp | Leu | Gly | Ala | Glu | Ala | Asp | Ile | Leu | Val | Arg | Arg | |
| 80  |     |     |     | 85  |     |     |     | 90  |     |     |     | 95  | 288 |

```
CTC GGA ATG GAA AAA GTC TGC CGG CGC GAC TCC GAG GCC TTG GGC GTC    336
Leu Gly Met Glu Lys Val Cys Arg Arg Asp Phe Glu Ala Leu Gly Val
            100                 105                 110

GAG GCG AAG GAC ATG CTG CGG GCT TAT GTC GCC GGC GTG AAC GCA TTC    384
Glu Ala Lys Asp Met Leu Arg Ala Tyr Val Ala Gly Val Asn Ala Phe
        115                 120                 125

CTG GCT TCC GGT GCT CCC CTG CCT GTC GAA TAC GGA TTG CTC GGA GCA    432
Leu Ala Ser Gly Ala Pro Leu Pro Val Glu Tyr Gly Leu Leu Gly Ala
            130                 135                 140

GAG CCG GAG CCC TGG GAG CCT TGG CAC AGC ATC GCG GTG ATG CGC CGG    480
Glu Pro Glu Pro Trp Glu Pro Trp His Ser Ile Ala Val Met Arg Arg
        145                 150                 155

CTG GGC CTG CTT ATG GGT TCG GTG TGG TTC AAG CTC TGG CGG ATG CTG    528
Leu Gly Leu Leu Met Gly Ser Val Trp Phe Lys Leu Trp Arg Met Leu
            160                 165                 170    175

GCG CTG CCG GTG GTC GGA GCC AAT GCG GCG AAG CTG CGC TAT GAC        576
Ala Leu Pro Val Val Gly Ala Asn Ala Ala Lys Leu Arg Tyr Asp
        180                 185                 190
```

FIG. 3B

```
GAT GGC GGC CGG GAT TTG CTC TGC ATC CCG CCG GGC GCC GAA GCC GAT
Asp Gly Gly Arg Asp Leu Leu Cys Ile Pro Pro Gly Ala Glu Ala Asp
        195             200             205
```

624

FIG. 3C

```
CGG CTC GAG GCG GAT CTC GCG ACC CTG CGG CCC GCG GTC GAT GCG CTG    672
Arg Leu Glu Ala Asp Leu Ala Thr Leu Arg Pro Ala Val Asp Ala Leu
210                         215                      220

CTG AAG GCG ATG GGC GAT GCT TCC GAT GCT GCC GGC GGC AGC            720
Leu Lys Ala Met Gly Gly Asp Ala Ser Asp Ala Ala Gly Gly Ser
225                      230                   235

AAC AAC TGG GCG GTC GCT CCT GGC CGC ACG GCG ACC GGC AGG CCG ATC    768
Asn Asn Trp Ala Val Ala Pro Gly Arg Thr Ala Thr Gly Arg Pro Ile
240                     245                 250                 255

CTC GCG GAT CCG GTC CAT CGC GTC TTC GAA ATC CCT GGC TAT TAT GCG    816
Leu Ala Gly Asp Pro His Arg Val Phe Glu Ile Pro Gly Tyr Tyr Ala
          260                    265                     270

CAG CAT CAT CTG GCC TGC GAC CGG TTC GAC ATG ATC GGC CTG ACC GTG    864
Gln His His Leu Ala Cys Asp Arg Phe Asp Met Ile Gly Leu Thr Val
            275                     280                    185

CCG GGC GTG CCG GGC TTC CCG CAC TTC GCG CAT AAC GGC AAG GTC GCC    912
Pro Gly Val Pro Gly Phe Pro His Phe Ala His Asn Gly Lys Val Ala
            290                     295                    300
```

FIG. 3D

| TAT | TGC | GTC | ACC | CAT | GCC | TTC | ATG | GAC | ATC | CAC | GAT | CTC | TAT | CTC | GAG | 960 |
| Tyr | Cys | Val | Thr | His | Ala | Phe | Met | Asp | Ile | His | Asp | Leu | Tyr | Leu | Glu | |
| | 305 | | | | 310 | | | | 315 | | | | | | | |

| CAG | TTC | GCG | GGG | GAG | GGC | CGC | ACT | GCG | CGG | AAC | GAT | TTC | GAG | 1008 |
| Gln | Phe | Ala | Gly | Glu | Gly | Arg | Thr | Ala | Arg | Asn | Asp | Phe | Glu | |
| 320 | | | | 325 | | | | 330 | | | | | 335 | |

| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | | 340 | | | | 345 | | | | | 350 | | | |

| CGC | GAG | TTC | GAT | ATC | GTC | GAG | ACG | CAT | GGC | CCG | GTT | ATC | GCG | GGC | 1104 |
| Arg | Glu | Phe | Asp | Ile | Val | Glu | Thr | His | Gly | Pro | Val | Ile | Ala | Gly | |
| 355 | | | | | | 360 | | | | | 365 | | | | |

| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | 370 | | | | | 375 | | | | | 380 | | | | | |

| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| 385 | | | | | 390 | | | | | 395 | | | | | | |

FIG. 3E

```
ACC GTG GCC CAG CTC TAC GAC GCG ACG CGC GGC TGG GGC CTG ATC GAC       1248
Thr Val Ala Gln Leu Tyr Asp Ala Thr Arg Gly Trp Gly Leu Ile Asp
400             405                 410                 415
```

FIG. 3F

| CAT | AAC | CTC | GTC | GCC | GGG | GAT | GTC | GCG | GGC | TCG | ATC | GGC | CAT | CTG | GTC | 1296 |
| His | Asn | Leu | Val | Ala | Gly | Asp | Val | Ala | Gly | Ser | Ile | Gly | His | Leu | Val | |
| | | | | 420 | | | | | 425 | | | | | 430 | | |

| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val | |
| | | 435 | | | | | 440 | | | | | 445 | | | | |

| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu | |
| | 450 | | | | | 455 | | | | | 460 | | | | | |

| GCG | ATG | CCG | CGC | GTG | GTG | ATC | GAT | CCG | GGC | GGC | TGG | ATC | GTC | ACG | GCG | 1440 |
| Ala | Met | Pro | Arg | Val | Val | Ile | Asp | Pro | Gly | Gly | Trp | Ile | Val | Thr | Ala | |
| 465 | | | | | 470 | | | | | 475 | | | | | | |

| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp | |
| 480 | | | | | 485 | | | | | 490 | | | | | 495 | |

| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala | |
| | | | 500 | | | | | 505 | | | | | 510 | | | |

*FIG. 3G*

```
AAT CCG GCT TTC GCC GTC GAC GAT GCC GCC GCG ATC CAT GCC GAT ACG    1584
Asn Pro Ala Phe Ala Val Asp Asp Ala Ala Ala Ile His Ala Asp Thr
         515                 520                 525

CTG TCG CCC CAT GTC GGG TTC CTG CGC CGG AGG CTC GAG GCG CTT GGA    1632
Leu Ser Pro His Val Gly Phe Leu Arg Arg Arg Leu Glu Ala Leu Gly
             530                 535                 540

GCC CGC GAC GAC TCC GCG GCC GAA GGG CTG AGG CAG ATG CTC GTC GCC    1680
Ala Arg Asp Asp Ser Ala Ala Glu Gly Leu Arg Gln Met Leu Val Ala
         545                 550                 555

TGG GAC GGC CGC ATG GAT GCG GCT TCG GAG GTC GCG TCT GCC TAC AAT    1728
Trp Asp Gly Arg Met Asp Ala Ala Ser Glu Val Ala Ser Ala Tyr Asn
    560                 565                 570                 575

GCG TTC CGC AGG GCG CTG ACG CGG CTG GTG ACG GAC CGC AGC GGG CTG    1776
Ala Phe Arg Arg Ala Leu Thr Arg Leu Val Thr Asp Arg Ser Gly Leu
             580                 585                 590

GAG CAG GCG ATA TCG CAT CCC TTC GCG GCT GTC GCG CCG GGC GTC TCA    1824
Glu Gln Ala Ile Ser His Pro Phe Ala Ala Val Ala Pro Gly Val Ser
             595                 600                 605
```

*FIG. 3H*

CCG CAA GGC CAG GTC TGG TGG GCC GTG CCG ACC CTG CTG CGC GAC GAC 1872
Pro Gln Gly Gln Val Trp Trp Ala Val Pro Thr Leu Leu Arg Asp Asp
610             615                 620

FIG. 31

```
GAT GCC GGA ATG CTG AAG GGC TGG AGC TGG GAC CAG GCC TTG TCT GAG      1920
Asp Ala Gly Met Leu Lys Gly Trp Ser Trp Asp Gln Ala Leu Ser Glu
    625             630             635             655

GCC CTC TCG GTC GCC TCG CAG AAC CTG ACC GGG AGC TGG GGC GAA          1968
Ala Leu Ser Val Ala Ser Gln Asn Leu Thr Gly Arg Ser Trp Gly Glu
    640             645             650             655

GAG CAT CGG CCG CGC TTC ACG CAT CCG CTT GCC ACG CAA TTC CCG GCC      2016
Glu His Arg Pro Arg Phe Thr His Pro Leu Ala Thr Gln Phe Pro Ala
            660             665             670

TGG GCG GGG CTG CTG AAT CCG GCT TCC CGT CCG ATC GGT GAT GGC          2064
Trp Ala Gly Leu Leu Asn Pro Ala Ser Arg Pro Ile Gly Asp Gly
    675             680             685

GAT ACC GTG CTG GCG AAC GGG CTC GTC CCG TCA GCC GGG CCG CAG GCG      2112
Asp Thr Val Leu Ala Asn Gly Leu Val Pro Ser Ala Gly Pro Gln Ala
    690             695             700

ACC TAT GGT GCC CTG TCG CGC TAC GTC TTC GAT GTC GGC AAT TGG GAC      2160
Thr Tyr Gly Ala Leu Ser Arg Tyr Val Phe Asp Val Gly Asn Trp Asp
    705             710             715
```

*FIG. 3J*

```
AAT AGC CGC TGG GTC GTC TTC CAC GGC GCC TCC GGG CAT CCG GCC AGC    2208
Asn Ser Arg Trp Val Val Phe His Gly Ala Ser Gly His Pro Ala Ser
720                 725                 730                 735

GCC CAT TAT GCC GAT CAG AAT GCG CCC TGG AGC GAC TGT GCG ATG GTG    2256
Ala His Tyr Ala Asp Gln Asn Ala Pro Trp Ser Asp Cys Ala Met Val
        740                 745                 750

CCG ATG CTC TAT AGC TGG GAC AGG ATC GCG GCA GAG GCC GTG ACG TCG    2304
Pro Met Leu Tyr Ser Trp Asp Arg Ile Ala Ala Glu Ala Val Thr Ser
        755                 760                 765

CAG GAA CTC GTC CCG GCC TGA                                         2325
Gln Glu Leu Val Pro Ala
770
```

*FIG. 3K*

```
ATG ACT ATG GCA GCT AAT ACG GAT CGC GCG GTC TTG CAG GCG GCG CTG    48
Met Thr Met Ala Ala Asn Thr Asp Arg Ala Val Leu Gln Ala Ala Leu
 -1   1                   5                  10                  15

CCG CCG CTT TCC GGC AGC CTC CCC ATT CCC GGA TTG AGC GCG TCG GTC    96
Pro Pro Leu Ser Gly Ser Leu Pro Ile Pro Gly Leu Ser Ala Ser Val
              20                  25                  30

CGC GTC CGG CGC GAT GCC TGG GGC ATC CAT ATC AAG GCC TCG GGC       144
Arg Val Arg Arg Asp Ala Trp Gly Ile His Ile Lys Ala Ser Gly
         35                  40                  45

GAG GCC GAT GCC TAT CGG GCG CTG TTC GTC CAT TCG CAG GAC CGT       192
Glu Ala Asp Ala Tyr Arg Ala Leu Phe Val His Ser Gln Asp Arg
         50                  55                  60

CTT TTC CAG ATG GAG CTG ACG CGT CGC AAG GCG GGA CGC CGG GCC GCC   240
Leu Phe Gln Met Glu Leu Thr Arg Arg Lys Ala Gly Arg Arg Ala Ala
 65                  70                  75

GAA TGG CTG GGC GCC GAG GCC GAT ATC CTC GTG CGC CGG           288
Glu Trp Leu Gly Ala Glu Ala Asp Ile Leu Val Arg Arg
 80                  85                  90                  95
```

*FIG. 4A*

FIG. 4B

```
CTC GGA ATG GAA AAA GTC TGC CGG CGC GAC TTC GAG GCC TTG GGC GTC    336
Leu Gly Met Glu Lys Val Cys Arg Arg Asp Phe Glu Ala Leu Gly Val
            100             105             110

GAG GCG AAG GAC ATG CTG CGG GCT TAT GTC GCC GGC GTG AAC GCA TTC    384
Glu Ala Lys Asp Met Leu Arg Ala Tyr Val Ala Gly Val Asn Ala Phe
        115             120             125

CTG GCT TCC GGT GCT CCC CTG CCT GTC GAA TAC GGA TTG GGA GCA        432
Leu Ala Ser Gly Ala Pro Leu Pro Val Glu Tyr Gly Leu Gly Ala
        130             135             140

GAG CCG GAG CCC TGG GAG CCT GTC CAC AGC ATC GCG GTG ATG CGC CGG    480
Glu Pro Glu Pro Trp Glu Pro Val His Ser Ile Ala Val Met Arg Arg
    145             150             155

CTG GGC CTT ATG GGT TCG GTG TGG TTC AAG CTC TGG CGG ATG CTG        528
Leu Gly Leu Met Gly Ser Val Trp Phe Lys Leu Trp Arg Met Leu
    160         165             170             175

GCG CTG CCG GTG GTC GGA GCC GCG AAT GCC CTG AAG CTG CGC TAT GAC    576
Ala Leu Pro Val Val Gly Ala Ala Asn Ala Leu Lys Leu Arg Tyr Asp
        180             185             190
```

```
GAT GGC GGC CGG GAT TTG CTC TGC ATC CCG CCG GGC GCC GAA GCC GAT      624
Asp Gly Gly Arg Asp Leu Leu Cys Ile Pro Pro Gly Ala Glu Ala Asp
         195                 200                 205
```

FIG. 4C

```
CGG CTC GAG GCG GAT CTC GCG ACC CTG CGG CCC GCG GTC GAT GCG CTG    672
Arg Leu Glu Ala Asp Leu Ala Thr Leu Arg Pro Ala Val Asp Ala Leu
        210                 215                 220

CTG AAG GCG ATG GGC GGT GGC GAT GCT TCC GAT GCT GCC GGC GGC AGC    720
Leu Lys Ala Met Gly Gly Gly Asp Ala Ser Asp Ala Ala Gly Gly Ser
    225                 230                 235

AAC AAC TGG GCG GTC GTC GCG CCG GGC CGC ACG GCG ACC GGC GGC ATC    768
Asn Asn Trp Ala Val Val Ala Pro Gly Arg Thr Ala Thr Gly Gly Ile
240                 245                 250                 255

CTC GCG GAT CCG CAT CGC GTC TTC GAA ATC CCG GGC ATG TAC TAT        816
Leu Ala Gly Asp Pro His Arg Val Phe Glu Ile Pro Gly Met Tyr Tyr
                        260                 265                 270

CAG CAT CAT CTG GCC TGC GAC CGG TTC GAC ATG ATC GGC CTG ACC GTG    864
Gln His His Leu Ala Cys Asp Arg Phe Asp Met Ile Gly Leu Thr Val
                275                 280                 285

CCG GGC GTG CCG GGC TTC CCG CAC TTC GCG CAT AAC GGC AAG GTC GCC    912
Pro Gly Val Pro Gly Phe Pro His Phe Ala His Asn Gly Lys Val Ala
    290                 295                 300
```

FIG. 4D

```
TAT TGC GTC ACC CAT GCC TTC ATG GAC ATC CAC GAT CTC TAT CTC GAG      960
Tyr Cys Val Thr His Ala Phe Met Asp Ile His Asp Leu Tyr Leu Glu
305             310                 315                 335

CAG TTC GCG GGG GAG GGC ACT GCG CGG TCC GGA AAC GAT TTC GAG         1008
Gln Phe Ala Gly Glu Gly Thr Ala Arg Phe Gly Asn Asp Phe Glu
320             325                 330                 335

CCC GTC GCC TGG AGC GAC CGT ATC GCG GTC GTC CGG GGT GCC GAT         1056
Pro Val Ala Trp Ser Asp Arg Ile Ala Val Val Arg Gly Ala Asp
        340                 345                 350

CGC GAG TTC GAT ATC GTC GAG ACG CGC CAT GGC CCG GTT ATC GCG GGC     1104
Arg Glu Phe Asp Ile Val Glu Thr Arg His Gly Pro Val Ile Ala Gly
        355                 360                 365

GAT CCG CGC GAT GGC GCA GCG CTC ACG CTG CGT TCG GTC CAG TTC GCC     1152
Asp Pro Arg Asp Gly Ala Ala Leu Thr Leu Arg Ser Val Gln Phe Ala
370                 375                 380

GAG ACC TGC CTG GAT CTG TCC TTC GAC ACG CGG ATG CCG GGC GCA TCG     1200
Glu Thr Cys Leu Asp Leu Ser Phe Asp Thr Arg Met Pro Gly Ala Ser
385                 390                 395
```

*FIG. 4E*

ACC GTG GCC CAG CTC TAC GAC GCG ACG CGC GGC TGG GGC CTG ATC GAC   1248
Thr Val Ala Gln Leu Tyr Asp Ala Thr Arg Gly Trp Gly Leu Ile Asp
400             405                 410                 415

FIG. 4F

```
CAT AAC CTC GTC GCC GGG GAT GTC GCG GGC TCG ATC GGC CAT CTG GTC        1296
His Asn Leu Val Ala Gly Asp Val Ala Gly Ser Ile Gly His Leu Val
            420                 425                 430

CGC GCC CGC GTT CCG TCC CGT CCG CGC GAA AAC GGC TGG CTG CCG GTG        1344
Arg Ala Arg Val Pro Ser Arg Pro Arg Glu Asn Gly Trp Leu Pro Val
            435                 440                 445

CCG GGC TGG TCC GGC GAG CAT GAA CAT GAA ATT CCG CAC GAG                1392
Pro Gly Trp Ser Gly Glu His Glu His Glu Ile Pro His Glu
            450                 455                 460

GCG ATG CCG CGC GTG ATC GAT CTG ATC GAT CCG GGC GGC ATC GTC ACG GCG    1440
Ala Met Pro Arg Val Ile Asp Leu Ile Asp Pro Gly Gly Ile Val Thr Ala
            465                 470                 475

AAT AAT CGC GTC GTG GCC GAT GAC CAT CCC GAT TAT CTC TGC ACC GAT        1488
Asn Asn Arg Val Val Ala Asp Asp His Pro Asp Tyr Leu Cys Thr Asp
            480                 485                 490                 495

TGC CAT CCG CCC TAC CGC GCC GAG CGC ATC ATG AAG CGC CTG GTC GCC        1536
Cys His Pro Pro Tyr Arg Ala Glu Arg Ile Met Lys Arg Leu Val Ala
            500                 505                 510
```

*FIG. 4G*

```
AAT CCG GCT TTC GCC GTC GAC GAT GCC GCG ATC CAT GCC GAT ACG      1584
Asn Pro Ala Phe Ala Val Asp Asp Ala Ala Ile His Ala Asp Thr
        515             520             525

CTG TCG CCC CAT GTC GGG TTG CTG CGC AGG CTC GAG GCG CTT GGA      1632
Leu Ser Pro His Val Gly Leu Leu Arg Arg Leu Glu Ala Leu Gly
        530             535             540

GCC CGC GAC GAC TCC GCG GCC GAA GGG CTG AGG CAG ATG CTC GCC      1680
Ala Arg Asp Asp Ser Ala Ala Glu Gly Leu Arg Gln Met Leu Ala
        545             550             555

TGG GAC GGC CGC ATG GAT GCG GCT TCG GAG GTC GCC TCT GCC TAC AAT  1728
Trp Asp Gly Arg Met Asp Ala Ala Ser Glu Val Ala Ser Ala Tyr Asn
    560             565             570             575

GCG TTC CGC AGG GCG CTG ACG CGG GAC CGC AGC GGG CTG           1776
Ala Phe Arg Arg Ala Leu Thr Arg Asp Arg Ser Gly Leu
        580             585             590

GAG CAG GCG ATA TCG CAT CCC TTC GCG GCT GTC GCC CCG GGC GTC TCA  1824
Glu Gln Ala Ile Ser His Pro Phe Ala Ala Val Ala Pro Gly Val Ser
    595             600             605
```

FIG. 4H

```
CCG CAA GGC CAG GTC TGG TGG GCC GTG CCG ACC CTG CTG CGC GAC GAC    1872
Pro Gln Gly Gln Val Trp Trp Ala Val Pro Thr Leu Leu Arg Asp Asp
    610             615             620
```

*FIG. 4I*

```
GAT GCC GGA ATG CTG AAG GGC TGG AGC TGG GAC CAG GCC TTG TCT GAG    1920
Asp Ala Gly Met Leu Lys Gly Trp Ser Trp Asp Gln Ala Leu Ser Glu
          625                 630                 635

GCC CTC TCG GTC GCG TCG CAG AAC CTG ACC GGG CGA AGC TGG GGC GAA    1968
Ala Leu Ser Val Ala Ser Gln Asn Leu Thr Gly Arg Ser Trp Gly Glu
          640                 645                 650          655

GAG CAT CGG CCG CGC TTC ACG CAT CCG CTT GCC ACG CAA TTC CCG GCC    2016
Glu His Arg Pro Arg Phe Thr His Pro Leu Ala Thr Gln Phe Pro Ala
          660                 665                 670

TGG GCG GGG CTG CTG AAT CCG GCT TCC CGT CCG ATC GGT GGC GAT GGC    2064
Trp Ala Gly Leu Leu Asn Pro Ala Ser Arg Pro Ile Gly Gly Asp Gly
          675                 680                 685

GAT ACC GTG CTG GCC AAC GGG CTC GTC CCG TCA GCC GGG CCG CAG GCG    2112
Asp Thr Val Leu Ala Asn Gly Leu Val Pro Ser Ala Gly Pro Gln Ala
          690                 695                 700

ACC TAT GGT GCC CTG TCG CGC TAC GTC TTC GAT GTC GGC AAT TGG GAC    2160
Thr Tyr Gly Ala Leu Ser Arg Tyr Val Phe Asp Val Gly Asn Trp Asp
          705                 710                 715
```

*FIG. 4J*

```
AAT AGC CGC TGG GTC GTC TTC CAC GGC GCC TCC GGG CAT CCG GCC AGC   2208
Asn Ser Arg Trp Val Val Phe His Gly Ala Ser Gly His Pro Ala Ser
720                 725                 730                 735

GCC CAT TAT GCC GAT CAG AAT GCG CCC TGG AGC GAC TGT GCG ATG GTG   2256
Ala His Tyr Ala Asp Gln Asn Ala Pro Trp Ser Asp Cys Ala Met Val
        740                 745                 750

CCG ATG CTC TAT AGC TGG GAC AGG ATC GCG GCA GAG GCC GTG ACG TCG   2304
Pro Met Leu Tyr Ser Trp Asp Arg Ile Ala Ala Glu Ala Val Thr Ser
        755                 760                 765

CAG GAA CTC GTC CCG GCC TGA                                       2325
Gln Glu Leu Val Pro Ala
770
```

*FIG. 4K*

```
ATG ACT ATG GCA GCT AAT ACG GAT CGC GCG GTC TTG CAG GCG GCG CTG    48
Met Thr Met Ala Ala Asn Thr Asp Arg Ala Val Leu Gln Ala Ala Leu
 -1   1               5                  10                  15

CCG CCG CTT TCC GGC AGC CTC CCC ATT CCC GGA TTG AGC GCG TCG GTC    96
Pro Pro Leu Ser Gly Ser Leu Pro Ile Pro Gly Leu Ser Ala Ser Val
                 20                  25                  30

CGC GTC CGG CGC GAT GCC TGG GGC ATC CCG CAT ATC AAG GCC TCG GGC   144
Arg Val Arg Arg Asp Ala Trp Gly Ile Pro His Ile Lys Ala Ser Gly
                 35                  40                  45

GAG GCC GAT GCC TAT CGG GCG CTG GGC TTC GTC CAT TCG CAG GAC CGT   192
Glu Ala Asp Ala Tyr Arg Ala Leu Gly Phe Val His Ser Gln Asp Arg
                 50                  55                  60

CTT TTC CAG ATG GAG CTG ACG CGT CGC AAG GCG CTG GGA CGC GCG GCC   240
Leu Phe Gln Met Glu Leu Thr Arg Arg Lys Ala Leu Gly Arg Ala Ala
                 65                  70                  75

GAA TGG CTG GGC GCC GCC GAG GCC GAT ATC CTC GTG CGC CGG           288
Glu Trp Leu Gly Ala Ala Glu Ala Asp Ile Leu Val Arg Arg
 80                  85                  90              95
```

*FIG. 5A*

```
CTC GGA ATG GAA AAA GTC TGC CGG CGC GAC TTC GAG GCC TTG GGC GTC      336
Leu Gly Met Glu Lys Val Cys Arg Arg Asp Phe Glu Ala Leu Gly Val
          100                     105                     110

GAG GCG AAG GAC ATG CTG CGG GCT TAT GTC GCC GGC GTG AAC GCA TTC      384
Glu Ala Lys Asp Met Leu Arg Ala Tyr Val Ala Gly Val Asn Ala Phe
          115                     120                     125

CTG GCT TCC GGT GCT CCC CTG CCT GTC GAA TAC GGA TTG CTC GGA GCA      432
Leu Ala Ser Gly Ala Pro Leu Pro Val Glu Tyr Gly Leu Leu Gly Ala
          130                     135                     140

GAG CCG GAG CCC TGG GAG CCT TGG CAC AGC ATC GCG GTG ATG CGC CGG      480
Glu Pro Glu Pro Trp Glu Pro Trp His Ser Ile Ala Val Met Arg Arg
          145                     150                     155

CTG GGC CTG CTT ATG GGT TCG GTG TGG TTC AAG CTC TGG CGG ATG CTG      528
Leu Gly Leu Leu Met Gly Ser Val Trp Phe Lys Leu Trp Arg Met Leu
          160                     165                     170                     175

GCG CTG CCG GTG GTC GGA GCC GCG AAT GCG CTG AAG CTC CGC TAT GAC      576
Ala Leu Pro Val Val Gly Ala Ala Asn Ala Leu Lys Leu Arg Tyr Asp
          180                     185                     190
```

*FIG. 5B*

```
GAT GGC GGC CGG GAT TTG CTC TGC ATC CCG CCG GGC GCC GAA GCC GAT
Asp Gly Gly Arg Asp Leu Leu Cys Ile Pro Pro Gly Ala Glu Ala Asp
        195                 200                 205
```
624

FIG. 5C

| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | 210 | | | | | | 215 | | | | | 220 | | | | |
| CTG | AAG | GCG | ATG | GGC | GGC | GAT | GCC | TCC | GAT | GCT | GCC | GGC | GGC | GGC | AGC | 720 |
| Leu | Lys | Ala | Met | Gly | Gly | Asp | Ala | Ser | Asp | Ala | Ala | Gly | Gly | Gly | Ser | |
| | 225 | | | | 230 | | | | | 235 | | | | | | |
| AAC | AAC | TGG | GCG | GCG | GTC | GCT | CCG | GGC | CGC | ACG | GCG | ACC | GGC | CCG | ATC | 768 |
| Asn | Asn | Trp | Ala | Ala | Val | Ala | Pro | Gly | Arg | Thr | Ala | Thr | Gly | Pro | Ile | |
| 240 | | | | | 245 | | | | | 250 | | | | | 255 | |
| CTC | GCG | GGC | GAT | CCG | CAT | CGC | GTC | TTC | GAA | ATC | CCT | GGC | TAT | TAT | GCG | 816 |
| Leu | Ala | Gly | Asp | Pro | His | Arg | Val | Phe | Glu | Ile | Pro | Gly | Tyr | Tyr | Ala | |
| | | | 260 | | | | | 265 | | | | | | 270 | | |
| CAG | CAT | CAT | CTG | GCC | TGC | GAC | ATG | ATC | GGC | TTC | GAC | CGG | TTC | CTG | ACC | GTG | 864 |
| Gln | His | His | Leu | Ala | Cys | Asp | Met | Ile | Gly | Phe | Asp | Arg | Phe | Leu | Thr | Val |
| | 275 | | | | | | 280 | | | | | 285 | | | | |

| CAG | CAT | CAT | CTG | GCC | TGC | GAC | ATG | ATC | GGC | CTG | ACC | GTG | | | | 864 |
| Gln | His | His | Leu | Ala | Cys | Asp | Met | Ile | Gly | Leu | Thr | Val | | | | |
| | 275 | | | | | | 280 | | | 285 | | | | | | |

| CCG | GGC | GTG | CCG | TTC | CCG | CAC | TTC | GCG | CAT | AAC | GGC | AAG | GTC | GCC | 912 |
| Pro | Gly | Val | Pro | Phe | Pro | His | Phe | Ala | His | Asn | Gly | Lys | Val | Ala | |
| | 290 | | | | 295 | | | | | 300 | | | | | |

*FIG. 5D*

| | | | | | | | | | | | | | | | | |
|---|---|---|---|---|---|---|---|---|---|---|---|---|---|---|---|---|
| TAT | AGC | GTC | ACG | CAT | GCC | TTC | ATG | GAC | ATC | CAC | GAT | CTC | TAT | CTC | GAG | 960 |
| Tyr | Ser | Val | Thr | His | Ala | Phe | Met | Asp | Ile | His | Asp | Leu | Tyr | Leu | Glu | |
| | 305 | | | | | 310 | | | | | 315 | | | | | |
| CAG | TTC | GCG | GGG | GAG | GGC | CGC | ACT | GCG | CGG | TTC | GGC | AAC | GAT | TTC | GAG | 1008 |
| Gln | Phe | Ala | Gly | Glu | Gly | Arg | Thr | Ala | Arg | Phe | Gly | Asn | Asp | Phe | Glu | |
| | 320 | | | | | 325 | | | | | 330 | | | | 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | 340 | | | | | 345 | | | | | | 350 | | |
| CGC | GAG | TTC | GAT | ATC | GTC | GAG | ACT | CGC | GAC | CAT | GGC | CCG | GTT | ATC | GCG | GGC | 1104 |
| Arg | Glu | Phe | Asp | Ile | Val | Glu | Thr | Arg | Asp | His | Gly | Pro | Val | Ile | Ala | Gly |
| | | 355 | | | | | 360 | | | | | 365 | | | | |
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala | |
| | | 370 | | | | 375 | | | | | | 380 | | | | |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser | |
| | 385 | | | | | 390 | | | | | 395 | | | | | |

FIG. 5E

| ACC | GTG | GCC | CAG | CTC | TAC | GAC | GCG | ACG | CGC | GGC | TGG | GGC | CTG | ATC | GAC | 1248 |
|-----|-----|-----|-----|-----|-----|-----|-----|-----|-----|-----|-----|-----|-----|-----|-----|------|
| Thr | Val | Ala | Gln | Leu | Tyr | Asp | Ala | Thr | Arg | Gly | Trp | Gly | Leu | Ile | Asp | |
| 400 | | | | | 405 | | | | 410 | | | | | 415 | | |

*FIG. 5F*

```
CAT AAC CTC GTC GCC GGG GAT GTC GCG GGC TCG ATC GGC CAT CTG GTC    1296
His Asn Leu Val Ala Gly Asp Val Ala Gly Ser Ile Gly His Leu Val
            420             425             430

CGC GCC CGC GTT CCG TCC CGT CCG CGC CAA AAC GGC TGG CTG CCG GTG    1344
Arg Ala Arg Val Pro Ser Arg Pro Arg Gln Asn Gly Trp Leu Pro Val
            435             440             445

CCG GGC TGG TCC CCG GAG CAT GAA CGG CGG ATT CCG CAC GAG            1392
Pro Gly Trp Ser Pro Glu His Glu Arg Arg Ile Pro His Glu
            450             455             460

GCG ATG CCG CGC GTG GTG CCG GGC GGG ATC GTC ATC GTC ACG GCG        1440
Ala Met Pro Arg Val Val Pro Gly Gly Ile Val Ile Val Thr Ala
            465             470             475

AAT AAT CGC GTC GTG GCC GAT GAC CAT CCC GAT TAT CTC TGC ACC GAT    1488
Asn Asn Arg Val Val Ala Asp Asp His Pro Asp Tyr Leu Cys Thr Asp
            480             485             490             495

TGC CAT CCG CCC TAC CGG GCC GAG CGC ATC ATG AAG CGC CTG GTC GCC   1536
Cys His Pro Pro Tyr Arg Ala Glu Arg Ile Met Lys Arg Leu Val Ala
            500             505             510
```

FIG. 5G

```
AAT CCG GCT TTC GCC GTC GAC GAT GCC ATC CAT GCC GAT ACG              1584
Asn Pro Ala Phe Ala Val Asp Asp Ala Ile His Ala Asp Thr
        515                 520             525

CTG TCG CCC CAT GTC GGG TTG CTG CGC AGG CTC GAG GCG CTT GGA          1632
Leu Ser Pro His Val Gly Leu Leu Arg Arg Leu Glu Ala Leu Gly
            530                 535             540

GCC CGC GAC GAC TCC GCG GCC GAA GGG CTG AGG CAG ATG CTC GTC GCC      1680
Ala Arg Asp Asp Ser Ala Ala Glu Gly Leu Arg Gln Met Leu Val Ala
            545                 550             555

TGG GAC GGC CGC ATG GAT GCG GCT TCG GAG GTC GCC TCT GCC TAC AAT      1728
Trp Asp Gly Arg Met Asp Ala Ala Ser Glu Val Ala Ser Ala Tyr Asn
560                 565                 570             575

GCG TTC CGC AGG GCG CTG ACG CGG CTG GTG ACG GAC CGC AGC GGG CTG      1776
Ala Phe Arg Arg Ala Leu Thr Arg Leu Val Thr Asp Arg Ser Gly Leu
            580                 585                 590

GAG CAC GCG ATA TCG CAT CCC TTC GCG GCT GTC GCG CCG GGC GTC TCA      1824
Glu Gln Ala Ile Ser His Pro Phe Ala Ala Val Ala Pro Gly Val Ser
            595                 600                 605
```

*FIG. 5H*

```
CCG CAA GGC CAG GTC TGG TGG GCC GTG CCG ACC CTG CTG CGC GAC GAC    1872
Pro Gln Gly Gln Val Trp Trp Ala Val Pro Thr Leu Leu Arg Asp Asp
    610                 615                 620
```

FIG. 51

```
GAT GCC GGA ATG CTG AAG GGC TGG AGC TGG GAC CAG GCC TTG TCT GAG      1920
Asp Ala Gly Met Leu Lys Gly Trp Ser Trp Asp Gln Ala Leu Ser Glu
625                 630                 635

GCC CTC TCG GTC GCG TCG CAG AAC CTG ACC GGG CGA AGC TGG GGC GAA      1968
Ala Leu Ser Val Ala Ser Gln Asn Leu Thr Gly Arg Ser Trp Gly Glu
        640                 645                 650                 655

GAG CAT CGG CCG CGC TTC ACG CAT CCG CTT GCC CAA TTC CCG GCC          2016
Glu His Arg Pro Arg Phe Thr His Pro Leu Ala Thr Gln Phe Pro Ala
            660                 665                 670

TGG GCG GGG CTG CTG AAT CCG GCT TCC CGT CCG ATC GGT GAT GGC          2064
Trp Ala Gly Leu Leu Asn Pro Ala Ser Arg Pro Ile Gly Asp Gly
675                 680                 685

GAT ACC GTG CTG GCG AAC GGG CTC GTC CCG TCA GCC GGG CCG CAG GCG      2112
Asp Thr Val Leu Ala Asn Gly Leu Val Pro Ser Ala Gly Pro Gln Ala
        690                 695                 700

ACC TAT GGT GCC CTG TCG CGC TAC GTC TTC GAT GTC GGC AAT TGG GAC      2160
Thr Tyr Gly Ala Leu Ser Arg Tyr Val Phe Asp Val Gly Asn Trp Asp
705                 710                 715
```

FIG. 5J

```
AAT AGC CGC TGG GTC TTC CAC GGC GCC TCC GGG CAT CCG GCC AGC    2208
Asn Ser Arg Trp Val Phe His Gly Ala Ser Gly His Pro Ala Ser
720                 725                 730                 735

GCC CAT TAT GCC GAT CAG AAT GCG CCC TGG AGC GAC TGT GCG ATG GTG    2256
Ala His Tyr Ala Asp Gln Asn Ala Pro Trp Ser Asp Cys Ala Met Val
            740                 745                 750

CCG ATG CTC TAT AGC TGG GAC AGG ATC GCG GCA GAG GCC GTG ACG TCG    2304
Pro Met Leu Tyr Ser Trp Asp Arg Ile Ala Ala Glu Ala Val Thr Ser
        755                 760                 765

CAG GAA CTC GTC CCG GCC TGA    2325
Gln Glu Leu Val Pro Ala
770
```

*FIG. 5K*

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 773 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Thr Met Ala Ala Asn Thr Asp Arg Ala Val Leu Gln Ala Ala Leu Pro
  1               5                  10                  15

Pro Leu Ser Gly Ser Leu Pro Ile Pro Gly Leu Ser Ala Ser Val Arg
             20                  25                  30

Val Arg Arg Asp Ala Trp Gly Ile Pro His Ile Lys Ala Ser Gly Glu
         35                  40                  45

Ala Asp Ala Tyr Arg Ala Leu Gly Phe Val His Ser Gln Asp Arg Leu
     50                  55                  60

Phe Gln Met Glu Leu Thr Arg Arg Lys Ala Leu Gly Arg Ala Ala Glu
 65                  70                  75                  80

Trp Leu Gly Ala Glu Ala Ala Glu Ala Asp Ile Leu Val Arg Arg Leu
                 85                  90                  95

Gly Met Glu Lys Val Cys Arg Arg Asp Phe Glu Ala Leu Gly Val Glu
                100                 105                 110

Ala Lys Asp Met Leu Arg Ala Tyr Val Ala Gly Val Asn Ala Phe Leu
            115                 120                 125

Ala Ser Gly Ala Pro Leu Pro Val Glu Tyr Gly Leu Leu Gly Ala Glu
        130                 135                 140

Pro Glu Pro Trp Glu Pro Trp His Ser Ile Ala Val Met Arg Arg Leu
145                 150                 155                 160

Gly Leu Leu Met Gly Ser Val Trp Phe Lys Leu Trp Arg Met Leu Ala
                165                 170                 175

Leu Pro Val Val Gly Ala Ala Asn Ala Leu Lys Leu Arg Tyr Asp Asp
            180                 185                 190

Gly Gly Arg Asp Leu Leu Cys Ile Pro Pro Gly Ala Glu Ala Asp Arg
        195                 200                 205

Leu Glu Ala Asp Leu Ala Thr Leu Arg Pro Ala Val Asp Ala Leu Leu
    210                 215                 220

Lys Ala Met Gly Gly Asp Ala Ser Asp Ala Ala Gly Gly Gly Ser Asn
225                 230                 235                 240

Asn Trp Ala Val Ala Pro Gly Arg Thr Ala Thr Gly Arg Pro Ile Leu
                245                 250                 255

Ala Gly Asp Pro His Arg Val Phe Glu Ile Pro Gly Xaa Tyr Xaa Gln
            260                 265                 270

His His Leu Ala Cys Asp Arg Phe Asp Met Ile Gly Leu Thr Val Pro
        275                 280                 285

Gly Val Pro Gly Phe Pro His Phe Ala His Asn Gly Lys Val Ala Tyr
    290                 295                 300

Xaa Val Thr His Ala Phe Met Asp Ile His Asp Leu Tyr Leu Glu Gln
305                 310                 315                 320
```

```
    Phe Ala Gly Glu Gly Arg Thr Ala Arg Phe Gly Asn Asp Phe Glu Pro
                325                 330                 335

Val Ala Trp Ser Arg Asp Arg Ile Ala Val Arg Gly Gly Ala Asp Arg
                340                 345                 350

Glu Phe Asp Ile Val Glu Thr Arg His Gly Pro Val Ile Ala Gly Asp
                355                 360                 365

Pro Arg Asp Gly Ala Ala Leu Thr Leu Arg Ser Val Gln Phe Ala Glu
                370                 375                 380

Thr Asp Leu Ser Phe Asp Cys Leu Thr Arg Met Pro Gly Ala Ser Thr
    385                 390                 395                 400

Val Ala Gln Leu Tyr Asp Ala Thr Arg Gly Trp Gly Leu Ile Asp His
                    405                 410                 415

Asn Leu Val Ala Gly Asp Val Ala Gly Ser Ile Gly His Leu Val Arg
                420                 425                 430

Ala Arg Val Pro Ser Arg Pro Arg Glu Asn Gly Trp Leu Pro Val Pro
                435                 440                 445

Gly Trp Ser Gly Glu His Glu Trp Arg Gly Trp Ile Pro His Glu Ala
    450                 455                 460

Met Pro Arg Val Ile Asp Pro Pro Gly Gly Ile Ile Val Thr Ala Asn
    465                 470                 475                 480

Asn Arg Val Val Ala Asp Asp His Pro Asp Tyr Leu Cys Thr Asp Cys
                    485                 490                 495

His Pro Pro Tyr Arg Ala Glu Arg Ile Met Lys Arg Leu Val Ala Asn
                500                 505                 510

Pro Ala Phe Ala Val Asp Asp Ala Ala Ile His Ala Asp Thr Leu
                515                 520                 525

Ser Pro His Val Gly Leu Leu Arg Arg Arg Leu Glu Ala Leu Gly Ala
        530                 535                 540

Arg Asp Asp Ser Ala Ala Glu Gly Leu Arg Gln Met Leu Val Ala Trp
    545                 550                 555                 560

Asp Gly Arg Met Asp Ala Ala Ser Glu Val Ala Ser Ala Tyr Asn Ala
                    565                 570                 575

Phe Arg Arg Ala Leu Thr Arg Leu Val Thr Asp Arg Ser Gly Leu Glu
                580                 585                 590

Gln Ala Ile Ser His Pro Phe Ala Ala Val Ala Pro Gly Val Ser Pro
                595                 600                 605

Gln Gly Gln Val Trp Trp Ala Val Pro Thr Leu Leu Arg Asp Asp Asp
        610                 615                 620

Ala Gly Met Leu Lys Gly Trp Ser Trp Asp Gln Ala Leu Ser Glu Ala
    625                 630                 635                 640

Leu Ser Val Ala Ser Gln Asn Leu Thr Gly Arg Ser Trp Gly Glu Glu
                    645                 650                 655

His Arg Pro Arg Phe Thr His Pro Leu Ala Thr Gln Phe Pro Ala Trp
                660                 665                 670

Ala Gly Leu Leu Asn Pro Ala Ser Arg Pro Ile Gly Gly Asp Gly Asp
                675                 680                 685

Thr Val Leu Ala Asn Gly Leu Val Pro Ser Ala Gly Pro Gln Ala Thr
        690                 695                 700

Tyr Gly Ala Leu Ser Arg Tyr Val Phe Asp Val Gly Asn Trp Asp Asn
    705                 710                 715                 720

Ser Arg Trp Val Val Phe His Gly Ala Ser Gly His Pro Ala Ser Ala
                    725                 730                 735

His Tyr Ala Asp Gln Asn Ala Pro Trp Ser Asp Cys Ala Met Val Pro
                740                 745                 750

Met Leu Tyr Ser Trp Asp Arg Ile Ala Ala Glu Ala Val Thr Ser Gln
```

755                           760                           765

Glu  Leu  Val  Pro  Ala
                      770

( 2 ) INFORMATION FOR SEQ ID NO:2:

( i ) SEQUENCE CHARACTERISTICS:
        ( A ) LENGTH: 2325 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2322

( i x ) FEATURE:
        ( A ) NAME/KEY: matpeptide
        ( B ) LOCATION: 4..2322

( x i ) SEQUENCE DESCRIPTION: SEQ ID NO:2:

| ATG | ACT | ATG | GCA | GCT | AAT | ACG | GAT | CGC | GCG | GTC | TTG | CAG | GCG | GCG | CTG | 48 |
| Met | Thr | Met | Ala | Ala | Asn | Thr | Asp | Arg | Ala | Val | Leu | Gln | Ala | Ala | Leu | |
| -1 | 1 | | | | 5 | | | | 10 | | | | | | 15 | |

| CCG | CCG | CTT | TCC | GGC | AGC | CTC | CCC | ATT | CCC | GGA | TTG | AGC | GCG | TCG | GTC | 96 |
| Pro | Pro | Leu | Ser | Gly | Ser | Leu | Pro | Ile | Pro | Gly | Leu | Ser | Ala | Ser | Val | |
| | | | 20 | | | | | 25 | | | | | 30 | | | |

| CGC | GTC | CGG | CGC | GAT | GCC | TGG | GGC | ATC | CCG | CAT | ATC | AAG | GCC | TCG | GGC | 144 |
| Arg | Val | Arg | Arg | Asp | Ala | Trp | Gly | Ile | Pro | His | Ile | Lys | Ala | Ser | Gly | |
| | | | 35 | | | | 40 | | | | | 45 | | | | |

| GAG | GCC | GAT | GCC | TAT | CGG | GCG | CTG | GGC | TTC | GTC | CAT | TCG | CAG | GAC | CGT | 192 |
| Glu | Ala | Asp | Ala | Tyr | Arg | Ala | Leu | Gly | Phe | Val | His | Ser | Gln | Asp | Arg | |
| | | | 50 | | | | 55 | | | | | 60 | | | | |

| CTT | TTC | CAG | ATG | GAG | CTG | ACG | CGT | CGC | AAG | GCG | CTG | GGA | CGC | GCG | GCC | 240 |
| Leu | Phe | Gln | Met | Glu | Leu | Thr | Arg | Arg | Lys | Ala | Leu | Gly | Arg | Ala | Ala | |
| | 65 | | | | | 70 | | | | | 75 | | | | | |

| GAA | TGG | CTG | GGC | GCC | GAG | GCC | GCC | GAG | GCC | GAT | ATC | CTC | GTG | CGC | CGG | 288 |
| Glu | Trp | Leu | Gly | Ala | Glu | Ala | Ala | Glu | Ala | Asp | Ile | Leu | Val | Arg | Arg | |
| 80 | | | | | 85 | | | | | 90 | | | | | 95 | |

| CTC | GGA | ATG | GAA | AAA | GTC | TGC | CGG | CGC | GAC | TTC | GAG | GCC | TTG | GGC | GTC | 336 |
| Leu | Gly | Met | Glu | Lys | Val | Cys | Arg | Arg | Asp | Phe | Glu | Ala | Leu | Gly | Val | |
| | | | | 100 | | | | | 105 | | | | | 110 | | |

| GAG | GCG | AAG | GAC | ATG | CTG | CGG | GCT | TAT | GTC | GCC | GGC | GTG | AAC | GCA | TTC | 384 |
| Glu | Ala | Lys | Asp | Met | Leu | Arg | Ala | Tyr | Val | Ala | Gly | Val | Asn | Ala | Phe | |
| | | | 115 | | | | | 120 | | | | | 125 | | | |

| CTG | GCT | TCC | GGT | GCT | CCC | CTG | CCT | GTC | GAA | TAC | GGA | TTG | CTC | GGA | GCA | 432 |
| Leu | Ala | Ser | Gly | Ala | Pro | Leu | Pro | Val | Glu | Tyr | Gly | Leu | Leu | Gly | Ala | |
| | | | 130 | | | | | 135 | | | | | 140 | | | |

| GAG | CCG | GAG | CCC | TGG | GAG | CCT | TGG | CAC | AGC | ATC | GCG | GTG | ATG | CGC | CGG | 480 |
| Glu | Pro | Glu | Pro | Trp | Glu | Pro | Trp | His | Ser | Ile | Ala | Val | Met | Arg | Arg | |
| | 145 | | | | | 150 | | | | | 155 | | | | | |

| CTG | GGC | CTG | CTT | ATG | GGT | TCG | GTG | TGG | TTC | AAG | CTC | TGG | CGG | ATG | CTG | 528 |
| Leu | Gly | Leu | Leu | Met | Gly | Ser | Val | Trp | Phe | Lys | Leu | Trp | Arg | Met | Leu | |
| 160 | | | | | 165 | | | | | 170 | | | | | 175 | |

| GCG | CTG | CCG | GTG | GTC | GGA | GCC | GCG | AAT | GCG | CTG | AAG | CTG | CGC | TAT | GAC | 576 |
| Ala | Leu | Pro | Val | Val | Gly | Ala | Ala | Asn | Ala | Leu | Lys | Leu | Arg | Tyr | Asp | |
| | | | | 180 | | | | | 185 | | | | | 190 | | |

| GAT | GGC | GGC | CGG | GAT | TTG | CTC | TGC | ATC | CCG | CCG | GGC | GCC | GAA | CGG | GAT | 624 |
| Asp | Gly | Gly | Arg | Asp | Leu | Leu | Cys | Ile | Pro | Pro | Gly | Ala | Glu | Arg | Asp | |
| | | | 195 | | | | | 200 | | | | | 205 | | | |

| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | | | 210 | | | | | 215 | | | | | 220 | | | |

```
CTG AAG GCG ATG GGC GGC GAT GCC TCC GAT GCT GCC GGC GGC GGC AGC              720
Leu Lys Ala Met Gly Gly Asp Ala Ser Asp Ala Ala Gly Gly Gly Ser
    225             230                 235

AAC AAC TGG GCG GTC GCT CCG GGC CGC ACG GCG ACC GGC AGG CCG ATC              768
Asn Asn Trp Ala Val Ala Pro Gly Arg Thr Ala Thr Gly Arg Pro Ile
240             245                 250                 255

CTC GCG GGC GAT CCG CAT CGC GTC TTC GAA ATC CCG GGC ATG TAT GCG              816
Leu Ala Gly Asp Pro His Arg Val Phe Glu Ile Pro Gly Met Tyr Ala
                260                 265                 270

CAG CAT CAT CTG GCC TGC GAC CGG TTC GAC ATG ATC GGC CTG ACC GTG              864
Gln His His Leu Ala Cys Asp Arg Phe Asp Met Ile Gly Leu Thr Val
            275                 280                 285

CCG GGC GTG CCG GGC TTC CCG CAC TTC GCG CAT AAC GGC AAG GTC GCC              912
Pro Gly Val Pro Gly Phe Pro His Phe Ala His Asn Gly Lys Val Ala
        290                 295                 300

TAT AGC GTC ACG CAT GCC TTC ATG GAC ATC CAC GAT CTC TAT CTC GAG              960
Tyr Ser Val Thr His Ala Phe Met Asp Ile His Asp Leu Tyr Leu Glu
    305                 310                 315

CAG TTC GCG GGG GAG GGC CGC ACT GCG CGG TTC GGC AAC GAT TTC GAG             1008
Gln Phe Ala Gly Glu Gly Arg Thr Ala Arg Phe Gly Asn Asp Phe Glu
320             325                 330                 335

CCC GTC GCC TGG AGC CGG GAC CGT ATC GCG GTC CGG GGT GGC GCC GAT             1056
Pro Val Ala Trp Ser Arg Asp Arg Ile Ala Val Arg Gly Gly Ala Asp
                340                 345                 350

CGC GAG TTC GAT ATC GTC GAG ACG CGC CAT GGC CCG GTT ATC GCG GGC             1104
Arg Glu Phe Asp Ile Val Glu Thr Arg His Gly Pro Val Ile Ala Gly
            355                 360                 365

GAT CCG CGC GAT GGC GCA GCG CTC ACG CTG CGT TCG GTC CAG TTC GCC             1152
Asp Pro Arg Asp Gly Ala Ala Leu Thr Leu Arg Ser Val Gln Phe Ala
        370                 375                 380

GAG ACC GAT CTG TCC TTC GAC TGC CTG ACG CGG ATG CCG GGC GCA TCG             1200
Glu Thr Asp Leu Ser Phe Asp Cys Leu Thr Arg Met Pro Gly Ala Ser
    385                 390                 395

ACC GTG GCC CAG CTC TAC GAC GCG ACG CGC GGC TGG GGC CTG ATC GAC             1248
Thr Val Ala Gln Leu Tyr Asp Ala Thr Arg Gly Trp Gly Leu Ile Asp
400             405                 410                 415

CAT AAC CTC GTC GCC GGG GAT GTC GCG GGC TCG ATC GGC CAT CTG GTC             1296
His Asn Leu Val Ala Gly Asp Val Ala Gly Ser Ile Gly His Leu Val
                420                 425                 430

CGC GCC CGC GTT CCG TCC CGT CCG CGC GAA AAC GGC TGG CTG CCG GTG             1344
Arg Ala Arg Val Pro Ser Arg Pro Arg Glu Asn Gly Trp Leu Pro Val
            435                 440                 445

CCG GGC TGG TCC GGC GAG CAT GAA TGG CGG GGC TGG ATT CCG CAC GAG             1392
Pro Gly Trp Ser Gly Glu His Glu Trp Arg Gly Trp Ile Pro His Glu
        450                 455                 460

GCG ATG CCG CGC GTG ATC GAT CCG CCG GGC GGC ATC ATC GTC ACG GCG             1440
Ala Met Pro Arg Val Ile Asp Pro Pro Gly Gly Ile Ile Val Thr Ala
    465                 470                 475

AAT AAT CGC GTC GTG GCC GAT GAC CAT CCC GAT TAT CTC TGC ACC GAT             1488
Asn Asn Arg Val Val Ala Asp Asp His Pro Asp Tyr Leu Cys Thr Asp
480             485                 490                 495

TGC CAT CCG CCC TAC CGC GCC GAG CGC ATC ATG AAG CGC CTG GTC GCC             1536
Cys His Pro Pro Tyr Arg Ala Glu Arg Ile Met Lys Arg Leu Val Ala
                500                 505                 510

AAT CCG GCT TTC GCC GTC GAC GAT GCC GCC GCG ATC CAT GCC GAT ACG             1584
Asn Pro Ala Phe Ala Val Asp Asp Ala Ala Ala Ile His Ala Asp Thr
            515                 520                 525

CTG TCG CCC CAT GTC GGG TTG CTG CGC CGG AGG CTC GAG GCG CTT GGA             1632
Leu Ser Pro His Val Gly Leu Leu Arg Arg Arg Leu Glu Ala Leu Gly
        530                 535                 540

GCC CGC GAC GAC TCC GCG GCC GAA GGG CTG AGG CAG ATG CTC GTC GCC             1680
Ala Arg Asp Asp Ser Ala Ala Glu Gly Leu Arg Gln Met Leu Val Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 545 |     |     |     |     | 550 |     |     |     |     |     | 555 |     |     |     |      |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn |      |
| 560 |     |     |     |     | 565 |     |     |     |     | 570 |     |     |     |     | 575 |      |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu |      |
|     |     |     |     | 580 |     |     |     |     | 585 |     |     |     |     | 590 |     |      |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser |      |
|     |     |     | 595 |     |     |     |     | 600 |     |     |     |     | 605 |     |     |      |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp |      |
|     |     | 610 |     |     |     |     | 615 |     |     |     |     | 620 |     |     |     |      |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu |      |
| 625 |     |     |     |     | 630 |     |     |     |     | 635 |     |     |     |     |     |      |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu |      |
| 640 |     |     |     |     | 645 |     |     |     |     | 650 |     |     |     |     | 655 |      |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala |      |
|     |     |     |     | 660 |     |     |     |     | 665 |     |     |     |     | 670 |     |      |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly |      |
|     |     |     |     | 675 |     |     |     |     | 680 |     |     |     | 685 |     |     |      |
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala |      |
|     |     | 690 |     |     |     |     | 695 |     |     |     |     | 700 |     |     |     |      |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp |      |
|     |     | 705 |     |     |     | 710 |     |     |     |     | 715 |     |     |     |     |      |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser |      |
| 720 |     |     |     |     | 725 |     |     |     |     | 730 |     |     |     |     | 735 |      |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val |      |
|     |     |     |     | 740 |     |     |     |     | 745 |     |     |     |     | 750 |     |      |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser |      |
|     |     |     | 755 |     |     |     |     | 760 |     |     |     |     | 765 |     |     |      |
| CAG | GAA | CTC | GTC | CCG | GCC | TGA |     |     |     |     |     |     |     |     |     | 2325 |
| Gln | Glu | Leu | Val | Pro | Ala |     |     |     |     |     |     |     |     |     |     |      |
|     |     |     | 770 |     |     |     |     |     |     |     |     |     |     |     |     |      |

( 2 ) INFORMATION FOR SEQ ID NO:3:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

|     |     |     |     |     |     |     |     |     |     |     |     |     |     |     |
| --- | --- | --- | --- | --- | --- | --- | --- | --- | --- | --- | --- | --- | --- | --- |
| Met | Thr | Met | Ala | Ala | Asn | Thr | Asp | Arg | Ala | Val | Leu | Gln | Ala | Ala | Leu |
| -1  | 1   |     |     |     | 5   |     |     |     |     | 10  |     |     |     |     | 15  |
| Pro | Pro | Leu | Ser | Gly | Ser | Leu | Pro | Ile | Pro | Gly | Leu | Ser | Ala | Ser | Val |
|     |     |     |     | 20  |     |     |     |     | 25  |     |     |     |     | 30  |     |
| Arg | Val | Arg | Arg | Asp | Ala | Trp | Gly | Ile | Pro | His | Ile | Lys | Ala | Ser | Gly |
|     |     |     |     | 35  |     |     |     |     | 40  |     |     |     |     | 45  |     |
| Glu | Ala | Asp | Ala | Tyr | Arg | Ala | Leu | Gly | Phe | Val | His | Ser | Gln | Asp | Arg |
|     |     |     |     | 50  |     |     |     |     | 55  |     |     |     |     | 60  |     |

-continued

| | | | | | | | | | | | | | | |
|---|---|---|---|---|---|---|---|---|---|---|---|---|---|---|
| Leu | Phe | Gln | Met | Glu | Leu | Thr | Arg | Arg | Lys | Ala | Leu | Gly | Arg | Ala | Ala |
| | 65 | | | | 70 | | | | | 75 | | | | | |
| Glu | Trp | Leu | Gly | Ala | Glu | Ala | Ala | Glu | Ala | Asp | Ile | Leu | Val | Arg | Arg |
| 80 | | | | | 85 | | | | | 90 | | | | | 95 |
| Leu | Gly | Met | Glu | Lys | Val | Cys | Arg | Arg | Asp | Phe | Glu | Ala | Leu | Gly | Val |
| | | | | 100 | | | | | 105 | | | | | 110 | |
| Glu | Ala | Lys | Asp | Met | Leu | Arg | Ala | Tyr | Val | Ala | Gly | Val | Asn | Ala | Phe |
| | | | 115 | | | | | 120 | | | | | 125 | | |
| Leu | Ala | Ser | Gly | Ala | Pro | Leu | Pro | Val | Glu | Tyr | Gly | Leu | Leu | Gly | Ala |
| | | | 130 | | | | 135 | | | | | 140 | | | |
| Glu | Pro | Glu | Pro | Trp | Glu | Pro | Trp | His | Ser | Ile | Ala | Val | Met | Arg | Arg |
| | 145 | | | | | 150 | | | | | 155 | | | | |
| Leu | Gly | Leu | Leu | Met | Gly | Ser | Val | Trp | Phe | Lys | Leu | Trp | Arg | Met | Leu |
| 160 | | | | | 165 | | | | | 170 | | | | | 175 |
| Ala | Leu | Pro | Val | Val | Gly | Ala | Ala | Asn | Ala | Leu | Lys | Leu | Arg | Tyr | Asp |
| | | | | 180 | | | | | 185 | | | | | 190 | |
| Asp | Gly | Gly | Arg | Asp | Leu | Leu | Cys | Ile | Pro | Pro | Gly | Ala | Glu | Arg | Asp |
| | | | 195 | | | | | 200 | | | | | 205 | | |
| Arg | Leu | Glu | Ala | Asp | Leu | Ala | Thr | Leu | Arg | Pro | Ala | Val | Asp | Ala | Leu |
| | | 210 | | | | | 215 | | | | | 220 | | | |
| Leu | Lys | Ala | Met | Gly | Gly | Asp | Ala | Ser | Asp | Ala | Ala | Gly | Gly | Gly | Ser |
| | 225 | | | | | 230 | | | | | 235 | | | | |
| Asn | Asn | Trp | Ala | Val | Ala | Pro | Gly | Arg | Thr | Ala | Thr | Gly | Arg | Pro | Ile |
| 240 | | | | | 245 | | | | | 250 | | | | | 255 |
| Leu | Ala | Gly | Asp | Pro | His | Arg | Val | Phe | Glu | Ile | Pro | Gly | Met | Tyr | Ala |
| | | | | 260 | | | | | 265 | | | | | 270 | |
| Gln | His | His | Leu | Ala | Cys | Asp | Arg | Phe | Asp | Met | Ile | Gly | Leu | Thr | Val |
| | | | 275 | | | | | 280 | | | | | 285 | | |
| Pro | Gly | Val | Pro | Gly | Phe | Pro | His | Phe | Ala | His | Asn | Gly | Lys | Val | Ala |
| | | 290 | | | | | 295 | | | | | 300 | | | |
| Tyr | Ser | Val | Thr | His | Ala | Phe | Met | Asp | Ile | His | Asp | Leu | Tyr | Leu | Glu |
| | 305 | | | | | 310 | | | | | 315 | | | | |
| Gln | Phe | Ala | Gly | Glu | Gly | Arg | Thr | Ala | Arg | Phe | Gly | Asn | Asp | Phe | Glu |
| 320 | | | | | 325 | | | | | 330 | | | | | 335 |
| Pro | Val | Ala | Trp | Ser | Arg | Asp | Arg | Ile | Ala | Val | Arg | Gly | Gly | Ala | Asp |
| | | | | 340 | | | | | 345 | | | | | 350 | |
| Arg | Glu | Phe | Asp | Ile | Val | Glu | Thr | Arg | His | Gly | Pro | Val | Ile | Ala | Gly |
| | | | 355 | | | | | 360 | | | | | 365 | | |
| Asp | Pro | Arg | Asp | Gly | Ala | Ala | Leu | Thr | Leu | Arg | Ser | Val | Gln | Phe | Ala |
| | | 370 | | | | | 375 | | | | | 380 | | | |
| Glu | Thr | Asp | Leu | Ser | Phe | Asp | Cys | Leu | Thr | Arg | Met | Pro | Gly | Ala | Ser |
| | 385 | | | | | 390 | | | | | 395 | | | | |
| Thr | Val | Ala | Gln | Leu | Tyr | Asp | Ala | Thr | Arg | Gly | Trp | Gly | Leu | Ile | Asp |
| 400 | | | | | 405 | | | | | 410 | | | | | 415 |
| His | Asn | Leu | Val | Ala | Gly | Asp | Val | Ala | Gly | Ser | Ile | Gly | His | Leu | Val |
| | | | | 420 | | | | | 425 | | | | | 430 | |
| Arg | Ala | Arg | Val | Pro | Ser | Arg | Pro | Arg | Glu | Asn | Gly | Trp | Leu | Pro | Val |
| | | | 435 | | | | | 440 | | | | | 445 | | |
| Pro | Gly | Trp | Ser | Gly | Glu | His | Glu | Trp | Arg | Gly | Trp | Ile | Pro | His | Glu |
| | | 450 | | | | | 455 | | | | | 460 | | | |
| Ala | Met | Pro | Arg | Val | Ile | Asp | Pro | Pro | Gly | Gly | Ile | Ile | Val | Thr | Ala |
| | 465 | | | | | 470 | | | | | 475 | | | | |
| Asn | Asn | Arg | Val | Val | Ala | Asp | Asp | His | Pro | Asp | Tyr | Leu | Cys | Thr | Asp |
| 480 | | | | | 485 | | | | | 490 | | | | | 495 |
| Cys | His | Pro | Pro | Tyr | Arg | Ala | Glu | Arg | Ile | Met | Lys | Arg | Leu | Val | Ala |

|       |       |       |       | 500   |       |       |       | 505   |       |       |       | 510   |       |       |
|-------|-------|-------|-------|-------|-------|-------|-------|-------|-------|-------|-------|-------|-------|-------|
| Asn   | Pro   | Ala   | Phe   | Ala   | Val   | Asp   | Asp   | Ala   | Ala   | Ile   | His   | Ala   | Asp   | Thr   |
|       |       |       | 515   |       |       |       |       | 520   |       |       |       | 525   |       |       |
| Leu   | Ser   | Pro   | His   | Val   | Gly   | Leu   | Leu   | Arg   | Arg   | Arg   | Leu   | Glu   | Ala   | Leu   | Gly   |
|       |       | 530   |       |       |       | 535   |       |       |       |       | 540   |       |       |       |

Ala Arg Asp Asp Ser Ala Ala Glu Gly Leu Arg Gln Met Leu Val Ala
    545             550                 555

Trp Asp Gly Arg Met Asp Ala Ala Ser Glu Val Ala Ser Ala Tyr Asn
560             565                 570                 575

Ala Phe Arg Arg Ala Leu Thr Arg Leu Val Thr Asp Arg Ser Gly Leu
            580             585                 590

Glu Gln Ala Ile Ser His Pro Phe Ala Ala Val Ala Pro Gly Val Ser
        595             600                 605

Pro Gln Gly Gln Val Trp Trp Ala Val Pro Thr Leu Leu Arg Asp Asp
        610             615                 620

Asp Ala Gly Met Leu Lys Gly Trp Ser Trp Asp Gln Ala Leu Ser Glu
    625             630                 635

Ala Leu Ser Val Ala Ser Gln Asn Leu Thr Gly Arg Ser Trp Gly Glu
640             645                 650                 655

Glu His Arg Pro Arg Phe Thr His Pro Leu Ala Thr Gln Phe Pro Ala
                660             665                 670

Trp Ala Gly Leu Leu Asn Pro Ala Ser Arg Pro Ile Gly Gly Asp Gly
            675             680                 685

Asp Thr Val Leu Ala Asn Gly Leu Val Pro Ser Ala Gly Pro Gln Ala
        690             695                 700

Thr Tyr Gly Ala Leu Ser Arg Tyr Val Phe Asp Val Gly Asn Trp Asp
    705             710                 715

Asn Ser Arg Trp Val Val Phe His Gly Ala Ser Gly His Pro Ala Ser
720             725                 730                 735

Ala His Tyr Ala Asp Gln Asn Ala Pro Trp Ser Asp Cys Ala Met Val
            740                 745                 750

Pro Met Leu Tyr Ser Trp Asp Arg Ile Ala Ala Glu Ala Val Thr Ser
            755             760                 765

Gln Glu Leu Val Pro Ala
            770

( 2 ) INFORMATION FOR SEQ ID NO:4:

( i ) SEQUENCE CHARACTERISTICS:
        ( A ) LENGTH: 2325 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2322

( i x ) FEATURE:
        ( A ) NAME/KEY: matpeptide
        ( B ) LOCATION: 4..2322

( x i ) SEQUENCE DESCRIPTION: SEQ ID NO:4:

ATG ACT ATG GCA GCT AAT ACG GAT CGC GCG GTC TTG CAG GCG GCG CTG    48
Met Thr Met Ala Ala Asn Thr Asp Arg Ala Val Leu Gln Ala Ala Leu
 -1   1             5                  10                  15

CCG CCG CTT TCC GGC AGC CTC CCC ATT CCC GGA TTG AGC GCG TCG GTC    96
Pro Pro Leu Ser Gly Ser Leu Pro Ile Pro Gly Leu Ser Ala Ser Val
            20                  25                  30

| | | | | | | | | | | | | | | | | |
|---|---|---|---|---|---|---|---|---|---|---|---|---|---|---|---|---|
| CGC | GTC | CGG | CGC | GAT | GCC | TGG | GGC | ATC | CCG | CAT | ATC | AAG | GCC | TCG | GGC | 144 |
| Arg | Val | Arg | Arg | Asp | Ala | Trp | Gly | Ile | Pro | His | Ile | Lys | Ala | Ser | Gly | |
| | | 35 | | | | | 40 | | | | | 45 | | | | |
| GAG | GCC | GAT | GCC | TAT | CGG | GCG | CTG | GGC | TTC | GTC | CAT | TCG | CAG | GAC | CGT | 192 |
| Glu | Ala | Asp | Ala | Tyr | Arg | Ala | Leu | Gly | Phe | Val | His | Ser | Gln | Asp | Arg | |
| | | 50 | | | | | 55 | | | | | 60 | | | | |
| CTT | TTC | CAG | ATG | GAG | CTG | ACG | CGT | CGC | AAG | GCG | CTG | GGA | CGC | GCG | GCC | 240 |
| Leu | Phe | Gln | Met | Glu | Leu | Thr | Arg | Arg | Lys | Ala | Leu | Gly | Arg | Ala | Ala | |
| | 65 | | | | | 70 | | | | | 75 | | | | | |
| GAA | TGG | CTG | GGC | GCC | GAG | GCC | GCC | GAG | GCC | GAT | ATC | CTC | GTG | CGC | CGG | 288 |
| Glu | Trp | Leu | Gly | Ala | Glu | Ala | Ala | Glu | Ala | Asp | Ile | Leu | Val | Arg | Arg | |
| 80 | | | | | 85 | | | | | 90 | | | | | 95 | |
| CTC | GGA | ATG | GAA | AAA | GTC | TGC | CGG | CGC | GAC | TTC | GAG | GCC | TTG | GGC | GTC | 336 |
| Leu | Gly | Met | Glu | Lys | Val | Cys | Arg | Arg | Asp | Phe | Glu | Ala | Leu | Gly | Val | |
| | | | | 100 | | | | | 105 | | | | | 110 | | |
| GAG | GCG | AAG | GAC | ATG | CTG | CGG | GCT | TAT | GTC | GCC | GGC | GTG | AAC | GCA | TTC | 384 |
| Glu | Ala | Lys | Asp | Met | Leu | Arg | Ala | Tyr | Val | Ala | Gly | Val | Asn | Ala | Phe | |
| | | | 115 | | | | | 120 | | | | | 125 | | | |
| CTG | GCT | TCC | GGT | GCT | CCC | CTG | CCT | GTC | GAA | TAC | GGA | TTG | CTC | GGA | GCA | 432 |
| Leu | Ala | Ser | Gly | Ala | Pro | Leu | Pro | Val | Glu | Tyr | Gly | Leu | Leu | Gly | Ala | |
| | | | 130 | | | | | 135 | | | | | 140 | | | |
| GAG | CCG | GAG | CCC | TGG | GAG | CCT | TGG | CAC | AGC | ATC | GCG | GTG | ATG | CGC | CGG | 480 |
| Glu | Pro | Glu | Pro | Trp | Glu | Pro | Trp | His | Ser | Ile | Ala | Val | Met | Arg | Arg | |
| | 145 | | | | | 150 | | | | | 155 | | | | | |
| CTG | GGC | CTG | CTT | ATG | GGT | TCG | GTG | TGG | TTC | AAG | CTC | TGG | CGG | ATG | CTG | 528 |
| Leu | Gly | Leu | Leu | Met | Gly | Ser | Val | Trp | Phe | Lys | Leu | Trp | Arg | Met | Leu | |
| 160 | | | | | 165 | | | | | 170 | | | | | 175 | |
| GCG | CTG | CCG | GTG | GTC | GGA | GCC | GCG | AAT | GCG | CTG | AAG | CTG | CGC | TAT | GAC | 576 |
| Ala | Leu | Pro | Val | Val | Gly | Ala | Ala | Asn | Ala | Leu | Lys | Leu | Arg | Tyr | Asp | |
| | | | | 180 | | | | | 185 | | | | | 190 | | |
| GAT | GGC | GGC | CGG | GAT | TTG | CTC | TGC | ATC | CCG | CCG | GGC | GCC | GAA | GCC | GAT | 624 |
| Asp | Gly | Gly | Arg | Asp | Leu | Leu | Cys | Ile | Pro | Pro | Gly | Ala | Glu | Ala | Asp | |
| | | | 195 | | | | | 200 | | | | | 205 | | | |
| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | | 210 | | | | | 215 | | | | | 220 | | | | |
| CTG | AAG | GCG | ATG | GGC | GGC | GAT | GCC | TCC | GAT | GCT | GCC | GGC | GGC | GGC | AGC | 720 |
| Leu | Lys | Ala | Met | Gly | Gly | Asp | Ala | Ser | Asp | Ala | Ala | Gly | Gly | Gly | Ser | |
| | 225 | | | | | 230 | | | | | 235 | | | | | |
| AAC | AAC | TGG | GCG | GTC | GCT | CCG | GGC | CGC | ACG | GCG | ACC | GGC | AGG | CCG | ATC | 768 |
| Asn | Asn | Trp | Ala | Val | Ala | Pro | Gly | Arg | Thr | Ala | Thr | Gly | Arg | Pro | Ile | |
| 240 | | | | | 245 | | | | | 250 | | | | | 255 | |
| CTC | GCG | GGC | GAT | CCG | CAT | CGC | GTC | TTC | GAA | ATC | CCT | GGC | TAT | TAT | GCG | 816 |
| Leu | Ala | Gly | Asp | Pro | His | Arg | Val | Phe | Glu | Ile | Pro | Gly | Tyr | Tyr | Ala | |
| | | | | 260 | | | | | 265 | | | | | 270 | | |
| CAG | CAT | CAT | CTG | GCC | TGC | GAC | CGG | TTC | GAC | ATG | ATC | GGC | CTG | ACC | GTG | 864 |
| Gln | His | His | Leu | Ala | Cys | Asp | Arg | Phe | Asp | Met | Ile | Gly | Leu | Thr | Val | |
| | | | 275 | | | | | 280 | | | | | 285 | | | |
| CCG | GGC | GTG | CCG | GGC | TTC | CCG | CAC | TTC | GCG | CAT | AAC | GGC | AAG | GTC | GCC | 912 |
| Pro | Gly | Val | Pro | Gly | Phe | Pro | His | Phe | Ala | His | Asn | Gly | Lys | Val | Ala | |
| | | 290 | | | | | 295 | | | | | 300 | | | | |
| TAT | TGC | GTC | ACC | CAT | GCC | TTC | ATG | GAC | ATC | CAC | GAT | CTC | TAT | CTC | GAG | 960 |
| Tyr | Cys | Val | Thr | His | Ala | Phe | Met | Asp | Ile | His | Asp | Leu | Tyr | Leu | Glu | |
| | 305 | | | | | 310 | | | | | 315 | | | | | |
| CAG | TTC | GCG | GGG | GAG | GGC | CGC | ACT | GCG | CGG | TTC | GGC | AAC | GAT | TTC | GAG | 1008 |
| Gln | Phe | Ala | Gly | Glu | Gly | Arg | Thr | Ala | Arg | Phe | Gly | Asn | Asp | Phe | Glu | |
| 320 | | | | | 325 | | | | | 330 | | | | | 335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser | Arg | Asp | Arg | Ile | Ala | Val | Arg | Gly | Gly | Ala | Asp | |
| | | | | 340 | | | | | 345 | | | | | 350 | | |
| CGC | GAG | TTC | GAT | ATC | GTC | GAG | ACG | CGC | CAT | GGC | CCG | GTT | ATC | GCG | GGC | 1104 |
| Arg | Glu | Phe | Asp | Ile | Val | Glu | Thr | Arg | His | Gly | Pro | Val | Ile | Ala | Gly | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 355 |     |     |     |     | 360 |     |     |     |     | 365 |     |      |
| GAT | CCG | CGC | GAT | GGC | GCA | GCG | CTC | ACG | CTG | CGT | TCG | GTC | CAG | TTC | GCC | 1152 |
| Asp | Pro | Arg | Asp | Gly | Ala | Ala | Leu | Thr | Leu | Arg | Ser | Val | Gln | Phe | Ala |      |
|     |     | 370 |     |     |     | 375 |     |     |     | 380 |     |     |     |     |     |      |
| GAG | ACC | GAT | CTG | TCC | TTC | GAC | TGC | CTG | ACG | CGG | ATG | CCG | GGC | GCA | TCG | 1200 |
| Glu | Thr | Asp | Leu | Ser | Phe | Asp | Cys | Leu | Thr | Arg | Met | Pro | Gly | Ala | Ser |      |
|     | 385 |     |     |     |     | 390 |     |     |     |     | 395 |     |     |     |     |      |
| CAT | AAC | CTC | GTC | GCC | GGG | GAT | GTC | GCG | GGC | TCG | ATC | GGC | CAT | CTG | GTC | 1248 |
| His | Asn | Leu | Val | Ala | Gly | Asp | Val | Ala | Gly | Ser | Ile | Gly | His | Leu | Val |      |
| 400 |     |     |     |     | 405 |     |     |     |     | 410 |     |     |     |     | 415 |      |
| ACC | GTG | GCC | CAG | CTC | TAC | GAC | GCG | ACG | CGC | GGC | TGG | GGC | CTG | ATC | GAC | 1296 |
| Thr | Val | Ala | Gln | Leu | Tyr | Asp | Ala | Thr | Arg | Gly | Trp | Gly | Leu | Ile | Asp |      |
|     |     |     |     | 420 |     |     |     |     | 425 |     |     |     |     | 430 |     |      |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro | Ser | Arg | Pro | Arg | Glu | Asn | Gly | Trp | Leu | Pro | Val |      |
|     |     |     | 435 |     |     |     |     | 440 |     |     |     |     | 445 |     |     |      |
| CCG | GGC | TGG | TCC | GGC | GAG | CAT | GAA | TGG | CGG | GGC | TGG | ATT | CCG | CAC | GAG | 1392 |
| Pro | Gly | Trp | Ser | Gly | Glu | His | Glu | Trp | Arg | Gly | Trp | Ile | Pro | His | Glu |      |
|     |     |     | 450 |     |     |     |     | 455 |     |     |     |     | 460 |     |     |      |
| GCG | ATG | CCG | CGC | GTG | ATC | GAT | CCG | CCG | GGC | GGC | ATC | ATC | GTC | ACG | GCG | 1440 |
| Ala | Met | Pro | Arg | Val | Ile | Asp | Pro | Pro | Gly | Gly | Ile | Ile | Val | Thr | Ala |      |
|     | 465 |     |     |     |     | 470 |     |     |     |     | 475 |     |     |     |     |      |
| AAT | AAT | CGC | GTC | GTG | GCC | GAT | GAC | CAT | CCC | GAT | TAT | CTC | TGC | ACC | GAT | 1488 |
| Asn | Asn | Arg | Val | Val | Ala | Asp | Asp | His | Pro | Asp | Tyr | Leu | Cys | Thr | Asp |      |
| 480 |     |     |     |     | 485 |     |     |     |     | 490 |     |     |     |     | 495 |      |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr | Arg | Ala | Glu | Arg | Ile | Met | Lys | Arg | Leu | Val | Ala |      |
|     |     |     | 500 |     |     |     |     | 505 |     |     |     |     | 510 |     |     |      |
| AAT | CCG | GCT | TTC | GCC | GTC | GAC | GAT | GCC | GCC | GCG | ATC | CAT | GCC | GAT | ACG | 1584 |
| Asn | Pro | Ala | Phe | Ala | Val | Asp | Asp | Ala | Ala | Ala | Ile | His | Ala | Asp | Thr |      |
|     |     |     | 515 |     |     |     |     | 520 |     |     |     |     | 525 |     |     |      |
| CTG | TCG | CCC | CAT | GTC | GGG | TTG | CTG | CGC | CGG | AGG | CTC | GAG | GCG | CTT | GGA | 1632 |
| Leu | Ser | Pro | His | Val | Gly | Leu | Leu | Arg | Arg | Arg | Leu | Glu | Ala | Leu | Gly |      |
|     |     | 530 |     |     |     |     | 535 |     |     |     |     | 540 |     |     |     |      |
| GCC | CGC | GAC | GAC | TCC | GCG | GCC | GAA | GGG | CTG | AGG | CAG | ATG | CTC | GTC | GCC | 1680 |
| Ala | Arg | Asp | Asp | Ser | Ala | Ala | Glu | Gly | Leu | Arg | Gln | Met | Leu | Val | Ala |      |
|     | 545 |     |     |     |     | 550 |     |     |     |     | 555 |     |     |     |     |      |
| TGG | GAC | GGC | CGC | ATG | GAT | GCG | GCT | TCG | GAG | GTC | GCG | TCT | GCC | TAC | AAT | 1728 |
| Trp | Asp | Gly | Arg | Met | Asp | Ala | Ala | Ser | Glu | Val | Ala | Ser | Ala | Tyr | Asn |      |
| 560 |     |     |     |     | 565 |     |     |     |     | 570 |     |     |     |     | 575 |      |
| GCG | TTC | CGC | AGG | GCG | CTG | ACG | CGG | CTG | GTG | ACG | GAC | CGC | AGC | GGG | CTG | 1776 |
| Ala | Phe | Arg | Arg | Ala | Leu | Thr | Arg | Leu | Val | Thr | Asp | Arg | Ser | Gly | Leu |      |
|     |     |     |     | 580 |     |     |     |     | 585 |     |     |     |     | 590 |     |      |
| GAG | CAG | GCG | ATA | TCG | CAT | CCC | TTC | GCG | GCT | GTC | GCG | CCG | GGC | GTC | TCA | 1824 |
| Glu | Gln | Ala | Ile | Ser | His | Pro | Phe | Ala | Ala | Val | Ala | Pro | Gly | Val | Ser |      |
|     |     |     | 595 |     |     |     |     | 600 |     |     |     |     | 605 |     |     |      |
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp |      |
|     |     | 610 |     |     |     |     | 615 |     |     |     |     | 620 |     |     |     |      |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu |      |
|     | 625 |     |     |     |     | 630 |     |     |     |     | 635 |     |     |     |     |      |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu |      |
| 640 |     |     |     |     | 645 |     |     |     |     | 650 |     |     |     |     | 655 |      |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala |      |
|     |     |     | 660 |     |     |     |     | 665 |     |     |     |     | 670 |     |     |      |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly |      |
|     |     | 675 |     |     |     |     | 680 |     |     |     |     | 685 |     |     |     |      |

```
GAT  ACC  GTG  CTG  GCG  AAC  GGG  CTC  GTC  CCG  TCA  GCC  GGG  CCG  CAG  GCG   2112
Asp  Thr  Val  Leu  Ala  Asn  Gly  Leu  Val  Pro  Ser  Ala  Gly  Pro  Gln  Ala
          690                 695                      700

ACC  TAT  GGT  GCC  CTG  TCG  CGC  TAC  GTC  TTC  GAT  GTC  GGC  AAT  TGG  GAC   2160
Thr  Tyr  Gly  Ala  Leu  Ser  Arg  Tyr  Val  Phe  Asp  Val  Gly  Asn  Trp  Asp
          705                 710                      715

AAT  AGC  CGC  TGG  GTC  GTC  TTC  CAC  GGC  GCC  TCC  GGG  CAT  CCG  GCC  AGC   2208
Asn  Ser  Arg  Trp  Val  Val  Phe  His  Gly  Ala  Ser  Gly  His  Pro  Ala  Ser
720                           725                      730                 735

GCC  CAT  TAT  GCC  GAT  CAG  AAT  GCG  CCC  TGG  AGC  GAC  TGT  GCG  ATG  GTG   2256
Ala  His  Tyr  Ala  Asp  Gln  Asn  Ala  Pro  Trp  Ser  Asp  Cys  Ala  Met  Val
                    740                      745                 750

CCG  ATG  CTC  TAT  AGC  TGG  GAC  AGG  ATC  GCG  GCA  GAG  GCC  GTG  ACG  TCG   2304
Pro  Met  Leu  Tyr  Ser  Trp  Asp  Arg  Ile  Ala  Ala  Glu  Ala  Val  Thr  Ser
               755                      760                 765

CAG  GAA  CTC  GTC  CCG  GCC  TGA                                                 2325
Gln  Glu  Leu  Val  Pro  Ala
770
```

( 2 ) INFORMATION FOR SEQ ID NO:5:

( i ) SEQUENCE CHARACTERISTICS:
( A ) LENGTH: 774 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Met  Thr  Met  Ala  Ala  Asn  Thr  Asp  Arg  Ala  Val  Leu  Gln  Ala  Ala  Leu
-1   1                   5                    10                        15

Pro  Pro  Leu  Ser  Gly  Ser  Leu  Pro  Ile  Pro  Gly  Leu  Ser  Ala  Ser  Val
                    20                   25                        30

Arg  Val  Arg  Arg  Asp  Ala  Trp  Gly  Ile  Pro  His  Ile  Lys  Ala  Ser  Gly
               35                   40                        45

Glu  Ala  Asp  Ala  Tyr  Arg  Ala  Leu  Gly  Phe  Val  His  Ser  Gln  Asp  Arg
          50                    55                        60

Leu  Phe  Gln  Met  Glu  Leu  Thr  Arg  Arg  Lys  Ala  Leu  Gly  Arg  Ala  Ala
     65                    70                   75

Glu  Trp  Leu  Gly  Ala  Glu  Ala  Ala  Glu  Ala  Asp  Ile  Leu  Val  Arg  Arg
80                       85                   90                        95

Leu  Gly  Met  Glu  Lys  Val  Cys  Arg  Arg  Asp  Phe  Glu  Ala  Leu  Gly  Val
               100                  105                      110

Glu  Ala  Lys  Asp  Met  Leu  Arg  Ala  Tyr  Val  Ala  Gly  Val  Asn  Ala  Phe
          115                  120                      125

Leu  Ala  Ser  Gly  Ala  Pro  Leu  Pro  Val  Glu  Tyr  Gly  Leu  Leu  Gly  Ala
          130                  135                      140

Glu  Pro  Glu  Pro  Trp  Glu  Pro  Trp  His  Ser  Ile  Ala  Val  Met  Arg  Arg
     145                  150                      155

Leu  Gly  Leu  Leu  Met  Gly  Ser  Val  Trp  Phe  Lys  Leu  Trp  Arg  Met  Leu
160                       165                  170                      175

Ala  Leu  Pro  Val  Val  Gly  Ala  Ala  Asn  Ala  Leu  Lys  Leu  Arg  Tyr  Asp
                    180                  185                      190

Asp  Gly  Gly  Arg  Asp  Leu  Leu  Cys  Ile  Pro  Pro  Gly  Ala  Glu  Ala  Asp
               195                  200                      205

Arg  Leu  Glu  Ala  Asp  Leu  Ala  Thr  Leu  Arg  Pro  Ala  Val  Asp  Ala  Leu
          210                  215                      220

Leu  Lys  Ala  Met  Gly  Gly  Asp  Ala  Ser  Asp  Ala  Ala  Gly  Gly  Gly  Ser
     225                  230                       235

Asn  Asn  Trp  Ala  Val  Ala  Pro  Gly  Arg  Thr  Ala  Thr  Gly  Arg  Pro  Ile
```

|     |     |     |     |     |     |     |     |     |     |     |     |     |     |     |
| --- | --- | --- | --- | --- | --- | --- | --- | --- | --- | --- | --- | --- | --- | --- |
| 240 |     |     |     |     | 245 |     |     |     |     | 250 |     |     |     | 255 |
| Leu | Ala | Gly | Asp | Pro | His | Arg | Val | Phe | Glu | Ile | Pro | Gly | Tyr | Tyr | Ala |
|     |     |     |     | 260 |     |     |     |     | 265 |     |     |     | 270 |     |
| Gln | His | His | Leu | Ala | Cys | Asp | Arg | Phe | Asp | Met | Ile | Gly | Leu | Thr | Val |
|     |     |     |     | 275 |     |     |     | 280 |     |     |     |     | 285 |     |
| Pro | Gly | Val | Pro | Gly | Phe | Pro | His | Phe | Ala | His | Asn | Gly | Lys | Val | Ala |
|     |     |     | 290 |     |     |     |     | 295 |     |     |     |     | 300 |     |
| Tyr | Cys | Val | Thr | His | Ala | Phe | Met | Asp | Ile | His | Asp | Leu | Tyr | Leu | Glu |
|     |     | 305 |     |     |     |     | 310 |     |     |     |     | 315 |     |     |
| Gln | Phe | Ala | Gly | Glu | Gly | Arg | Thr | Ala | Arg | Phe | Gly | Asn | Asp | Phe | Glu |
|     |     | 320 |     |     |     |     | 325 |     |     |     | 330 |     |     |     | 335 |
| Pro | Val | Ala | Trp | Ser | Arg | Asp | Arg | Ile | Ala | Val | Arg | Gly | Gly | Ala | Asp |
|     |     |     |     | 340 |     |     |     |     | 345 |     |     |     | 350 |     |
| Arg | Glu | Phe | Asp | Ile | Val | Glu | Thr | Arg | His | Gly | Pro | Val | Ile | Ala | Gly |
|     |     |     | 355 |     |     |     |     | 360 |     |     |     |     | 365 |     |
| Asp | Pro | Arg | Asp | Gly | Ala | Ala | Leu | Thr | Leu | Arg | Ser | Val | Gln | Phe | Ala |
|     |     | 370 |     |     |     |     | 375 |     |     |     |     | 380 |     |     |
| Glu | Thr | Asp | Leu | Ser | Phe | Asp | Cys | Leu | Thr | Arg | Met | Pro | Gly | Ala | Ser |
|     | 385 |     |     |     |     | 390 |     |     |     |     | 395 |     |     |     |
| His | Asn | Leu | Val | Ala | Gly | Asp | Val | Ala | Gly | Ser | Ile | Gly | His | Leu | Val |
| 400 |     |     |     |     | 405 |     |     |     |     | 410 |     |     |     | 415 |
| Thr | Val | Ala | Gln | Leu | Tyr | Asp | Ala | Thr | Arg | Gly | Trp | Gly | Leu | Ile | Asp |
|     |     |     |     | 420 |     |     |     |     | 425 |     |     |     | 430 |     |
| Arg | Ala | Arg | Val | Pro | Ser | Arg | Pro | Arg | Glu | Asn | Gly | Trp | Leu | Pro | Val |
|     |     |     | 435 |     |     |     |     | 440 |     |     |     | 445 |     |     |
| Pro | Gly | Trp | Ser | Gly | Glu | His | Glu | Trp | Arg | Gly | Trp | Ile | Pro | His | Glu |
|     |     |     | 450 |     |     |     | 455 |     |     |     |     | 460 |     |     |
| Ala | Met | Pro | Arg | Val | Ile | Asp | Pro | Pro | Gly | Gly | Ile | Ile | Val | Thr | Ala |
|     | 465 |     |     |     |     | 470 |     |     |     |     | 475 |     |     |     |
| Asn | Asn | Arg | Val | Val | Ala | Asp | Asp | His | Pro | Asp | Tyr | Leu | Cys | Thr | Asp |
| 480 |     |     |     | 485 |     |     |     |     | 490 |     |     |     |     | 495 |
| Cys | His | Pro | Pro | Tyr | Arg | Ala | Glu | Arg | Ile | Met | Lys | Arg | Leu | Val | Ala |
|     |     |     |     | 500 |     |     |     |     | 505 |     |     |     | 510 |     |
| Asn | Pro | Ala | Phe | Ala | Val | Asp | Asp | Ala | Ala | Ala | Ile | His | Ala | Asp | Thr |
|     |     |     |     | 515 |     |     |     |     | 520 |     |     |     | 525 |     |
| Leu | Ser | Pro | His | Val | Gly | Leu | Leu | Arg | Arg | Arg | Leu | Glu | Ala | Leu | Gly |
|     |     | 530 |     |     |     |     | 535 |     |     |     |     | 540 |     |     |
| Ala | Arg | Asp | Asp | Ser | Ala | Ala | Glu | Gly | Leu | Arg | Gln | Met | Leu | Val | Ala |
|     | 545 |     |     |     |     | 550 |     |     |     |     | 555 |     |     |     |
| Trp | Asp | Gly | Arg | Met | Asp | Ala | Ala | Ser | Glu | Val | Ala | Ser | Ala | Tyr | Asn |
| 560 |     |     |     |     | 565 |     |     |     |     | 570 |     |     |     | 575 |
| Ala | Phe | Arg | Arg | Ala | Leu | Thr | Arg | Leu | Val | Thr | Asp | Arg | Ser | Gly | Leu |
|     |     |     |     | 580 |     |     |     |     | 585 |     |     |     | 590 |     |
| Glu | Gln | Ala | Ile | Ser | His | Pro | Phe | Ala | Ala | Val | Ala | Pro | Gly | Val | Ser |
|     |     |     | 595 |     |     |     |     | 600 |     |     |     |     | 605 |     |
| Pro | Gln | Gly | Gln | Val | Trp | Trp | Ala | Val | Pro | Thr | Leu | Leu | Arg | Asp | Asp |
|     |     |     | 610 |     |     |     |     | 615 |     |     |     | 620 |     |     |
| Asp | Ala | Gly | Met | Leu | Lys | Gly | Trp | Ser | Trp | Asp | Gln | Ala | Leu | Ser | Glu |
|     | 625 |     |     |     |     | 630 |     |     |     |     | 635 |     |     |     |
| Ala | Leu | Ser | Val | Ala | Ser | Gln | Asn | Leu | Thr | Gly | Arg | Ser | Trp | Gly | Glu |
| 640 |     |     |     |     | 645 |     |     |     |     | 650 |     |     |     | 655 |
| Glu | His | Arg | Pro | Arg | Phe | Thr | His | Pro | Leu | Ala | Thr | Gln | Phe | Pro | Ala |
|     |     |     |     | 660 |     |     |     |     | 665 |     |     |     | 670 |     |
| Trp | Ala | Gly | Leu | Leu | Asn | Pro | Ala | Ser | Arg | Pro | Ile | Gly | Gly | Asp | Gly |
|     |     |     |     | 675 |     |     |     |     | 680 |     |     |     | 685 |     |

```
Asp Thr Val Leu Ala Asn Gly Leu Val Pro Ser Ala Gly Pro Gln Ala
        690                     695                     700

Thr Tyr Gly Ala Leu Ser Arg Tyr Val Phe Asp Val Gly Asn Trp Asp
    705                     710                     715

Asn Ser Arg Trp Val Val Phe His Gly Ala Ser Gly His Pro Ala Ser
720                     725                     730                     735

Ala His Tyr Ala Asp Gln Asn Ala Pro Trp Ser Asp Cys Ala Met Val
            740                     745                     750

Pro Met Leu Tyr Ser Trp Asp Arg Ile Ala Ala Glu Ala Val Thr Ser
                755                     760                     765

Gln Glu Leu Val Pro Ala
            770
```

(2) INFORMATION FOR SEQ ID NO:6:

(i) SEQUENCE CHARACTERISTICS:
        (A) LENGTH: 773 amino acids
        (B) TYPE: amino acid
        (D) TOPOLOGY: linear (ii) MOLECULE TYPE: protein (xi) SEQUENCE DESCRIPTION: SEQ ID NO:6:

```
Thr Met Ala Ala Asn Thr Asp Arg Ala Val Leu Gln Ala Ala Leu Pro
1                   5                   10                  15

Pro Leu Ser Gly Ser Leu Pro Ile Pro Gly Leu Ser Ala Ser Val Arg
                20                  25                  30

Val Arg Arg Asp Ala Trp Gly Ile Pro His Ile Lys Ala Ser Gly Glu
            35                  40                  45

Ala Asp Ala Tyr Arg Ala Leu Gly Phe Val His Ser Gln Asp Arg Leu
        50                  55                  60

Phe Gln Met Glu Leu Thr Arg Arg Lys Ala Leu Gly Arg Ala Ala Glu
65                  70                  75                  80

Trp Leu Gly Ala Glu Ala Ala Glu Ala Asp Ile Leu Val Arg Arg Leu
                85                  90                  95

Gly Met Glu Lys Val Cys Arg Arg Asp Phe Glu Ala Leu Gly Val Glu
                100                 105                 110

Ala Lys Asp Met Leu Arg Ala Tyr Val Ala Gly Val Asn Ala Phe Leu
        115                 120                 125

Ala Ser Gly Ala Pro Leu Pro Val Glu Tyr Gly Leu Leu Gly Ala Glu
    130                 135                 140

Pro Glu Pro Trp Glu Pro Trp His Ser Ile Ala Val Met Arg Arg Leu
145                 150                 155                 160

Gly Leu Leu Met Gly Ser Val Trp Phe Lys Leu Trp Arg Met Leu Ala
                165                 170                 175

Leu Pro Val Val Gly Ala Ala Asn Ala Leu Lys Leu Arg Tyr Asp Asp
                180                 185                 190

Gly Gly Arg Asp Leu Leu Cys Ile Pro Pro Gly Ala Glu Ala Asp Arg
        195                 200                 205

Leu Glu Ala Asp Leu Ala Thr Leu Arg Pro Ala Val Asp Ala Leu Leu
    210                 215                 220

Lys Ala Met Gly Gly Asp Ala Ser Asp Ala Ala Gly Gly Gly Ser Asn
225                 230                 235                 240

Asn Trp Ala Val Ala Pro Gly Arg Thr Ala Thr Gly Arg Pro Ile Leu
                245                 250                 255

Ala Gly Asp Pro His Arg Val Phe Glu Ile Pro Gly Thr Tyr Ala Gln
                260                 265                 270
```

-continued

| | | | | | | | | | | | | | | |
|---|---|---|---|---|---|---|---|---|---|---|---|---|---|---|
| His | His | Leu | Ala | Cys | Asp | Arg | Phe | Asp | Met | Ile | Gly | Leu | Thr | Val | Pro |
| | 275 | | | | 280 | | | | 285 | | | | | |
| Gly | Val | Pro | Gly | Phe | Pro | His | Phe | Ala | His | Asn | Gly | Lys | Val | Ala | Tyr |
| | 290 | | | | 295 | | | | 300 | | | | | |
| Cys | Val | Thr | His | Ala | Phe | Met | Asp | Ile | His | Asp | Leu | Tyr | Leu | Glu | Gln |
| 305 | | | | | 310 | | | | 315 | | | | | 320 |
| Phe | Ala | Gly | Glu | Gly | Arg | Thr | Ala | Arg | Phe | Gly | Asn | Asp | Phe | Glu | Pro |
| | | | | 325 | | | | 330 | | | | | 335 | |
| Val | Ala | Trp | Ser | Arg | Asp | Arg | Ile | Ala | Val | Arg | Gly | Gly | Ala | Asp | Arg |
| | | | 340 | | | | 345 | | | | | 350 | | |
| Glu | Phe | Asp | Ile | Val | Glu | Thr | Arg | His | Gly | Pro | Val | Ile | Ala | Gly | Asp |
| | | 355 | | | | 360 | | | | | 365 | | | |
| Pro | Arg | Asp | Gly | Ala | Ala | Leu | Thr | Leu | Arg | Ser | Val | Gln | Phe | Ala | Glu |
| | 370 | | | | 375 | | | | 380 | | | | | |
| Thr | Asp | Leu | Ser | Phe | Asp | Cys | Leu | Thr | Arg | Met | Pro | Gly | Ala | Ser | Thr |
| 385 | | | | | 390 | | | | 395 | | | | | 400 |
| Val | Ala | Gln | Leu | Tyr | Asp | Ala | Thr | Arg | Gly | Trp | Gly | Leu | Ile | Asp | His |
| | | | | 405 | | | | | 410 | | | | | 415 |
| Asn | Leu | Val | Ala | Gly | Asp | Val | Ala | Gly | Ser | Ile | Gly | His | Leu | Val | Arg |
| | | | 420 | | | | | 425 | | | | | 430 | |
| Ala | Arg | Val | Pro | Ser | Arg | Pro | Arg | Glu | Asn | Gly | Trp | Leu | Pro | Val | Pro |
| | | | 435 | | | | 440 | | | | | 445 | | |
| Gly | Trp | Ser | Gly | Glu | His | Glu | Trp | Arg | Gly | Trp | Ile | Pro | His | Glu | Ala |
| | 450 | | | | | 455 | | | | | 460 | | | |
| Met | Pro | Arg | Val | Ile | Asp | Pro | Pro | Gly | Gly | Ile | Ile | Val | Thr | Ala | Asn |
| 465 | | | | | 470 | | | | 475 | | | | | 480 |
| Asn | Arg | Val | Val | Ala | Asp | Asp | His | Pro | Asp | Tyr | Leu | Cys | Thr | Asp | Cys |
| | | | | 485 | | | | 490 | | | | | 495 | |
| His | Pro | Pro | Tyr | Arg | Ala | Glu | Arg | Ile | Met | Lys | Arg | Leu | Val | Ala | Asn |
| | | | 500 | | | | | 505 | | | | | 510 | |
| Pro | Ala | Phe | Ala | Val | Asp | Asp | Ala | Ala | Ile | His | Ala | Asp | Thr | Leu |
| | | 515 | | | | 520 | | | | 525 | | | | |
| Ser | Pro | His | Val | Gly | Leu | Leu | Arg | Arg | Arg | Leu | Glu | Ala | Leu | Gly | Ala |
| | 530 | | | | 535 | | | | 540 | | | | | |
| Arg | Asp | Asp | Ser | Ala | Ala | Glu | Gly | Leu | Arg | Gln | Met | Leu | Val | Ala | Trp |
| 545 | | | | 550 | | | | | 555 | | | | | 560 |
| Asp | Gly | Arg | Met | Asp | Ala | Ala | Ser | Glu | Val | Ala | Ser | Ala | Tyr | Asn | Ala |
| | | | | 565 | | | | 570 | | | | | 575 | |
| Phe | Arg | Arg | Ala | Leu | Thr | Arg | Leu | Val | Thr | Asp | Arg | Ser | Gly | Leu | Glu |
| | | | 580 | | | | 585 | | | | 590 | | | |
| Gln | Ala | Ile | Ser | His | Pro | Phe | Ala | Val | Ala | Pro | Gly | Val | Ser | Pro |
| | | 595 | | | | 600 | | | | 605 | | | | |
| Gln | Gly | Gln | Val | Trp | Trp | Ala | Val | Pro | Thr | Leu | Leu | Arg | Asp | Asp | Asp |
| 610 | | | | | 615 | | | | 620 | | | | | |
| Ala | Gly | Met | Leu | Lys | Gly | Trp | Ser | Trp | Asp | Gln | Ala | Leu | Ser | Glu | Ala |
| 625 | | | | 630 | | | | 635 | | | | | | 640 |
| Leu | Ser | Val | Ala | Ser | Gln | Asn | Leu | Thr | Gly | Arg | Ser | Trp | Gly | Glu | Glu |
| | | | | 645 | | | | 650 | | | | | 655 | |
| His | Arg | Pro | Arg | Phe | Thr | His | Pro | Leu | Ala | Thr | Gln | Phe | Pro | Ala | Trp |
| | | | 660 | | | | 665 | | | | 670 | | | |
| Ala | Gly | Leu | Leu | Asn | Pro | Ala | Ser | Arg | Pro | Ile | Gly | Gly | Asp | Gly | Asp |
| | | 675 | | | | 680 | | | | | 685 | | | |
| Thr | Val | Leu | Ala | Asn | Gly | Leu | Val | Pro | Ser | Ala | Gly | Pro | Gln | Ala | Thr |
| | 690 | | | | 695 | | | | | 700 | | | | |
| Tyr | Gly | Ala | Leu | Ser | Arg | Tyr | Val | Phe | Asp | Val | Gly | Asn | Trp | Asp | Asn |

```
                705                  710                  715                  720
          Ser  Arg  Trp  Val  Val  Phe  His  Gly  Ala  Ser  Gly  His  Pro  Ala  Ser  Ala
                              725                  730                  735

His  Tyr  Ala  Asp  Gln  Asn  Ala  Pro  Trp  Ser  Asp  Cys  Ala  Met  Val  Pro
                         740                       745                  750

Met  Leu  Tyr  Ser  Trp  Asp  Arg  Ile  Ala  Ala  Glu  Ala  Val  Thr  Ser  Gln
                    755                       760                       765

Glu  Leu  Val  Pro  Ala
                    770
```

( 2 ) INFORMATION FOR SEQ ID NO:7:

( i ) SEQUENCE CHARACTERISTICS:
        ( A ) LENGTH: 2325 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2322

( i x ) FEATURE:
        ( A ) NAME/KEY: matpeptide
        ( B ) LOCATION: 4..2322

( x i ) SEQUENCE DESCRIPTION: SEQ ID NO:7:

```
ATG  ACT  ATG  GCA  GCT  AAT  ACG  GAT  CGC  GCG  GTC  TTG  CAG  GCG  GCG  CTG        48
Met  Thr  Met  Ala  Ala  Asn  Thr  Asp  Arg  Ala  Val  Leu  Gln  Ala  Ala  Leu
 -1   1                   5                        10                       15

CCG  CCG  CTT  TCC  GGC  AGC  CTC  CCC  ATT  CCC  GGA  TTG  AGC  GCG  TCG  GTC        96
Pro  Pro  Leu  Ser  Gly  Ser  Leu  Pro  Ile  Pro  Gly  Leu  Ser  Ala  Ser  Val
                         20                        25                       30

CGC  GTC  CGG  CGC  GAT  GCC  TGG  GGC  ATC  CCG  CAT  ATC  AAG  GCC  TCG  GGC       144
Arg  Val  Arg  Arg  Asp  Ala  Trp  Gly  Ile  Pro  His  Ile  Lys  Ala  Ser  Gly
                35                        40                       45

GAG  GCC  GAT  GCC  TAT  CGG  GCG  CTG  GGC  TTC  GTC  CAT  TCG  CAG  GAC  CGT       192
Glu  Ala  Asp  Ala  Tyr  Arg  Ala  Leu  Gly  Phe  Val  His  Ser  Gln  Asp  Arg
          50                        55                       60

CTT  TTC  CAG  ATG  GAG  CTG  ACG  CGT  CGC  AAG  GCG  CTG  GGA  CGC  GCG  GCC       240
Leu  Phe  Gln  Met  Glu  Leu  Thr  Arg  Arg  Lys  Ala  Leu  Gly  Arg  Ala  Ala
     65                        70                       75

GAA  TGG  CTG  GGC  GCC  GAG  GCC  GCC  GAG  GCC  GAT  ATC  CTC  GTG  CGC  CGG       288
Glu  Trp  Leu  Gly  Ala  Glu  Ala  Ala  Glu  Ala  Asp  Ile  Leu  Val  Arg  Arg
 80                        85                       90                       95

CTC  GGA  ATG  GAA  AAA  GTC  TGC  CGG  CGC  GAC  TTC  GAG  GCC  TTG  GGC  GTC       336
Leu  Gly  Met  Glu  Lys  Val  Cys  Arg  Arg  Asp  Phe  Glu  Ala  Leu  Gly  Val
                    100                      105                      110

GAG  GCG  AAG  GAC  ATG  CTG  CGG  GCT  TAT  GTC  GCC  GGC  GTG  AAC  GCA  TTC       384
Glu  Ala  Lys  Asp  Met  Leu  Arg  Ala  Tyr  Val  Ala  Gly  Val  Asn  Ala  Phe
               115                      120                      125

CTG  GCT  TCC  GGT  GCT  CCC  CTG  CCT  GTC  GAA  TAC  GGA  TTG  CTC  GGA  GCA       432
Leu  Ala  Ser  Gly  Ala  Pro  Leu  Pro  Val  Glu  Tyr  Gly  Leu  Leu  Gly  Ala
          130                      135                      140

GAG  CCG  GAG  CCC  TGG  GAG  CCT  TGG  CAC  AGC  ATC  GCG  GTG  ATG  CGC  CGG       480
Glu  Pro  Glu  Pro  Trp  Glu  Pro  Trp  His  Ser  Ile  Ala  Val  Met  Arg  Arg
     145                      150                      155

CTG  GGC  CTG  CTT  ATG  GGT  TCG  GTG  TGG  TTC  AAG  CTC  TGG  CGG  ATG  CTG       528
Leu  Gly  Leu  Leu  Met  Gly  Ser  Val  Trp  Phe  Lys  Leu  Trp  Arg  Met  Leu
160                      165                      170                      175

GCG  CTG  CCG  GTG  GTC  GGA  GCC  GCG  AAT  GCG  CTG  AAG  CTG  CGC  TAT  GAC       576
Ala  Leu  Pro  Val  Val  Gly  Ala  Ala  Asn  Ala  Leu  Lys  Leu  Arg  Tyr  Asp
                    180                      185                      190
```

| | | | | | | | | | | | | | | | | |
|---|---|---|---|---|---|---|---|---|---|---|---|---|---|---|---|---|
| GAT | GGC | GGC | CGG | GAT | TTG | CTC | TGC | ATC | CCG | CCG | GGC | GCC | GAA | GCC | GAT | 624 |
| Asp | Gly | Gly | Arg<br>195 | Asp | Leu | Leu | Cys | Ile<br>200 | Pro | Pro | Gly | Ala | Glu<br>205 | Ala | Asp | |
| CGG | CTC | GAG | GCG | GAT | CTC | GCG | ACC | CTG | CGG | CCC | GCG | GTC | GAT | GCG | CTG | 672 |
| Arg | Leu | Glu<br>210 | Ala | Asp | Leu | Ala | Thr<br>215 | Leu | Arg | Pro | Ala | Val<br>220 | Asp | Ala | Leu | |
| CTG | AAG | GCG | ATG | GGC | GGC | GAT | GCC | TCC | GAT | GCT | GCC | GGC | GGC | GGC | AGC | 720 |
| Leu | Lys<br>225 | Ala | Met | Gly | Gly | Asp<br>230 | Ala | Ser | Asp | Ala | Ala<br>235 | Gly | Gly | Gly | Ser | |
| AAC | AAC | TGG | GCG | GTC | GCT | CCG | GGC | CGC | ACG | GCG | ACC | GGC | AGG | CCG | ATC | 768 |
| Asn<br>240 | Asn | Trp | Ala | Val | Ala<br>245 | Pro | Gly | Arg | Thr | Ala<br>250 | Thr | Gly | Arg | Pro | Ile<br>255 | |
| CTC | GCG | GGC | GAT | CCG | CAT | CGC | GTC | TTC | GAA | ATC | CCT | GGC | TAT | TAT | GCG | 816 |
| Leu | Ala | Gly | Asp | Pro<br>260 | His | Arg | Val | Phe | Glu<br>265 | Ile | Pro | Gly | Tyr | Tyr<br>270 | Ala | |
| CAG | CAT | CAT | CTG | GCC | TGC | GAC | CGG | TTC | GAC | ATG | ATC | GGC | CTG | ACC | GTG | 864 |
| Gln | His | His | Leu<br>275 | Ala | Cys | Asp | Arg | Phe<br>280 | Asp | Met | Ile | Gly | Leu<br>285 | Thr | Val | |
| CCG | GGC | GTG | CCG | GGC | TTC | CCG | CAC | TTC | GCG | CAT | AAC | GGC | AAG | GTC | GCC | 912 |
| Pro | Gly | Val<br>290 | Pro | Gly | Phe | Pro | His<br>295 | Phe | Ala | His | Asn | Gly<br>300 | Lys | Val | Ala | |
| TAT | AGC | GTC | ACG | CAT | GCC | TTC | ATG | GAC | ATC | CAC | GAT | CTC | TAT | CTC | GAG | 960 |
| Tyr | Ser<br>305 | Val | Thr | His | Ala | Phe<br>310 | Met | Asp | Ile | His | Asp<br>315 | Leu | Tyr | Leu | Glu | |
| CAG | TTC | GCG | GGG | GAG | GGC | CGC | ACT | GCG | CGG | TTC | GGC | AAC | GAT | TTC | GAG | 1008 |
| Gln<br>320 | Phe | Ala | Gly | Glu | Gly<br>325 | Arg | Thr | Ala | Arg | Phe<br>330 | Gly | Asn | Asp | Phe | Glu<br>335 | |
| CCC | GTC | GCC | TGG | AGC | CGG | GAC | CGT | ATC | GCG | GTC | CGG | GGT | GGC | GCC | GAT | 1056 |
| Pro | Val | Ala | Trp | Ser<br>340 | Arg | Asp | Arg | Ile | Ala<br>345 | Val | Arg | Gly | Gly | Ala<br>350 | Asp | |
| CGC | GAG | TTC | GAT | ATC | GTC | GAG | ACT | CGC | CAT | GGC | CCG | GTT | ATC | GCG | GGC | 1104 |
| Arg | Glu | Phe | Asp | Ile<br>355 | Val | Glu | Thr | Arg | His<br>360 | Gly | Pro | Val | Ile | Ala<br>365 | Gly | |
| GAT | CCG | CGC | GAT | GGC | GCA | GCG | CTC | ACG | CTG | CGT | TCG | GTC | CAG | TTC | GCC | 1152 |
| Asp | Pro | Arg<br>370 | Asp | Gly | Ala | Ala | Leu<br>375 | Thr | Leu | Arg | Ser | Val<br>380 | Gln | Phe | Ala | |
| GAG | ACC | GAT | CTG | TCC | TTC | GAC | TGC | CTG | ACG | CGG | ATG | CCG | GGC | GCA | TCG | 1200 |
| Glu | Thr | Asp<br>385 | Leu | Ser | Phe | Asp<br>390 | Cys | Leu | Thr | Arg | Met<br>395 | Pro | Gly | Ala | Ser | |
| ACC | GTG | GCC | CAG | CTC | TAC | GAC | GCG | ACG | CGC | GGC | TGG | GGC | CTG | ATC | GAC | 1248 |
| Thr<br>400 | Val | Ala | Gln | Leu | Tyr<br>405 | Asp | Ala | Thr | Arg | Gly<br>410 | Trp | Gly | Leu | Ile | Asp<br>415 | |
| CAT | AAC | CTC | GTC | GCC | GGG | GAT | GTC | GCG | GGC | TCG | ATC | GGC | CAT | CTG | GTC | 1296 |
| His | Asn | Leu | Val | Ala<br>420 | Gly | Asp | Val | Ala | Gly<br>425 | Ser | Ile | Gly | His | Leu<br>430 | Val | |
| CGC | GCC | CGC | GTT | CCG | TCC | CGT | CCG | CGC | GAA | AAC | GGC | TGG | CTG | CCG | GTG | 1344 |
| Arg | Ala | Arg | Val | Pro<br>435 | Ser | Arg | Pro | Arg | Glu<br>440 | Asn | Gly | Trp | Leu | Pro<br>445 | Val | |
| CCG | GGC | TGG | TCC | GGC | GAG | CAT | GAA | TGG | CGG | GGC | TGG | ATT | CCG | CAC | GAG | 1392 |
| Pro | Gly | Trp | Ser<br>450 | Gly | Glu | His | Glu | Trp<br>455 | Arg | Gly | Trp | Ile | Pro<br>460 | His | Glu | |
| GCG | ATG | CCG | CGC | GTG | ATC | GAT | CCG | CCG | GGC | GGC | ATC | ATC | GTC | ACG | GCG | 1440 |
| Ala | Met | Pro<br>465 | Arg | Val | Ile | Asp | Pro<br>470 | Pro | Gly | Gly | Ile | Ile<br>475 | Val | Thr | Ala | |
| AAT | AAT | CGC | GTC | GTG | GCC | GAT | GAC | CAT | CCC | GAT | TAT | CTC | TGC | ACC | GAT | 1488 |
| Asn<br>480 | Asn | Arg | Val | Val | Ala<br>485 | Asp | Asp | His | Pro | Asp<br>490 | Tyr | Leu | Cys | Thr | Asp<br>495 | |
| TGC | CAT | CCG | CCC | TAC | CGC | GCC | GAG | CGC | ATC | ATG | AAG | CGC | CTG | GTC | GCC | 1536 |
| Cys | His | Pro | Pro | Tyr<br>500 | Arg | Ala | Glu | Arg | Ile<br>505 | Met | Lys | Arg | Leu | Val<br>510 | Ala | |
| AAT | CCG | GCT | TTC | GCC | GTC | GAC | GAT | GCC | GCC | GCG | ATC | CAT | GCC | GAT | ACG | 1584 |

| | | | | | | | | | | | | | | | |
|---|---|---|---|---|---|---|---|---|---|---|---|---|---|---|---|
| Asn | Pro | Ala | Phe | Ala | Val | Asp | Asp | Ala | Ala | Ala | Ile | His | Ala | Asp | Thr |
| | | 515 | | | | 520 | | | | | | 525 | | | |

| CTG | TCG | CCC | CAT | GTC | GGG | TTG | CTG | CGC | CGG | AGG | CTC | GAG | GCG | CTT | GGA | 1632 |
|---|---|---|---|---|---|---|---|---|---|---|---|---|---|---|---|---|
| Leu | Ser | Pro | His | Val | Gly | Leu | Leu | Arg | Arg | Arg | Leu | Glu | Ala | Leu | Gly | |
| | | 530 | | | | 535 | | | | | 540 | | | | | |

| GCC | CGC | GAC | GAC | TCC | GCG | GCC | GAA | GGG | CTG | AGG | CAG | ATG | CTC | GTC | GCC | 1680 |
|---|---|---|---|---|---|---|---|---|---|---|---|---|---|---|---|---|
| Ala | Arg | Asp | Asp | Ser | Ala | Ala | Glu | Gly | Leu | Arg | Gln | Met | Leu | Val | Ala | |
| | 545 | | | | 550 | | | | | 555 | | | | | | |

| TGG | GAC | GGC | CGC | ATG | GAT | GCG | GCT | TCG | GAG | GTC | GCG | TCT | GCC | TAC | AAT | 1728 |
|---|---|---|---|---|---|---|---|---|---|---|---|---|---|---|---|---|
| Trp | Asp | Gly | Arg | Met | Asp | Ala | Ala | Ser | Glu | Val | Ala | Ser | Ala | Tyr | Asn | |
| 560 | | | | | 565 | | | | | 570 | | | | | 575 | |

| GCG | TTC | CGC | AGG | GCG | CTG | ACG | CGG | CTG | GTG | ACG | GAC | CGC | AGC | GGG | CTG | 1776 |
|---|---|---|---|---|---|---|---|---|---|---|---|---|---|---|---|---|
| Ala | Phe | Arg | Arg | Ala | Leu | Thr | Arg | Leu | Val | Thr | Asp | Arg | Ser | Gly | Leu | |
| | | | | 580 | | | | | 585 | | | | | 590 | | |

| GAG | CAG | GCG | ATA | TCG | CAT | CCC | TTC | GCG | GCT | GTC | GCG | CCG | GGC | GTC | TCA | 1824 |
|---|---|---|---|---|---|---|---|---|---|---|---|---|---|---|---|---|
| Glu | Gln | Ala | Ile | Ser | His | Pro | Phe | Ala | Ala | Val | Ala | Pro | Gly | Val | Ser | |
| | | | 595 | | | | | 600 | | | | | 605 | | | |

| CCG | CAA | GGC | CAG | GTC | TGG | TGG | GCC | GTG | CCG | ACC | CTG | CTG | CGC | GAC | GAC | 1872 |
|---|---|---|---|---|---|---|---|---|---|---|---|---|---|---|---|---|
| Pro | Gln | Gly | Gln | Val | Trp | Trp | Ala | Val | Pro | Thr | Leu | Leu | Arg | Asp | Asp | |
| | | 610 | | | | | 615 | | | | | 620 | | | | |

| GAT | GCC | GGA | ATG | CTG | AAG | GGC | TGG | AGC | TGG | GAC | CAG | GCC | TTG | TCT | GAG | 1920 |
|---|---|---|---|---|---|---|---|---|---|---|---|---|---|---|---|---|
| Asp | Ala | Gly | Met | Leu | Lys | Gly | Trp | Ser | Trp | Asp | Gln | Ala | Leu | Ser | Glu | |
| | 625 | | | | | 630 | | | | | 635 | | | | | |

| GCC | CTC | TCG | GTC | GCG | TCG | CAG | AAC | CTG | ACC | GGG | CGA | AGC | TGG | GGC | GAA | 1968 |
|---|---|---|---|---|---|---|---|---|---|---|---|---|---|---|---|---|
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |

| GAG | CAT | CGG | CCG | CGC | TTC | ACG | CAT | CCG | CTT | GCC | ACG | CAA | TTC | CCG | GCC | 2016 |
|---|---|---|---|---|---|---|---|---|---|---|---|---|---|---|---|---|
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |

| TGG | GCG | GGG | CTG | CTG | AAT | CCG | GCT | TCC | CGT | CCG | ATC | GGT | GGC | GAT | GGC | 2064 |
|---|---|---|---|---|---|---|---|---|---|---|---|---|---|---|---|---|
| Trp | Ala | Gly | Leu | Leu | Asn | Pro | Ala | Ser | Arg | Pro | Ile | Gly | Gly | Asp | Gly | |
| | | | 675 | | | | | 680 | | | | | 685 | | | |

| GAT | ACC | GTG | CTG | GCG | AAC | GGG | CTC | GTC | CCG | TCA | GCC | GGG | CCG | CAG | GCG | 2112 |
|---|---|---|---|---|---|---|---|---|---|---|---|---|---|---|---|---|
| Asp | Thr | Val | Leu | Ala | Asn | Gly | Leu | Val | Pro | Ser | Ala | Gly | Pro | Gln | Ala | |
| | | 690 | | | | | 695 | | | | | 700 | | | | |

| ACC | TAT | GGT | GCC | CTG | TCG | CGC | TAC | GTC | TTC | GAT | GTC | GGC | AAT | TGG | GAC | 2160 |
|---|---|---|---|---|---|---|---|---|---|---|---|---|---|---|---|---|
| Thr | Tyr | Gly | Ala | Leu | Ser | Arg | Tyr | Val | Phe | Asp | Val | Gly | Asn | Trp | Asp | |
| | 705 | | | | | 710 | | | | | 715 | | | | | |

| AAT | AGC | CGC | TGG | GTC | GTC | TTC | CAC | GGC | GCC | TCC | GGG | CAT | CCG | GCC | AGC | 2208 |
|---|---|---|---|---|---|---|---|---|---|---|---|---|---|---|---|---|
| Asn | Ser | Arg | Trp | Val | Val | Phe | His | Gly | Ala | Ser | Gly | His | Pro | Ala | Ser | |
| 720 | | | | | 725 | | | | | 730 | | | | | 735 | |

| GCC | CAT | TAT | GCC | GAT | CAG | AAT | GCG | CCC | TGG | AGC | GAC | TGT | GCG | ATG | GTG | 2256 |
|---|---|---|---|---|---|---|---|---|---|---|---|---|---|---|---|---|
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |

| CCG | ATG | CTC | TAT | AGC | TGG | GAC | AGG | ATC | GCG | GCA | GAG | GCC | GTG | ACG | TCG | 2304 |
|---|---|---|---|---|---|---|---|---|---|---|---|---|---|---|---|---|
| Pro | Met | Leu | Tyr | Ser | Trp | Asp | Arg | Ile | Ala | Ala | Glu | Ala | Val | Thr | Ser | |
| | | | 755 | | | | | 760 | | | | | 765 | | | |

| CAG | GAA | CTC | GTC | CCG | GCC | TGA | 2325 |
|---|---|---|---|---|---|---|---|
| Gln | Glu | Leu | Val | Pro | Ala | | |
| | | 770 | | | | | |

( 2 ) INFORMATION FOR SEQ ID NO:8:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Thr | Met | Ala | Ala | Asn | Thr | Asp | Arg | Ala | Val | Leu | Gln | Ala | Ala | Leu |
|---|---|---|---|---|---|---|---|---|---|---|---|---|---|---|---|
| -1 | 1 | | | | 5 | | | | | 10 | | | | | 15 |

```
Pro Pro Leu Ser Gly Ser Leu Pro Ile Pro Gly Leu Ser Ala Ser Val
            20              25              30

Arg Val Arg Arg Asp Ala Trp Gly Ile Pro His Ile Lys Ala Ser Gly
            35              40              45

Glu Ala Asp Ala Tyr Arg Ala Leu Gly Phe Val His Ser Gln Asp Arg
            50              55              60

Leu Phe Gln Met Glu Leu Thr Arg Arg Lys Ala Leu Gly Arg Ala Ala
        65              70              75

Glu Trp Leu Gly Ala Glu Ala Ala Glu Ala Asp Ile Leu Val Arg Arg
80              85              90              95

Leu Gly Met Glu Lys Val Cys Arg Arg Asp Phe Glu Ala Leu Gly Val
                100             105             110

Glu Ala Lys Asp Met Leu Arg Ala Tyr Val Ala Gly Val Asn Ala Phe
            115             120             125

Leu Ala Ser Gly Ala Pro Leu Pro Val Glu Tyr Gly Leu Leu Gly Ala
            130             135             140

Glu Pro Glu Pro Trp Glu Pro Trp His Ser Ile Ala Val Met Arg Arg
            145             150             155

Leu Gly Leu Leu Met Gly Ser Val Trp Phe Lys Leu Trp Arg Met Leu
160             165             170             175

Ala Leu Pro Val Val Gly Ala Ala Asn Ala Leu Lys Leu Arg Tyr Asp
                180             185             190

Asp Gly Gly Arg Asp Leu Leu Cys Ile Pro Pro Gly Ala Glu Ala Asp
                195             200             205

Arg Leu Glu Ala Asp Leu Ala Thr Leu Arg Pro Ala Val Asp Ala Leu
            210             215             220

Leu Lys Ala Met Gly Gly Asp Ala Ser Asp Ala Ala Gly Gly Gly Ser
        225             230             235

Asn Asn Trp Ala Val Ala Pro Gly Arg Thr Ala Thr Gly Arg Pro Ile
240             245             250             255

Leu Ala Gly Asp Pro His Arg Val Phe Glu Ile Pro Gly Tyr Tyr Ala
            260             265             270

Gln His His Leu Ala Cys Asp Arg Phe Asp Met Ile Gly Leu Thr Val
            275             280             285

Pro Gly Val Pro Gly Phe Pro His Phe Ala His Asn Gly Lys Val Ala
        290             295             300

Tyr Ser Val Thr His Ala Phe Met Asp Ile His Asp Leu Tyr Leu Glu
        305             310             315

Gln Phe Ala Gly Glu Gly Arg Thr Ala Arg Phe Gly Asn Asp Phe Glu
320             325             330             335

Pro Val Ala Trp Ser Arg Asp Arg Ile Ala Val Arg Gly Gly Ala Asp
                340             345             350

Arg Glu Phe Asp Ile Val Glu Thr Arg His Gly Pro Val Ile Ala Gly
            355             360             365

Asp Pro Arg Asp Gly Ala Ala Leu Thr Leu Arg Ser Val Gln Phe Ala
            370             375             380

Glu Thr Asp Leu Ser Phe Asp Cys Leu Thr Arg Met Pro Gly Ala Ser
        385             390             395

Thr Val Ala Gln Leu Tyr Asp Ala Thr Arg Gly Trp Gly Leu Ile Asp
400             405             410             415

His Asn Leu Val Ala Gly Asp Val Ala Gly Ser Ile Gly His Leu Val
            420             425             430

Arg Ala Arg Val Pro Ser Arg Pro Arg Glu Asn Gly Trp Leu Pro Val
            435             440             445

Pro Gly Trp Ser Gly Glu His Glu Trp Arg Gly Trp Ile Pro His Glu
```

|            |     |     |     |     |     |     |     |     |     |     |     |     |     |     |
|---|---|---|---|---|---|---|---|---|---|---|---|---|---|---|
|            |     |     |     | 450 |     |     |     |     | 455 |     |     |     | 460 |     |
| Ala | Met | Pro | Arg | Val | Ile | Asp | Pro | Pro | Gly | Gly | Ile | Ile | Val | Thr | Ala |
| 465 | | | | | 470 | | | | 475 | | | | | | |
| Asn | Asn | Arg | Val | Val | Ala | Asp | Asp | His | Pro | Asp | Tyr | Leu | Cys | Thr | Asp |
| 480 | | | | | 485 | | | | 490 | | | | | 495 | |
| Cys | His | Pro | Pro | Tyr | Arg | Ala | Glu | Arg | Ile | Met | Lys | Arg | Leu | Val | Ala |
| | | | | 500 | | | | | 505 | | | | | 510 | |
| Asn | Pro | Ala | Phe | Ala | Val | Asp | Asp | Ala | Ala | Ile | His | Ala | Asp | Thr | |
| | | | | 515 | | | | | 520 | | | | 525 | | |
| Leu | Ser | Pro | His | Val | Gly | Leu | Leu | Arg | Arg | Arg | Leu | Glu | Ala | Leu | Gly |
| | | | 530 | | | | | 535 | | | | | 540 | | |
| Ala | Arg | Asp | Asp | Ser | Ala | Ala | Glu | Gly | Leu | Arg | Gln | Met | Leu | Val | Ala |
| | 545 | | | | | 550 | | | | | 555 | | | | |
| Trp | Asp | Gly | Arg | Met | Asp | Ala | Ala | Ser | Glu | Val | Ala | Ser | Ala | Tyr | Asn |
| 560 | | | | | 565 | | | | | 570 | | | | | 575 |
| Ala | Phe | Arg | Arg | Ala | Leu | Thr | Arg | Leu | Val | Thr | Asp | Arg | Ser | Gly | Leu |
| | | | | 580 | | | | | 585 | | | | | 590 | |
| Glu | Gln | Ala | Ile | Ser | His | Pro | Phe | Ala | Ala | Val | Ala | Pro | Gly | Val | Ser |
| | | | 595 | | | | | 600 | | | | | 605 | | |
| Pro | Gln | Gly | Gln | Val | Trp | Trp | Ala | Val | Pro | Thr | Leu | Leu | Arg | Asp | Asp |
| | | 610 | | | | | 615 | | | | | 620 | | | |
| Asp | Ala | Gly | Met | Leu | Lys | Gly | Trp | Ser | Trp | Asp | Gln | Ala | Leu | Ser | Glu |
| | 625 | | | | | 630 | | | | | 635 | | | | |
| Ala | Leu | Ser | Val | Ala | Ser | Gln | Asn | Leu | Thr | Gly | Arg | Ser | Trp | Gly | Glu |
| 640 | | | | | 645 | | | | | 650 | | | | | 655 |
| Glu | His | Arg | Pro | Arg | Phe | Thr | His | Pro | Leu | Ala | Thr | Gln | Phe | Pro | Ala |
| | | | | 660 | | | | | 665 | | | | | 670 | |
| Trp | Ala | Gly | Leu | Leu | Asn | Pro | Ala | Ser | Arg | Pro | Ile | Gly | Gly | Asp | Gly |
| | | | 675 | | | | | 680 | | | | | 685 | | |
| Asp | Thr | Val | Leu | Ala | Asn | Gly | Leu | Val | Pro | Ser | Ala | Gly | Pro | Gln | Ala |
| | | 690 | | | | | 695 | | | | | 700 | | | |
| Thr | Tyr | Gly | Ala | Leu | Ser | Arg | Tyr | Val | Phe | Asp | Val | Gly | Asn | Trp | Asp |
| | 705 | | | | | 710 | | | | | 715 | | | | |
| Asn | Ser | Arg | Trp | Val | Val | Phe | His | Gly | Ala | Ser | Gly | His | Pro | Ala | Ser |
| 720 | | | | | 725 | | | | | 730 | | | | | 735 |
| Ala | His | Tyr | Ala | Asp | Gln | Asn | Ala | Pro | Trp | Ser | Asp | Cys | Ala | Met | Val |
| | | | | 740 | | | | | 745 | | | | | 750 | |
| Pro | Met | Leu | Tyr | Ser | Trp | Asp | Arg | Ile | Ala | Ala | Glu | Ala | Val | Thr | Ser |
| | | | 755 | | | | | 760 | | | | | 765 | | |
| Gln | Glu | Leu | Val | Pro | Ala | | | | | | | | | | |
| | | 770 | | | | | | | | | | | | | |

( 2 ) INFORMATION FOR SEQ ID NO:9:

( i ) SEQUENCE CHARACTERISTICS:
( A ) LENGTH: 2373 base pairs
( B ) TYPE: nucleic acid
( C ) STRANDEDNESS: unknown
( D ) TOPOLOGY: linear ( i i ) MOLECULE TYPE: DNA (genomic)

( x i ) SEQUENCE DESCRIPTION: SEQ ID NO:9:

| | | | | | |
|---|---|---|---|---|---|
| ATGACTATGG | CAGCTAATAC | GGATCGCGCG | GTCTTGCAGG | CGGCGCTGCC | GCCGCTTTCC | 60 |
| GGCAGCCTCC | CCATTCCCGG | ATTGAGCGCG | TCGGTCCGCG | TCCGGCGCGA | TGCCTGGGGC | 120 |
| ATCCCGCATA | TCAAGGCCTC | GGGCGAGGCC | GATGCCTATC | GGGCGCTGGG | CTTCGTCCAT | 180 |
| TCGCAGGACC | GTCTTTTCCA | GATGGAGCTG | ACGCGTCGCA | AGGCGCTGGG | ACGCGCGGCC | 240 |

```
GAATGGCTGG  GCGCCGAGGC  CGCCGAGGCC  GATATCCTCG  TGCGCCGGCT  CGGAATGGAA    300
AAAGTCTGCC  GGCGCGACTT  CGAGGCCTTG  GGCGTCGAGG  CGAAGGACAT  GCTGCGGGCT    360
TATGTCGCCG  GCGTGAACGC  ATTCCTGGCT  TCCGGTGCTC  CCCTGCCTGT  CGAATACGGA    420
TTGCTCGGAG  CAGAGCCGGA  GCCCTGGGAG  CCTTGGCACA  GCATCGCGGT  GATGCGCCGG    480
CTGGGCCTGC  TTATGGGTTC  GGTGTGGTTC  AAGCTCTGGC  GGATGCTGGC  GCTGCCGGTG    540
GTCGGAGCCG  CGAATGCGCT  GAAGCTGCGC  TATGACCGGC  TCGAGGCGGA  TCTCGCGACC    600
CTGCGGCCCG  CGGTCGATGC  GCTGGATGGC  GGCCGGGATT  TGCTCTGCAT  CCCGCCGGGC    660
GCCGAAGCCG  ATCGGCTCGA  GGCGGATCTC  GCGACCCTGC  GGCCCGCGGT  CGATGCGCTG    720
CTGAAGGCGA  TGGGCGGCGA  TGCCTCCGAT  GCTGCCGGCG  GCGGATCCAA  CAACTGGGCG    780
GTCGCTCCGG  GCCGCACGGC  GACCGGCAGG  CCGATCCTCG  CGGGCGATCC  GCATCGCGTC    840
TTCGAAATCC  CGGGCATGTA  TGCGCAGCAT  CATCTGGCCT  GCGACCGGTT  CGACATGATC    900
GGCCTGACCG  TGCCGGGCGT  GCCGGGCTTC  CCGCACTTCG  CGCATAACGG  CAAGGTCGCC    960
TATAGCGTCA  CGCATGCCTT  CATGGACATC  CACGATCTCT  ATCTCGAGCA  GTTCGCGGGG   1020
GAGGGCCGCA  CTGCGCGGTT  CGGCAACGAT  TTCGAGCCCG  TCGCCTGGAG  CCGGGACCGT   1080
ATCGCGGTCC  GGGGTGGCGC  CGATCGCGAG  TTCGATATCG  TCGAGACGCG  CCATGGCCCG   1140
GTTATCGCGG  GCGATCCGCG  CGATGGCGCA  GCGCTCACGC  TGCGTTCGGT  CCAGTTCGCC   1200
GAGACCGATC  TGTCCTTCGA  CTGCCTGACG  CGGATGCCGG  GCGCATCGAC  CGTGGCCCAG   1260
CTCTACGACG  CGACGCGCGG  CTGGGGCCTG  ATCGACCATA  ACCTCGTCGC  CGGGGATGTC   1320
GCGGGCTCGA  TCGGCCATCT  GGTCCGCGCC  CGCGTTCCGT  CCCGTCCGCG  CGAAAACGGC   1380
TGGCTGCCGG  TGCCGGGCTG  GTCCGGCGAG  CATGAATGGC  GGGGCTGGAT  TCCGCACGAG   1440
GCGATGCCGC  GCGTGATCGA  TCCGCCGGGC  GGCATCATCG  TCACGGCGAA  TAATCGCGTC   1500
GTGGCCGATG  ACCATCCCGA  TTATCTCTGC  ACCGATTGCC  ATCCGCCCTA  CCGCGCCGAG   1560
CGCATCATGA  AGCGCCTGGT  CGCCAATCCG  GCTTTCGCCG  TCGACGATGC  CGCCGCGATC   1620
CATGCCGATA  CGCTGTCGCC  CCATGTCGGG  TTGCTGCGCC  GGAGGCTCGA  GGCGCTTGGA   1680
GCCCGCGACG  ACTCCGCGGC  CGAAGGGCTG  AGGCAGATGC  TCGTCGCCTG  GGACGGCCGC   1740
ATGGATGCGG  CTTCGGAGGT  CGCGTCTGCC  TACAATGCGT  TCCGCAGGGC  GCTGACGCGG   1800
CTGGTGACGG  ACCGCAGCGG  GCTGGAGCAG  GCGATATCGC  ATCCCTTCGC  GGCTGTCGCG   1860
CCGGGCGTCT  CACCGCAAGG  CCAGGTCTGG  TGGGCCGTGC  CGACCCTGCT  GCGCGACGAC   1920
GATGCCGGAA  TGCTGAAGGG  CTGGAGCTGG  GACCAGGCCT  TGTCTGAGGC  CCTCTCGGTC   1980
GCGTCGCAGA  ACCTGACCGG  GCGAAGCTGG  GGCGAAGAGC  ATCGGCCGCG  CTTCACGCAT   2040
CCGCTTGCCA  CGCAATTCCC  GGCCTGGGCG  GGCTGCTGA   ATCCGGCTTC  CCGTCCGATC   2100
GGTGGCGATG  GCGATACCGT  GCTGGCGAAC  GGGCTCGTCC  CGTCAGCCGG  GCCGCAGGCG   2160
ACCTATGGTG  CCCTGTCGCG  CTACGTCTTC  GATGTCGGCA  ATTGGGACAA  TAGCCGCTGG   2220
GTCGTCTTCC  ACGGCGCCTC  CGGGCATCCG  GCCAGCGCCC  ATTATGCCGA  TCAGAATGCG   2280
CCCTGGAGCG  ACTGTGCGAT  GGTGCCGATG  CTCTATAGCT  GGGACAGGAT  CGCGGCAGAG   2340
GCCGTGACGT  CGCAGGAACT  CGTCCCGGCC  TGA                                  2373
```

( 2 ) INFORMATION FOR SEQ ID NO:10:

( i ) SEQUENCE CHARACTERISTICS:
        ( A ) LENGTH: 2325 base pairs
        ( B ) TYPE: nucleic acid
        ( C ) STRANDEDNESS: unknown
        ( D ) TOPOLOGY: linear (ii) MOLECULE TYPE: DNA (genomic)

(ix) FEATURE:
    (A) NAME/KEY: CDS
    (B) LOCATION: 1..2322

(ix) FEATURE:
    (A) NAME/KEY: matpeptide
    (B) LOCATION: 4..2322

(xi) SEQUENCE DESCRIPTION: SEQ ID NO:10:

```
ATG ACT ATG GCA GCT AAT ACG GAT CGC GCG GTC TTG CAG GCG GCG CTG       48
Met Thr Met Ala Ala Asn Thr Asp Arg Ala Val Leu Gln Ala Ala Leu
 -1   1               5                  10                  15

CCG CCG CTT TCC GGC AGC CTC CCC ATT CCC GGA TTG AGC GCG TCG GTC       96
Pro Pro Leu Ser Gly Ser Leu Pro Ile Pro Gly Leu Ser Ala Ser Val
             20                  25                  30

CGC GTC CGG CGC GAT GCC TGG GGC ATC CCG CAT ATC AAG GCC TCG GGC      144
Arg Val Arg Arg Asp Ala Trp Gly Ile Pro His Ile Lys Ala Ser Gly
                 35                  40                  45

GAG GCC GAT GCC TAT CGG GCG CTG GGC TTC GTC CAT TCG CAG GAC CGT      192
Glu Ala Asp Ala Tyr Arg Ala Leu Gly Phe Val His Ser Gln Asp Arg
             50                  55                  60

CTT TTC CAG ATG GAG CTG ACG CGT CGC AAG GCG CTG GGA CGC GCG GCC      240
Leu Phe Gln Met Glu Leu Thr Arg Arg Lys Ala Leu Gly Arg Ala Ala
     65                  70                  75

GAA TGG CTG GGC GCC GAG GCC GCC GAG GCC GAT ATC CTC GTG CGC CGG      288
Glu Trp Leu Gly Ala Glu Ala Ala Glu Ala Asp Ile Leu Val Arg Arg
 80                  85                  90                  95

CTC GGA ATG GAA AAA GTC TGC CGG CGC GAC TTC GAG GCC TTG GGC GTC      336
Leu Gly Met Glu Lys Val Cys Arg Arg Asp Phe Glu Ala Leu Gly Val
                100                 105                 110

GAG GCG AAG GAC ATG CTG CGG GCT TAT GTC GCC GGC GTG AAC GCA TTC      384
Glu Ala Lys Asp Met Leu Arg Ala Tyr Val Ala Gly Val Asn Ala Phe
                115                 120                 125

CTG GCT TCC GGT GCT CCC CTG CCT GTC GAA TAC GGA TTG CTC GGA GCA      432
Leu Ala Ser Gly Ala Pro Leu Pro Val Glu Tyr Gly Leu Leu Gly Ala
            130                 135                 140

GAG CCG GAG CCC TGG GAG CCT TGG CAC AGC ATC GCG GTG ATG CGC CGG      480
Glu Pro Glu Pro Trp Glu Pro Trp His Ser Ile Ala Val Met Arg Arg
            145                 150                 155

CTG GGC CTG CTT ATG GGT TCG GTG TGG TTC AAG CTC TGG CGG ATG CTG      528
Leu Gly Leu Leu Met Gly Ser Val Trp Phe Lys Leu Trp Arg Met Leu
160                 165                 170                 175

GCG CTG CCG GTG GTC GGA GCC GCG AAT GCG CTG AAG CTG CGC TAT GAC      576
Ala Leu Pro Val Val Gly Ala Ala Asn Ala Leu Lys Leu Arg Tyr Asp
                180                 185                 190

GAT GGC GGC CGG GAT TTG CTC TGC ATC CCG CCG GGC GCC GAA GCC GAT      624
Asp Gly Gly Arg Asp Leu Leu Cys Ile Pro Pro Gly Ala Glu Ala Asp
                195                 200                 205

CGG CTC GAG GCG GAT CTC GCG ACC CTG CGG CCC GCG GTC GAT GCG CTG      672
Arg Leu Glu Ala Asp Leu Ala Thr Leu Arg Pro Ala Val Asp Ala Leu
            210                 215                 220

CTG AAG GCG ATG GGC GGC GAT GCC TCC GAT GCT GCC GGC GGC GGC AGC      720
Leu Lys Ala Met Gly Gly Asp Ala Ser Asp Ala Ala Gly Gly Gly Ser
            225                 230                 235

AAC AAC TGG GCG GTC GCT CCG GGC CGC ACG GCG ACC GGC AGG CCG ATC      768
Asn Asn Trp Ala Val Ala Pro Gly Arg Thr Ala Thr Gly Arg Pro Ile
240                 245                 250                 255

CTC GCG GGC GAT CCG CAT CGC GTC TTC GAA ATC CCG GGC ATG TAC TAT      816
Leu Ala Gly Asp Pro His Arg Val Phe Glu Ile Pro Gly Met Tyr Tyr
                260                 265                 270

CAG CAT CAT CTG GCC TGC GAC CGG TTC GAC ATG ATC GGC CTG ACC GTG      864
Gln His His Leu Ala Cys Asp Arg Phe Asp Met Ile Gly Leu Thr Val
```

|  |  |  |  |  |  |  |  |  |  |  |  |  |  |  |  |
|---|---|---|---|---|---|---|---|---|---|---|---|---|---|---|---|
|  |  |  | 275 |  |  |  | 280 |  |  |  | 285 |  |  |  |  |
| CCG | GGC | GTG | CCG | GGC | TTC | CCG | CAC | TTC | GCG | CAT | AAC | GGC | AAG | GTC | GCC |
| Pro | Gly | Val<br>290 | Pro | Gly | Phe | Pro | His<br>295 | Phe | Ala | His | Asn | Gly<br>300 | Lys | Val | Ala |

912

| TAT | TGC | GTC | ACC | CAT | GCC | TTC | ATG | GAC | ATC | CAC | GAT | CTC | TAT | CTC | GAG |
|---|---|---|---|---|---|---|---|---|---|---|---|---|---|---|---|
| Tyr | Cys<br>305 | Val | Thr | His | Ala | Phe<br>310 | Met | Asp | Ile | His | Asp<br>315 | Leu | Tyr | Leu | Glu |

960

| CAG | TTC | GCG | GGG | GAG | GGC | CGC | ACT | GCG | CGG | TTC | GGC | AAC | GAT | TTC | GAG |
|---|---|---|---|---|---|---|---|---|---|---|---|---|---|---|---|
| Gln<br>320 | Phe | Ala | Gly | Glu | Gly<br>325 | Arg | Thr | Ala | Arg<br>330 | Phe | Gly | Asn | Asp | Phe<br>335 | Glu |

1008

| CCC | GTC | GCC | TGG | AGC | CGG | GAC | CGT | ATC | GCG | GTC | CGG | GGT | GGC | GCC | GAT |
|---|---|---|---|---|---|---|---|---|---|---|---|---|---|---|---|
| Pro | Val | Ala | Trp | Ser<br>340 | Arg | Asp | Arg | Ile | Ala<br>345 | Val | Arg | Gly | Gly | Ala<br>350 | Asp |

1056

| CGC | GAG | TTC | GAT | ATC | GTC | GAG | ACG | CGC | CAT | GGC | CCG | GTT | ATC | GCG | GGC |
|---|---|---|---|---|---|---|---|---|---|---|---|---|---|---|---|
| Arg | Glu | Phe | Asp<br>355 | Ile | Val | Glu | Thr | Arg<br>360 | His | Gly | Pro | Val | Ile<br>365 | Ala | Gly |

1104

| GAT | CCG | CGC | GAT | GGC | GCA | GCG | CTC | ACG | CTG | CGT | TCG | GTC | CAG | TTC | GCC |
|---|---|---|---|---|---|---|---|---|---|---|---|---|---|---|---|
| Asp | Pro | Arg<br>370 | Asp | Gly | Ala | Ala | Leu<br>375 | Thr | Leu | Arg | Ser | Val<br>380 | Gln | Phe | Ala |

1152

| GAG | ACC | GAT | CTG | TCC | TTC | GAC | TGC | CTG | ACG | CGG | ATG | CCG | GGC | GCA | TCG |
|---|---|---|---|---|---|---|---|---|---|---|---|---|---|---|---|
| Glu | Thr | Asp<br>385 | Leu | Ser | Phe | Asp<br>390 | Cys | Leu | Thr | Arg | Met<br>395 | Pro | Gly | Ala | Ser |

1200

| ACC | GTG | GCC | CAG | CTC | TAC | GAC | GCG | ACG | CGC | GGC | TGG | GGC | CTG | ATC | GAC |
|---|---|---|---|---|---|---|---|---|---|---|---|---|---|---|---|
| Thr<br>400 | Val | Ala | Gln | Leu | Tyr<br>405 | Asp | Ala | Thr | Arg | Gly<br>410 | Trp | Gly | Leu | Ile | Asp<br>415 |

1248

| CAT | AAC | CTC | GTC | GCC | GGG | GAT | GTC | GCG | GGC | TCG | ATC | GGC | CAT | CTG | GTC |
|---|---|---|---|---|---|---|---|---|---|---|---|---|---|---|---|
| His | Asn | Leu | Val | Ala<br>420 | Gly | Asp | Val | Ala | Gly<br>425 | Ser | Ile | Gly | His | Leu<br>430 | Val |

1296

| CGC | GCC | CGC | GTT | CCG | TCC | CGT | CCG | CGC | GAA | AAC | GGC | TGG | CTG | CCG | GTG |
|---|---|---|---|---|---|---|---|---|---|---|---|---|---|---|---|
| Arg | Ala | Arg | Val<br>435 | Pro | Ser | Arg | Pro | Arg<br>440 | Glu | Asn | Gly | Trp | Leu<br>445 | Pro | Val |

1344

| CCG | GGC | TGG | TCC | GGC | GAG | CAT | GAA | TGG | CGG | GGC | TGG | ATT | CCG | CAC | GAG |
|---|---|---|---|---|---|---|---|---|---|---|---|---|---|---|---|
| Pro | Gly | Trp | Ser<br>450 | Gly | Glu | His | Glu | Trp<br>455 | Arg | Gly | Trp | Ile | Pro<br>460 | His | Glu |

1392

| GCG | ATG | CCG | CGC | GTG | ATC | GAT | CCG | CCG | GGC | GGC | ATC | ATC | GTC | ACG | GCG |
|---|---|---|---|---|---|---|---|---|---|---|---|---|---|---|---|
| Ala | Met | Pro<br>465 | Arg | Val | Ile | Asp | Pro<br>470 | Pro | Gly | Gly | Ile | Ile<br>475 | Val | Thr | Ala |

1440

| AAT | AAT | CGC | GTC | GTG | GCC | GAT | GAC | CAT | CCC | GAT | TAT | CTC | TGC | ACC | GAT |
|---|---|---|---|---|---|---|---|---|---|---|---|---|---|---|---|
| Asn<br>480 | Asn | Arg | Val | Val | Ala<br>485 | Asp | Asp | His | Pro | Asp<br>490 | Tyr | Leu | Cys | Thr | Asp<br>495 |

1488

| TGC | CAT | CCG | CCC | TAC | CGC | GCC | GAG | CGC | ATC | ATG | AAG | CGC | CTG | GTC | GCC |
|---|---|---|---|---|---|---|---|---|---|---|---|---|---|---|---|
| Cys | His | Pro | Pro | Tyr<br>500 | Arg | Ala | Glu | Arg | Ile<br>505 | Met | Lys | Arg | Leu | Val<br>510 | Ala |

1536

| AAT | CCG | GCT | TTC | GCC | GTC | GAC | GAT | GCC | GCC | GCG | ATC | CAT | GCC | GAT | ACG |
|---|---|---|---|---|---|---|---|---|---|---|---|---|---|---|---|
| Asn | Pro | Ala<br>515 | Phe | Ala | Val | Asp | Asp<br>520 | Ala | Ala | Ala | Ile | His<br>525 | Ala | Asp | Thr |

1584

| CTG | TCG | CCC | CAT | GTC | GGG | TTG | CTG | CGC | CGG | AGG | CTC | GAG | GCG | CTT | GGA |
|---|---|---|---|---|---|---|---|---|---|---|---|---|---|---|---|
| Leu | Ser | Pro<br>530 | His | Val | Gly | Leu | Leu<br>535 | Arg | Arg | Arg | Leu | Glu<br>540 | Ala | Leu | Gly |

1632

| GCC | CGC | GAC | GAC | TCC | GCG | GCC | GAA | GGG | CTG | AGG | CAG | ATG | CTC | GTC | GCC |
|---|---|---|---|---|---|---|---|---|---|---|---|---|---|---|---|
| Ala | Arg | Asp<br>545 | Asp | Ser | Ala | Ala | Glu<br>550 | Gly | Leu | Arg | Gln | Met<br>555 | Leu | Val | Ala |

1680

| TGG | GAC | GGC | CGC | ATG | GAT | GCG | GCT | TCG | GAG | GTC | GCG | TCT | GCC | TAC | AAT |
|---|---|---|---|---|---|---|---|---|---|---|---|---|---|---|---|
| Trp<br>560 | Asp | Gly | Arg | Met | Asp<br>565 | Ala | Ala | Ser | Glu | Val<br>570 | Ala | Ser | Ala | Tyr | Asn<br>575 |

1728

| GCG | TTC | CGC | AGG | GCG | CTG | ACG | CGG | CTG | GTG | ACG | GAC | CGC | AGC | GGG | CTG |
|---|---|---|---|---|---|---|---|---|---|---|---|---|---|---|---|
| Ala | Phe | Arg | Arg | Ala<br>580 | Leu | Thr | Arg | Leu | Val<br>585 | Thr | Asp | Arg | Ser | Gly<br>590 | Leu |

1776

| GAG | CAG | GCG | ATA | TCG | CAT | CCC | TTC | GCG | GCT | GTC | GCG | CCG | GGC | GTC | TCA |
|---|---|---|---|---|---|---|---|---|---|---|---|---|---|---|---|
| Glu | Gln | Ala | Ile | Ser<br>595 | His | Pro | Phe | Ala | Ala<br>600 | Val | Ala | Pro | Gly | Val<br>605 | Ser |

1824

| | | | | | | | | | | | | | | | | |
|---|---|---|---|---|---|---|---|---|---|---|---|---|---|---|---|---|
| CCG | CAA | GGC | CAG | GTC | TGG | TGG | GCC | GTG | CCG | ACC | CTG | CTG | CGC | GAC | GAC | 1872 |
| Pro | Gln | Gly | Gln | Val | Trp | Trp | Ala | Val | Pro | Thr | Leu | Leu | Arg | Asp | Asp | |
| | | 610 | | | | 615 | | | | | 620 | | | | | |
| GAT | GCC | GGA | ATG | CTG | AAG | GGC | TGG | AGC | TGG | GAC | CAG | GCC | TTG | TCT | GAG | 1920 |
| Asp | Ala | Gly | Met | Leu | Lys | Gly | Trp | Ser | Trp | Asp | Gln | Ala | Leu | Ser | Glu | |
| | 625 | | | | 630 | | | | | 635 | | | | | | |
| GCC | CTC | TCG | GTC | GCG | TCG | CAG | AAC | CTG | ACC | GGG | CGA | AGC | TGG | GGC | GAA | 1968 |
| Ala | Leu | Ser | Val | Ala | Ser | Gln | Asn | Leu | Thr | Gly | Arg | Ser | Trp | Gly | Glu | |
| 640 | | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016 |
| Glu | His | Arg | Pro | Arg | Phe | Thr | His | Pro | Leu | Ala | Thr | Gln | Phe | Pro | Ala | |
| | | | | 660 | | | | | 665 | | | | | 670 | | |
| TGG | GCG | GGG | CTG | CTG | AAT | CCG | GCT | TCC | CGT | CCG | ATC | GGT | GGC | GAT | GGC | 2064 |
| Trp | Ala | Gly | Leu | Leu | Asn | Pro | Ala | Ser | Arg | Pro | Ile | Gly | Gly | Asp | Gly | |
| | | | | 675 | | | | 680 | | | | | 685 | | | |
| GAT | ACC | GTG | CTG | GCG | AAC | GGG | CTC | GTC | CCG | TCA | GCC | GGG | CCG | CAG | GCG | 2112 |
| Asp | Thr | Val | Leu | Ala | Asn | Gly | Leu | Val | Pro | Ser | Ala | Gly | Pro | Gln | Ala | |
| | | 690 | | | | | 695 | | | | | 700 | | | | |
| ACC | TAT | GGT | GCC | CTG | TCG | CGC | TAC | GTC | TTC | GAT | GTC | GGC | AAT | TGG | GAC | 2160 |
| Thr | Tyr | Gly | Ala | Leu | Ser | Arg | Tyr | Val | Phe | Asp | Val | Gly | Asn | Trp | Asp | |
| | 705 | | | | | 710 | | | | | 715 | | | | | |
| AAT | AGC | CGC | TGG | GTC | GTC | TTC | CAC | GGC | GCC | TCC | GGG | CAT | CCG | GCC | AGC | 2208 |
| Asn | Ser | Arg | Trp | Val | Val | Phe | His | Gly | Ala | Ser | Gly | His | Pro | Ala | Ser | |
| 720 | | | | | 725 | | | | | 730 | | | | | 735 | |
| GCC | CAT | TAT | GCC | GAT | CAG | AAT | GCG | CCC | TGG | AGC | GAC | TGT | GCG | ATG | GTG | 2256 |
| Ala | His | Tyr | Ala | Asp | Gln | Asn | Ala | Pro | Trp | Ser | Asp | Cys | Ala | Met | Val | |
| | | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304 |
| Pro | Met | Leu | Tyr | Ser | Trp | Asp | Arg | Ile | Ala | Ala | Glu | Ala | Val | Thr | Ser | |
| | | | 755 | | | | 760 | | | | | 765 | | | | |
| CAG | GAA | CTC | GTC | CCG | GCC | TGA | | | | | | | | | | 2325 |
| Gln | Glu | Leu | Val | Pro | Ala | | | | | | | | | | | |
| | | 770 | | | | | | | | | | | | | | |

( 2 ) INFORMATION FOR SEQ ID NO:11:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | |
|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| - 1 | 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | | 20 | | | | | 25 | | | | | 30 | |
| Arg | Val | Arg | Arg | Asp | Ala | Trp | Gly | Ile | Pro | His | Ile | Lys | Ala | Ser | Gly |
| | | | 35 | | | | | 40 | | | | | 45 | | |
| Glu | Ala | Asp | Ala | Tyr | Arg | Ala | Leu | Gly | Phe | Val | His | Ser | Gln | Asp | Arg |
| | | 50 | | | | | 55 | | | | | 60 | | | |
| Leu | Phe | Gln | Met | Glu | Leu | Thr | Arg | Arg | Lys | Ala | Leu | Gly | Arg | Ala | Ala |
| | 65 | | | | | 70 | | | | | 75 | | | | |
| Glu | Trp | Leu | Gly | Ala | Glu | Ala | Ala | Glu | Ala | Asp | Ile | Leu | Val | Arg | Arg |
| 80 | | | | | 85 | | | | | 90 | | | | | 95 |
| Leu | Gly | Met | Glu | Lys | Val | Cys | Arg | Arg | Asp | Phe | Glu | Ala | Leu | Gly | Val |
| | | | | 100 | | | | | 105 | | | | | 110 | |
| Glu | Ala | Lys | Asp | Met | Leu | Arg | Ala | Tyr | Val | Ala | Gly | Val | Asn | Ala | Phe |
| | | | 115 | | | | | 120 | | | | | 125 | | |
| Leu | Ala | Ser | Gly | Ala | Pro | Leu | Pro | Val | Glu | Tyr | Gly | Leu | Leu | Gly | Ala |
| | | | | 130 | | | | | 135 | | | | | 140 | |

| | | | | | | | | | | | | | | |
|---|---|---|---|---|---|---|---|---|---|---|---|---|---|---|
| Glu | Pro | Glu | Pro | Trp | Glu | Pro | Trp | His | Ser | Ile | Ala | Val | Met | Arg | Arg |
| 145 | | | | 150 | | | | | 155 | | | | | | |
| Leu | Gly | Leu | Leu | Met | Gly | Ser | Val | Trp | Phe | Lys | Leu | Trp | Arg | Met | Leu |
| 160 | | | | | 165 | | | | 170 | | | | | | 175 |
| Ala | Leu | Pro | Val | Val | Gly | Ala | Ala | Asn | Ala | Leu | Lys | Leu | Arg | Tyr | Asp |
| | | | | 180 | | | | | 185 | | | | | | 190 |
| Asp | Gly | Gly | Arg | Asp | Leu | Leu | Cys | Ile | Pro | Pro | Gly | Ala | Glu | Ala | Asp |
| | | | 195 | | | | | 200 | | | | | 205 | | |
| Arg | Leu | Glu | Ala | Asp | Leu | Ala | Thr | Leu | Arg | Pro | Ala | Val | Asp | Ala | Leu |
| | | 210 | | | | | 215 | | | | | 220 | | | |
| Leu | Lys | Ala | Met | Gly | Gly | Asp | Ala | Ser | Asp | Ala | Ala | Gly | Gly | Gly | Ser |
| | 225 | | | | | 230 | | | | | 235 | | | | |
| Asn | Asn | Trp | Ala | Val | Ala | Pro | Gly | Arg | Thr | Ala | Thr | Gly | Arg | Pro | Ile |
| 240 | | | | | 245 | | | | | 250 | | | | | 255 |
| Leu | Ala | Gly | Asp | Pro | His | Arg | Val | Phe | Glu | Ile | Pro | Gly | Met | Tyr | Tyr |
| | | | | 260 | | | | | 265 | | | | | 270 | |
| Gln | His | His | Leu | Ala | Cys | Asp | Arg | Phe | Asp | Met | Ile | Gly | Leu | Thr | Val |
| | | | 275 | | | | | 280 | | | | | 285 | | |
| Pro | Gly | Val | Pro | Gly | Phe | Pro | His | Phe | Ala | His | Asn | Gly | Lys | Val | Ala |
| | | 290 | | | | | 295 | | | | | 300 | | | |
| Tyr | Cys | Val | Thr | His | Ala | Phe | Met | Asp | Ile | His | Asp | Leu | Tyr | Leu | Glu |
| | 305 | | | | | 310 | | | | | 315 | | | | |
| Gln | Phe | Ala | Gly | Glu | Gly | Arg | Thr | Ala | Arg | Phe | Gly | Asn | Asp | Phe | Glu |
| 320 | | | | | 325 | | | | | 330 | | | | | 335 |
| Pro | Val | Ala | Trp | Ser | Arg | Asp | Arg | Ile | Ala | Val | Arg | Gly | Gly | Ala | Asp |
| | | | | 340 | | | | | 345 | | | | | 350 | |
| Arg | Glu | Phe | Asp | Ile | Val | Glu | Thr | Arg | His | Gly | Pro | Val | Ile | Ala | Gly |
| | | | 355 | | | | | 360 | | | | | 365 | | |
| Asp | Pro | Arg | Asp | Gly | Ala | Ala | Leu | Thr | Leu | Arg | Ser | Val | Gln | Phe | Ala |
| | | 370 | | | | | 375 | | | | | 380 | | | |
| Glu | Thr | Asp | Leu | Ser | Phe | Asp | Cys | Leu | Thr | Arg | Met | Pro | Gly | Ala | Ser |
| | 385 | | | | | 390 | | | | | 395 | | | | |
| Thr | Val | Ala | Gln | Leu | Tyr | Asp | Ala | Thr | Arg | Gly | Trp | Gly | Leu | Ile | Asp |
| 400 | | | | | 405 | | | | | 410 | | | | | 415 |
| His | Asn | Leu | Val | Ala | Gly | Asp | Val | Ala | Gly | Ser | Ile | Gly | His | Leu | Val |
| | | | | 420 | | | | | 425 | | | | | 430 | |
| Arg | Ala | Arg | Val | Pro | Ser | Arg | Pro | Arg | Glu | Asn | Gly | Trp | Leu | Pro | Val |
| | | | 435 | | | | | 440 | | | | | 445 | | |
| Pro | Gly | Trp | Ser | Gly | Glu | His | Glu | Trp | Arg | Gly | Trp | Ile | Pro | His | Glu |
| | | 450 | | | | | 455 | | | | | 460 | | | |
| Ala | Met | Pro | Arg | Val | Ile | Asp | Pro | Pro | Gly | Gly | Ile | Ile | Val | Thr | Ala |
| | 465 | | | | | 470 | | | | | 475 | | | | |
| Asn | Asn | Arg | Val | Val | Ala | Asp | Asp | His | Pro | Asp | Tyr | Leu | Cys | Thr | Asp |
| 480 | | | | | 485 | | | | | 490 | | | | | 495 |
| Cys | His | Pro | Pro | Tyr | Arg | Ala | Glu | Arg | Ile | Met | Lys | Arg | Leu | Val | Ala |
| | | | | 500 | | | | | 505 | | | | | 510 | |
| Asn | Pro | Ala | Phe | Ala | Val | Asp | Asp | Ala | Ala | Ala | Ile | His | Ala | Asp | Thr |
| | | | | 515 | | | | | 520 | | | | | 525 | |
| Leu | Ser | Pro | His | Val | Gly | Leu | Leu | Arg | Arg | Arg | Leu | Glu | Ala | Leu | Gly |
| | | 530 | | | | | 535 | | | | | 540 | | | |
| Ala | Arg | Asp | Asp | Ser | Ala | Ala | Glu | Gly | Leu | Arg | Gln | Met | Leu | Val | Ala |
| | 545 | | | | | 550 | | | | | 555 | | | | |
| Trp | Asp | Gly | Arg | Met | Asp | Ala | Ala | Ser | Glu | Val | Ala | Ser | Ala | Tyr | Asn |
| 560 | | | | | 565 | | | | | 570 | | | | | 575 |

```
Ala Phe Arg Arg Ala Leu Thr Arg Leu Val Thr Asp Arg Ser Gly Leu
            580                 585                 590

Glu Gln Ala Ile Ser His Pro Phe Ala Val Ala Pro Gly Val Ser
            595                 600                 605

Pro Gln Gly Gln Val Trp Trp Ala Val Pro Thr Leu Leu Arg Asp Asp
            610                 615                 620

Asp Ala Gly Met Leu Lys Gly Trp Ser Trp Asp Gln Ala Leu Ser Glu
625                         630                 635

Ala Leu Ser Val Ala Ser Gln Asn Leu Thr Gly Arg Ser Trp Gly Glu
640                 645                 650                 655

Glu His Arg Pro Arg Phe Thr His Pro Leu Ala Thr Gln Phe Pro Ala
                660                 665                 670

Trp Ala Gly Leu Leu Asn Pro Ala Ser Arg Pro Ile Gly Gly Asp Gly
            675                 680                 685

Asp Thr Val Leu Ala Asn Gly Leu Val Pro Ser Ala Gly Pro Gln Ala
            690                 695                 700

Thr Tyr Gly Ala Leu Ser Arg Tyr Val Phe Asp Val Gly Asn Trp Asp
    705                 710                 715

Asn Ser Arg Trp Val Val Phe His Gly Ala Ser Gly His Pro Ala Ser
720                 725                 730                 735

Ala His Tyr Ala Asp Gln Asn Ala Pro Trp Ser Asp Cys Ala Met Val
                740                 745                 750

Pro Met Leu Tyr Ser Trp Asp Arg Ile Ala Ala Glu Ala Val Thr Ser
            755                 760                 765

Gln Glu Leu Val Pro Ala
            770
```

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGTCGCCTAT AGCGTCACGC ATGCCTTCAT G                      31

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

AATTCGGATC CAAGCTTA                                  18

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2

( D ) OTHER INFORMATION: /note="fMet"

( x i ) SEQUENCE DESCRIPTION: SEQ ID NO:14:

Met Thr Met Ala Ala Asn Thr
1               5

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

CGATAAAATG ACTATGGCGG CCAACACC         28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

CGATAAAATG ACTATGGCAG CTAATACG         28

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CATCGCGTCT TCGAAATCCC TGGCTATTAT GCGCAGCAT         39

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GCAGCTCTGA GCGGTACCGG GCCAATA         27

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

ATGCTGCGCA TAATAGCCAG GGATTTCG         28

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CCGGGCATGT ACTATCAGCA TCAT     24

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GCCGGCGGCG GATCCAACAA CTGG     24

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GATGCGCTGC TGAAGGCGAT G     21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGGCTCGAAA TCGTTGCCGA A     21

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CCGGTCGCAG GCTAGCTGAT GCTGCGCATA     30

( 2 ) INFORMATION FOR SEQ ID NO:25:

( i ) SEQUENCE CHARACTERISTICS:
        ( A ) LENGTH: 31 base pairs
        ( B ) TYPE: nucleic acid
        ( C ) STRANDEDNESS: both ( D ) TOPOLOGY: linear ( i i ) MOLECULE TYPE: DNA (genomic)

( x i ) SEQUENCE DESCRIPTION: SEQ ID NO:25:

CGAAATCCCA GGCGTCTATG CGCAGCATCA T  31

( 2 ) INFORMATION FOR SEQ ID NO:26:

( i ) SEQUENCE CHARACTERISTICS:
        ( A ) LENGTH: 33 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:26:

CTAGATGATG CTGCGCATAG ACGCCTGGGA TTT  33

( 2 ) INFORMATION FOR SEQ ID NO:27:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:27:

CGAGATCCCG GGCGAGTATG CGCAGCATCA T  31

( 2 ) INFORMATION FOR SEQ ID NO:28:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

CGAGATCCCA GGCTGGTATG CGCAGCATCA T  31

( 2 ) INFORMATION FOR SEQ ID NO:29:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

CGAGATCCCA GGCAGCTATG CGCAGCATCA T  31

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

CGAGATCCCA GGCAACTATG CGCAGCATCA T  31

( 2 ) INFORMATION FOR SEQ ID NO:31:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

CGAAATCCCA GGCGCGTATG CGCAGCATCA T      31

( 2 ) INFORMATION FOR SEQ ID NO:32:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

CGAGATCCCA GGCATCTATG CGCAGCATCA T      31

( 2 ) INFORMATION FOR SEQ ID NO:33:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:33:

CGAAATCCCA GGCAAGTATG CGCAGCATCA T      31

( 2 ) INFORMATION FOR SEQ ID NO:34:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:34:

CGAAATCCCA GGCCATTATG CGCAGCATCA T      31

( 2 ) INFORMATION FOR SEQ ID NO:35:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

CGAAATCCCA GGCCCGTATG CGCAGCATCA T      31

( 2 ) INFORMATION FOR SEQ ID NO:36:

( i ) SEQUENCE CHARACTERISTICS:
        ( A ) LENGTH: 31 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:36:

CGAAATCCCA GGCCGCTATG CGCAGCATCA T  31

(2) INFORMATION FOR SEQ ID NO:37:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:37:

CGAAATCCCA GGCTGCTATG CGCAGCATCA T  31

(2) INFORMATION FOR SEQ ID NO:38:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:38:

CGAAATCCCA GGCGATTATG CGCAGCATCA T  31

(2) INFORMATION FOR SEQ ID NO:39:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:39:

CGAAATCCCA GGCGGCTATG CGCAGCATCA T  31

(2) INFORMATION FOR SEQ ID NO:40:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:40:

CGAAATCCCA GGCCAGTATG CGCAGCATCA T  31

(2) INFORMATION FOR SEQ ID NO:41:

(i) SEQUENCE CHARACTERISTICS:
(A) LENGTH: 31 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:41:

CGAAATCCCT GGTTTCTATG CGCAGCATCA T 31

(2) INFORMATION FOR SEQ ID NO:42:

(i) SEQUENCE CHARACTERISTICS:
    (A) LENGTH: 24 base pairs
    (B) TYPE: nucleic acid
    (C) STRANDEDNESS: unknown
    (D) TOPOLOGY: linear (ii) MOLECULE TYPE: DNA (genomic)

(xi) SEQUENCE DESCRIPTION: SEQ ID NO:42:

GCTGCGCATA GGTACCGGG ATTT 24

CEPHALOSPORIN C ACYLASE

The invention relates to a new cephalosporin C acylase (hereinafter referred to as "CC acylase"). More particularly, it relates to a new mutant CC acylase produced by protein engineering, a DNA coding therefor, an expression vector containing the said DNA, a microorganism transformed with the said expression vector, and the production of the CC acylase by culturing the said transformant.

The cephalosporin C acylase is a general term for an enzyme, which is, in common, capable of hydrolyzing cephalosporin C to 7-aminocephalosporanic acid (7-ACA). Hitherto, there have been found three enzymes which should be classified as CC acylase, namely Cephalosporin C acylases SE83, N176 and V22, amino acid sequences of which are disclosed in Journal of Fermentation and Bioengineering Vol. 72, 232–243 (1991). In this literature, numbering of the amino acid sequence of CC acylase is begun at the methionine group of the N-terminal portion thereof. However, numbering of the amino acid sequence of CC acylase is begun at the threonine group adjacent to the methionine group of the N-terminal portion thereof in this Specification, because the N-terminal methionine of α-subunit of mature CC acylase obtained by expressing CC acylase gene in prokaryote was usually removed by an enzyme ( e.g. aminopeptidase) to give a mature CC acylase having the threonine group as the N-terminal amino acid thereof. Production of native type CC acylase by recombinant DNA technology is also disclosed in the said literature and it has been found that the expressed CC acylase is intracellularly processed to give an active form composed of α-subunit and β-subunit. However, efficiency of the processing is generally low in $E.$ $coli.$ From the results of extensive studies, the inventors of this invention have succeeded in producing mutant CC acylases which have more desirable properties which are characterized by higher enzymatic potency, higher efficiency of processing and the like.

The new mutant CC acylase of this invention can be characterized by the following.

(1) A mutant CC acylase wherein cysteine at the 305 position of the amino acid sequence of the native CC acylase is replaced with other amino acid such as serine and the like.

(2) A mutant CC acylase wherein methionine at the 269 position of the amino acid sequence of the native CC acylase is replaced with other amino acid such as tyrosine, phenylalanine, leucine and the like.

(3) A mutant CC acylase wherein alanine at the 271 position of the amino acid sequence of the native CC acylase is replaced with other amino acid such as tyrosine and the like.

(4) A mutant CC acylase having two or three point mutations selected from the above (1)–(3).

Alternatively, the mutant CC acylase can be represented by the following formula (SEQ ID NO:1) as its precursor form before processing into α-subunit and β-subunit thereof:

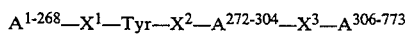

$$A^{1\text{-}268}-X^1-\text{Tyr}-X^2-A^{272\text{-}304}-X^3-A^{306\text{-}773}$$

wherein $A^{1\text{-}268}$ is the same amino acid sequence as that from $\text{Thr}^1$ to $\text{Gly}^{268}$ of native CC acylase, $A^{272\text{-}304}$ is the same amino acid sequence as that from $\text{Gln}^{272}$ to $\text{Tyr}^{304}$ of native CC acylase, $A^{306\text{-}773}$ is the same amino acid sequence as that from $\text{Val}^{306}$ to $\text{Ala}^{773}$ of native CC acylase, $X^1$ is Met or other amino acid, $X^2$ is Ala or other amino acid and $X^3$ is Cys or other amino acid, providing that when $X^1$ is Met and $X^2$ is Ala, $X^3$ is an amino acid other than Cys.

In this specification, a nomenclature for naming a specific mutant CC acylase is conveniently employed. According to this nomenclature, a mutant CC acylase which is prepared by replacing the cysteine residue at position 305 of the amino acid sequence of native CC Acylase with serine should be designated as a mutant CC acylase C305S (SEQ ID NO:3), in which C is the one-letter abbreviation of the cysteine (an amino acid) residue to be replaced, 305 is a position number of the amino acid sequence of native CC acylase and S is the one-letter abbreviation of serine (the other amino acid) used for replacing the cysteine (the former amino acid) residue. On the other hand, for example, mutant CC acylases M269Y (SEQ ID NO:5) or M269T (SEQ ID NO:6) are ones which are prepared by replacing the methionine residue at position 269 of the amino acid sequence of native CC acylase with tyrosine or threonine, respectively. A mutant CC acylase M269Y/C305S (SEQ ID NO:8) is one which is prepared by replacing the methionine residue at position 269 of the amino acid sequence of native CC acylase with tyrosine and the cysteine residue at position 305 of the amino acid sequence of native CC acylase with serine.

The mutant CC acylase of this invention can be prepared by recombinant DNA technology, polypeptide synthesis and the like.

Namely, the new CC acylase can be prepared by culturing a host cell transformed with an expression vector comprising DNA encoding amino acid sequence of the new CC acylase in a nutrient medium and recovering the new CC acylase from the cultured broth.

In this process, particulars of which are explained in more detail as follows.

The host cell may include microorganisms [bacteria (e.g. $Escherichia$ $coli,$ $Bacillus$ $subtilis,$ etc.), yeast (e.g. $Saccharomyces$ $cerevisiae,$ etc.), animal cell lines and cultured plant cells]. Preferred examples of the microorganism may include bacteria, especially a strain belonging to the genus Escherichia (e.g. $E.$ $coli$ JM109 ATCC 53323, $E.$ $coli$ HB101ATCC 33694, $E.$ $coli$ HB101-16 FERN BP-1872, $E.$ $coli$ 294 ATCC 31446, etc.), yeast, especially a strain belonging to the genus Saccharomyces [e.g. $Saccharomyces$ $cerevisiae$ AH22], animal cell lines [e.g. mouse L929 cell, Chinese hamster ovary (CHO) cell etc. ] and the like.

When bacterium, especially $E.$ $coli$ is used as a host cell, the expression vector is usually composed of at least promoter-operator region, initiation codon, DNA encoding amino acid sequence of the new CC acylase, termination codon, terminator region and replicatable unit. When yeasts or animal cells are used as host cells, the expression vector is preferably composed of at least promoter, initiation codon, DNA encoding amino acid sequences of the signal peptide and the new CC acylase, and termination codon. It is possible that enhancer sequence, 5'- and 3'-noncoding region of the new CC acylase, splicing junctions, polyadenylation site and replicatable unit are also inserted into the expression vector.

The promoter-operator region comprises promoter, operator and Shine-Dalgarno (SD) sequence (e.g. AAGG, etc.). Preferable promoter-operator region may include conventionally employed promoter-operator region (e.g. PL-promoter and trp-promoter for *E. coli*) and promoter of the CC acylase N-176 chromosomal gene. The promoter for expression of the new CC acylase in yeast may include the promoter of the TRP1 gene, the ADHI or ADHII gene and acid phosphatase (pH05) gene for *S. cerevisiae* and the promoter for expression of the new CC acylase in mammalian cells may include SV40 early or late-promoter, HTLV-LTR-promoter, mouse metallothionein I(MMT)-promoter, vaccinia-promoter and the like.

Preferable initiation codon may include methionine codon (ATG).

The signal peptide may include a signal peptide of conventionally employed other enzymes (signal peptide of the native t-PA, signal peptide of the native plasminogen) and the like.

The DNA encoding amino acid sequence of the new CC acylase can be prepared in a conventional manner such as a partial or whole DNA synthesis using DNA synthesizer and/or treatment of the complete DNA sequence coding for the native CC acylase inserted in a suitable vector (e.g. pCCN 176-2) obtainable from a transformant [e.g. *E. coli* JM109 (pCCN 176-2) FERM BP-3047] in a suitable manner such as a conventional mutation method [e.g. cassette mutation method (cf. Tokunaga, T. et al., Eur. J. Biochem. 153, 445-449 (1985)), PCR mutation method (cf.Higuchi, R. et al., Nucleic Acids Res. 16, 7351-7367 (1988)), Kunkel's method (cf.Kunkel, T. A. et al., Methods Enzymol. 154, 367 (1987)) and the like] in addition to treatment with a suitable enzyme (e.g. restriction enzyme, alkaline phosphatase, polynucleotide kinase, DNA ligase, DNA polymerase, etc.).

The termination codon(s) may include a conventionally employed termination codon (e.g. TAG, TGA, etc.).

The terminator region may include natural or synthetic terminator (e.g. synthetic fd phage terminator, etc.).

The replicatable unit is a DNA compound having capable of replicating the whole DNA sequence belonging thereto in a host cell and may include natural plasmid, artificially modified plasmid (e.g. DNA fragment prepared from natural plasmid) and synthetic plasmid and preferable examples of the plasmid may include plasmid pBR322 or the artificially modified thereof (DNA fragment obtained from a suitable restriction enzyme treatment of pBR322) for *E. coli*, yeast 2μ plasmid or yeast chromosomal DNA for yeast, plasmid pRSVneo ATCC 37198, plasmid pSV2dhfr ATCC 37145, plasmid pdBPV-MMTneo ATCC 37224, plasmid pSV2neo ATCC 37149 for mammalian cells.

The enhancer sequence may include the enhancer sequence (72 b.p. ) of SV40.

The polyadenylation site may include the polyadenylation site of SV40.

The splicing junction may include the splicing junction of SV40.

The promoter, initiation codon, DNA encoding amino acid sequence of the new CC acylase, termination codon(s) and terminator region can consecutively and circularly be linked with an adequate replicatable unit (plasmid) together, if desired, using an adequate DNA fragment(s) (e.g. linker, other restriction site, etc.) in a conventional manner (e.g. digestion with restriction enzyme, ligation using T4 DNA ligase) to give an expression vector.

A host cell can be transformed (transfected) with the expression vector. Transformation (transfection) can be carried out in a conventional manner [e.g. Kushner method for *E. coli*, calcium phosphate method for mammalian cells, microinjection, etc.] to give a transformant (transfectant).

For the production of the new CC acylase in the process of this invention, thus obtained transformant comprising the expression vector is cultured in an aqueous nutrient medium.

The nutrient medium may contain carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extract, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin $B_1$), antibiotics (e.g. ampicillin, kanamycin), etc.] may be added to the medium. For the culture of mammalian cells, Dulbecco's Modified Eagle's Minimum Essential Medium (DMEM) supplemented with fetal calf serum and an antibiotic is often used.

The culture of the transformant (including transfectant) may usually be carried out at pH 5.5-8.5 (preferably pH 7-7.5) and 18-40° C. (preferably 20-30° C.) for 5-50 hours.

When thus produced new CC acylase exists in the culture solution, culture filtrate (supernatant) is obtained by filtration or centrifugation of the cultured broth. From the culture filtrate, the new CC acylase can be purified in a conventional manner as generally employed for the purification and isolation of natural or synthetic proteins (e.g. dialysis, gel filtration, affinity column chromatography using anti-CC acylase monoclonal antibody, column chromatography on a suitable adsorbent, high performance liquid chromatography, etc.). When the produced new CC acylase exists in periplasm and cytoplasm of the cultured transformant, the cells are collected by filtration and centrifugation, and the cell wall and/or cell membrane thereof are destroyed by, for example, treatment with super sonic waves and/or lysozyme to give debris. The debris can be dissolved in a suitable aqueous solution (e.g. 8M aqueous urea, 6M aqueous guanidium salts). From the solution, the new CC acylase can be purified in a conventional manner as exemplified above.

This invention further provides a process for the preparation of a compound of the formula:

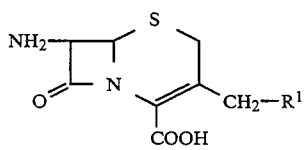 (I)

wherein $R^1$ is acetoxy, hydroxy and hydrogen or its salt, which comprises contacting a compound of the formula:

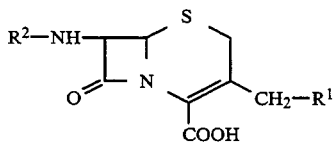

(II)

wherein $R^1$ is the same as defined above and $R^2$ is carboxylic acyl, or its salt, with the cultured broth of a microorganism transformed with an expression vector comprising DNA encoding the new CC acylase of this invention or its processed material.

The carboxylic acyl for $R^2$ may include aliphatic, aromatic or heterocyclic carboxylic acyl and suitable example thereof may be C1-C6 alkanoyl which may have one or two suitable substituent(s) selected from the group of amino, carboxy, C1-C6 alkanoylamino, benzamido or thienyl and the like.

Suitable salt of the compounds (I) and (II) may be alkali metal salt (e.g. sodium salt, potassium salt, lithium salt).

If the CC acylase activity usually exists in transformed cells, the following preparations can be exemplified as a processed material of the cultured broth.

(1) Raw cells, separated from the cultured broth in conventional manners such as filtration and centrifugation (2) dried cells; obtained by drying said raw cells in conventional manners such as lyophilization and vacuum drying (3) cell-free extract; obtained by destroying said raw or dried cells in conventional manners (e.g. autolysis of the cells using an organic solvent, grinding the cells with alumina, sea sand, etc. or treating the cells with super sonic waves)

(4) enzyme solution; obtained by purification or partial purification of said cell-free extracts in conventional manners (e.g. column chromatography)

(5) immobilized cells or enzyme; prepared by immobilizing said cells or enzyme in conventional manners (e.g. a method using acrylamide, glass bead, ion exchange resin, etc.).

The reaction comprising a contact of the compound (II) with the enzyme can be conducted in an aqueous medium such as water or a buffer solution, that is, it can be usually conducted by dissolving or suspending the cultured broth or its processed material in an aqueous medium such as water or a buffer solution containing the compound (II).

Preferable pH of the reaction mixture, concentration of the compound (II), reaction time and reaction temperature may vary with properties of a cultured broth or its processed material to be used. Generally, the reaction is carried out at pH 6 to 10, preferably pH 7 to 9, at 5° to 40° C., preferably 5° to 37° C. for 0.5 to 50 hours.

The concentration of the compound (II) as a substrate in the reaction mixture may be preferably selected from a range of 1 to 100 mg/ml.

Thus produced compound (I) can be purified and isolated from the reaction mixture in a conventional manner.

Brief explanation of the accompanying drawings is as follows.

FIGS. 1A-I show nucleotide sequence (SEQ ID NO:2) and deduced amino acid sequence (SEQ ID NO:3) of DNA encoding a precursor of a mutant CC acylase C305S in plasmids pYSC305S and pCK305.

FIGS. 2A-K show nucleotide sequence (SEQ ID NO:9) and deduced amino acid sequence (SEQ ID NO:3) of DNA encoding a precursor of a mutant CC acylase C305S in plasmid pCK305B.

FIGS. 3A-K show nucleotide sequence (SEQ ID NO:4) and deduced amino acid sequence (SEQ ID NO:5) of DNA encoding a precursor of a mutant CC acylase M269Y in plasmid pCK269Y.

FIGS. 4A-K show nucleotide sequence (SEQ ID NO:10) and deduced amino acid sequence (SEQ ID NO:11) of DNA encoding a precursor of a mutant CC acylase A271Y in plasmids pYSA271Y and pCK271Y.

FIGS. 5A-K show nucleotide sequence (SEQ ID NO:7) and deduced amino acid sequence (SEQ ID NO:8) of DNA encoding a precursor of a mutant CC acylase M269Y/C305S) in plasmid p269Y305S.

FIG. 6 shows a restriction map of the plasmid p269Y305S.

In the following Examples, some plasmids, enzymes, such as restriction enzymes, T4 DNA ligases, and other materials were obtained from commercial sources and used according to the indication by suppliers. Operations employed for the cloning of DNA, transformation of host cells, cultivation of transformants, recovery of the new CC acylase from the cultured broth, and the like are well known in the art or can be adapted from literatures.

Following examples are given for the purpose of illustrating this invention, but not limited thereto.

EXAMPLE 1

(Synthesis of oligodeoxyribonucleotide SN-6)

A DNA oligomer SN-6(5' GGTCGCCTATAGCGTCACGCATGCCTT-CATG 3') was synthesized with 381A DNA synthesizer (Applied Biosystems Inc.). The DNA was liberated from CPG polymer support (CPG: controlled pore glass) with 28% aqueous ammonia followed by heating at 60° C. for 9 hours to remove all protection groups. The reaction mixture was evaporated in vacuo, and the residue was dissolved in 200 μl of TE buffer [10 mM Tris.HCl (pH 7.4)-1 mM EDTA]. The resulting crude DNA solution was applied to reverse phase HPLC [column; COSMOSIL C18 4.6 mm×150 mm (nacalai tesque), eluate; A: 0.1M Triethylammonium acetate buffer (pH 7.2-7.4), B: acetonitrile, gradient; initial A(100%), final A(60%)+B(40%), linear gradient during 25 min, flow rate; 1.2 ml/min]. The eluate containing the objective DNA oligomer was collected and evaporated in vacuo. The purified DNA was dissolved in 200 μl of TE buffer and stored at −20° C. before use.

All other DNA oligomers listed in the following Tables I, If, III and VI were synthesized and purified in a similar manner as described above.

TABLE I

Synthetic DNA oligomers for cassette mutation of N-terminal of CC acylase N176

| restriction sites of each end | sequence of synthetic DNA oligomers<br>upper strand: 5'→3'<br>lower strand: 3'→5' | name/length |
| --- | --- | --- |
| EcoRI/MluI | AATTCGGATCCAAGCTTA<br>GCCTAGGTTCGAATGCGC | 007a/18 (SEQ ID NO:13)<br>007b/18 |
| ClaI/Sau3AI | f Met Thr Met Ala Ala Asn Thr (SEQ ID NO:14)<br>CGATAAAATGACTATGGCGGCCAACACC<br>TATTTTACTGATACCGCCGGTTGTGGCTAG | 002a/28 (SEQ ID NO:15)<br>002b/30 |
| ClaI/BamHI | f Met Thr Met Ala Ala Asn Thr<br>CGATAAAATGACTATGGCAGCTAATACG<br>TATTTTACTGATACCGTCGATTATGCCTAG | 013a/28 (SEQ ID NO:16)<br>013b/30 |

TABLE II

Synthetic DNA oligomers for PCR mutation

| name/length | sequence of synthetic DNA oligomer |
| --- | --- |
| SN-57/39 (SEQ ID NO:17) | 5'-CATCGCGTCTTCGAAATCCCTGGCTATTATGCGCAGCAT-3' |
| SN-42/27 (SEQ ID NO:18) | 3'-GCAGCTCTGAGCGGTACCGGGCCAATA-5' |

TABLE III

Synthetic DNA oligomers for Kunkel's mutation

| name/length | synthetic DNA oligomer sequence (5'→3') |
| --- | --- |
| Z61/28 (SEQ ID NO:19) | ATGCTGCGCATAATAGCCAGGGATTTCG |
| SN-16/24 (SEQ ID NO:20) | CCGGGCATGTACTATCAGCATCAT |
| SN-21/24 (SEQ ID NO:21) | GCCGGCGGCGGATCCAACAACTGG |

TABLE IV

Synthetic DNA oligomers for PCR sequence

| name/length | synthetic oligomer sequence (5'→3') |
| --- | --- |
| SN63/21 (SEQ ID NO:22) | GATGCGCTGCTGAAGGCGATG |
| SN64/21 (SEQ ID NO:23) | GGGCTCGAAATCGTTGCCGAA |

EXAMPLE 2

(Preparation of expression vector for native CC acylase N176 under the control of trp promoter)

(1) Construction of pCC002A, an ampicillin resistant expression vectors for native CC acylase N176:

i) Construction of pCC001A: Plasmid pCCN176-3 [preparation method of this plasmid from plasmid pCCN176-2 (which is obtainable from a transformant *Escherichia coli* JM109 (pCCN176-2) FERM BP-3047 in a conventional manner) is disclosed in page 235 of JOURNAL OF FERMENTATION AND BIOENGINEERING Vol. 72, 1991](1.0 μg) was digested with EcoRI and HindIII, and the 2.9 kb fragment carrying the entire coding region of CC acylase N176 was isolated by agarose gel electrophoresis. On the other hand, pTQiPAΔtrp 1.0 μg), an expression vector for a mutant t-PA [which is obtainable from a transformant, *Escherichia coli* HB101-16 (pTQiPAΔtrp) FERM BP-1870 in a connventional manner and a preparation method of which is disclosed in European Patent Application Publication No. 302456] was digested with EcoRI and HindIII. The resulting 4.3 kb DNA carrying trp promoter, a part of t-PA coding region (Cys92 to Trp113) and the duplicated sequence of fd phage central terminator was isolated. The 2.9 kb and 4.3 kb DNA fragments were mixed to ligate in the presence of T4 DNA ligase (300 units, Takara Shuzo) at 16° C. for 5 hours in 40 μl of a ligation buffer consisting of 50 mM Tris.HCl, 10 mM MgCl₂, 10 mM dithiothreitol and 1 mM ATP. The ligation mixture was used to transform *E. coli* JM109. The desired plasmid, designated as pCC001A, was obtained from one of the transformants resistant to ampicillin and characterized by restriction mapping.

ii) Construction of pCC002A: Plasmid pCC001A contains a portion of t-PA (Cys92 to Trp113) gene between trp promoter and the acylase gene. In order to remove this region, pCC001A (1.0 μg) was digested with ClaI and MluI and the resulting 6.1 kb DNA fragment was isolated. On the other hand, pCCN176-3 (1 μg) was digested with MluI and Sau3AI to isolate 189bp DNA coding for Asp7 to Arg71 of the acylase. Synthetic DNA oligomers 002a and 002b (0.5 n mole, respectively, Table I) were phosphorylated with T4 polynucleotide kinase (1.5 units, Takara Shuzo) in 10 μl of a buffer (kination buffer; 50 mM Tris.HCl, 10 mM MgCl₂, 10 mM DTT, 1.0 mM ATP) at 37° C. for 1 hour and the reaction mixture was heated at 55° C. for 20 min to inactivate the enzyme. The resulting mixture was combined to ligate with the 189 bp Sau3AI/MluI DNA in the presence of T4 DNA ligase at 15° C. for 3 hours in 20 μl of a ligation buffer. To the resultant ligation mixture, the 6.1 kb ClaI/MluI DNA fragment was added and the mixture was incubated at 4° C. for 16 hours in the presence of additional T4 DNA ligase (300 units). The resultant ligation mixture was used to transform *E. coli* JM109. From one of the transformants, the desired plasmid pCC002A that is an expression vector for CC acylase N176, was isolated and characterized by restriction mapping.

(2) Construction of pCK002, a kanamycin resistant expression vector for CC acylase N176:

Plasmid pCC002A was digested with DraI (TOYOBO). The resultant mixture was treated with phenol to remove the enzyme and precipitated by EtOH. The recovered DNA was suspended in 20 μl of a ligation buffer and mixed with phosphorylated EcoRI linker (2 μg, Pharmacia) followed by incubation with T4 DNA ligase (300 units) at 4° C. for 16 hours. The reaction mixture was extracted with phenol and precipitated by EtOH. The recovered DNA was digested with EcoRI and the resultant 5.6 kb DNA lacking ampicillin resistant gene was isolated by agarose gel electrophoresis. On the other hand, plasmid pAO97 [which is obtainable from a transformant *Escherichia coli* JM109(pAO97) FERM BP-3772] (1 μg) was digested with EcoRI, and the resulting 1.2 kb DNA of kanamycin resistance gene was isolated. The 1.2 kb EcoRI DNA was ligated to the 5.6 kb EcoRI DNA with T4 DNA ligase (300 units) in 50 μl of a ligation buffer at 16° C. for 2 hours. The ligation mixture was used to transform *E. coli* JM109 to obtain the desired plasmid pCK002 carrying kanamycin resistant gene for antibiotic marker.

EXAMPLE 3

(Construction of pCK013, a high expression vector for CC acylase N176):

(1) Construction of pCC013A:

i) Construction of pCC007A: Plasmid pCC001A was digested with EcoRI and MluI and the resulting 6.4 kb DNA fragment was isolated by agarose gel electrophoresis. The recovered DNA was ligated to synthetic DNA oligomers 007a and 007b 0.5 μg respectively, Table I), each of which were phosphorylated prior to the ligation reaction, with T4 DNA ligase (300 units) at 16° C. for 5 hours. The resultant mixture was use to transform *E. coli* JM109 to obtain the desired plasmid pCC007A.

ii) Construction of pCCNt013: Plasmid pCC007A (1.0 μg) was digested with ClaI and BamHI and the resultant 6.1 kb DNA was isolated by 5% polyacrylamide gel electrophoresis. The DNA was ligated to synthetic oligomers 013a and 013b (0.5 μg, respectively, each of which were phosphorylated, Table I) with T4 DNA ligase (300 units). The ligation mixture was used to transform *E. coli* JM109 and the desired plasmid pCCNt013 was isolated from ampicillin resistant transformants.

iii) Construction of pCC013A: Plasmid pCCNt013 was digested with BamHI and MluI and the resultant 6.1 kb DNA was isolated. On the other hand, pCC002A (1.0 μg) was digested with MluI and Sau3AI to obtain 189 bp DNA fragment. The resultant DNA was ligated to the 6.1 kb BamHI/MluI DNA fragment with T4 DNA ligase (300 units) and the ligation mixture was used to transform *E. coli* JM109. From one of the transformants resistant to ampicillin, the desired plasmid pCC013A that has AT-rich NH₂ terminal DNA sequence (coding for the same amino acid sequence as that of native CC acylase N176) was isolated.

(2) Construction of pCK013, a kanamycin resistant expression vector for native CC acylase N176:

i) Construction of pΔN176: Plasmid pCK002 (1.0 μg) was digested with AatII (TOYOBO) and the resultant DNA was treated with T4 DNA ligase (150 units) for self-ligation. The ligation mixture was used to transform *E. coli* JM109 to obtain the desired plasmid pΔN176 carrying a unique AatII restriction endonuclease site.

ii) Construction of pCK013: Plasmid pΔN176 (1.0 μg) was digested with AatII and the linearized DNA was treated with bacterial alkaline phosphatase (1 unit, Takara Shuzo) in 100 mM Tris.HCl (pH 8.0) buffer 42° C. for 1 hour. The dephosphorylated DNA was isolated and ligated to the 2.5 kb AatII DNA from pCC013A with T4 DNA ligase. The ligation mixture was used to transform *E. coli* JM109 to obtain the desired plasmid pCK013 carrying kanamycin resistant gene for marker.

EXAMPLE 4

(Point mutation of DNA coding for CC acylase N176 by Kunkel's method)

(1) Subcloning of DNA coding for CC acylase N176 to M13 phage:

(i) Preparation of mp18VVR: Plasmid pCC013A was digested with EcoRV and 795 bp DNA coding for Ile92 to Asp315 of CC acylase N176 was isolated. The DNA was ligated to M13mp18 digested with HincII with T4 DNA ligase and the ligation mixture was used to transform *E. coli* JM109. From one of the plaques, the desired RF DNA mp18VVR in which the part of the acylase DNA was inserted in the reverse direction with plus ori of M13, was isolated and characterized by restriction mapping. The phage solution from which RF DNA mp18VVR was prepared was stored at 4° C. before use.

RF DNA mp18p183 was prepared from 1162bp HpaI/Eco47III DNA from pCC013A and 7250 bp M13mp18 digested with Hinc II in a similar manner as described above.

ii) Preparation of single stranded U-mp18VVR-SS(cf. Kunkel, T. A. et al. Methods Enzyml. 154, 367): A single colony of *E. coli* CJ236 (dut-, ung-, F')(Bio-Rad Lab.) was cultured in 2 ml of 2XTY broth containing chloramphenicol (30 μg/ml) at 37° C. for 16 hours. The cells (0.1 ml) were transferred to a fresh 2XTY broth (50 ml) containing 30 μg/ml chloramphenicol and the cultivation was continued at 37° C. When the absorbance at 600 nm reached to 0.3, the phage solution (MOI<0.2) of mp18VVR was added to the culture. The cultivation was continued for additional 5 hours. After centrifugation at 17,000×g at 4° C. for 15 min, the supernatant was centrifuged again. The resultant supernatant (30 ml) was treated with RNase (150 μg/ml, Sigma) at ambient temperature for 30 min followed by addition of 7.5 ml of PEG solution (3.5M NH₄OAc in 20% polyethyleneglycol 8,000). After centrifugation (17,000×g, 15 min, 4° C.), the residue was suspended in 200 μl of a buffer consisting of 300 mM NaCl, 100 mM Tris.HCl (pH 8.0) and 0.1 mM EDTA. The resultant solution was extracted with 200 μl of phenol and 200 μl of phenol/CHCl₃ (1:1), successively, and washed twice with CHCl₃ (200 μl). To the solution, 7.5M NH₄OAc (100 μl) and ethanol (600 μl) were added to precipitate phage DNA. The DNA was collected by centrifugation, washed with 700 μl of ice-cooled 90% ethanol, and dried in vacuo. The purified single stranded U-DNA (U-mp18VVR-SS) was suspended in 20 μl of TE buffer and stored at 4° C. before use.

Other single stranded U-DNA for Kunkel's mutation method were prepared in a similar manner as described above.

(2) Preparation of RF DNA coding for a mutant CC acylase C305S i) Phosphorylation of oligodeoxyribonucleotide: The DNA oligomer SN-6 (1.84 μg, ca 167 pmole) was phosphorylated with T4 polynucleotide kinase (4.5 units, Takara Shuzo) in 30 μl of a ligation buffer consisting of 50 mM Tris.HCl (pH 7.8), 10 mM MgCl₂, 20 mM dithiothreitol (DTT), 1 mM ATP and 50 μg/ml bovine serum albumin (BSA) at 37° C. for 1 hour.

ii) Annealing reaction: The phosphorylated oligomer (1 μl, ca 5.6 pmole) was mixed with template U-mp18VVR-SS (0.10 pmole, ca 250 ng) in 9 μl of a buffer consisting of 10 mM Tris.HCl (pH 8.0), 6 mM MgCl$_2$ and 40 mM NaCl. The mixture was heated at 70° C. for 5 min followed by allowing to cool at 30° C. over 40 min and placed at 0° C.

iii) Synthesis of double stranded DNA in vitro: The resulting annealing solution (10 μl) was mixed with 1 μl of a synthesis buffer [200 mM Tris.HCl(pH8.0)—40 mM MgCl$_2$], 1 μl of 5 mM dNTP (dATP, dCTP, dGTP and dTTP), T4 DNA ligase (300 units, Takara Shuzo) and T4 DNA polymerase (10 units, Pharmacia). The mixture was incubated on ice for 5 min, at 25° C. for 5 min and 37° C. for 90 min, successively. The reaction was stopped by the addition of 90 μl of a buffer consisting of 10 mM Tris.HCl (pH 8.0) and 10 mM EDTA.

iv) Transformation of E. coli JM109: The synthesized DNA solution (3 μl) was added to competent cells (200 μl) of E. coli JM109 which was prepared in a conventional manner (e.g. cf. SAIBO-KOGAKU 2, 616–626) and the cells were incubated on ice for 30 min.

A single colony of E. coli JM109 was cultured in L broth (2 ml) for 16 hours. The cultured broth (0.1 ml) was transferred to a fresh L broth (2 ml) and the resulting broth was cultured for additional 2 hours to obtain indicator cells.

To the transformed cells (200 μl), the indicator cells (200 μl) were added and the resulting cells were mixed with 3 ml of H-Top agar (1% Bactotrypton, 0.8% NaCl, 0.8% Agar) preheated at 55° C. The cell-agar mixture was spread over H plate (1% Bactotrypton, 0.5% NaCl, 1.5% Agar) and the plate was incubated at 37° C. for 16 hours.

v) Characterization of RF DNA from transformant: A single colony of E. coli JM109 was cultured in 2 ml of 2XTY broth (1.6% Bactotrypton, 1% Yeast Extract, 0.5% NaCl) for 16 hours. The cultured broth (0.1 ml) was transferred to a new 2XTY broth (2 ml) and the resulting broth was cultured for additional 2 hours.

A plaque of the plate in step iv) was picked by a bamboo toothpick (15 cm) and the toothpick was immediately transferred to the cultured 2XTY broth. The cultivation was continued for 5–6 hours at 37° C. Cells from 1 ml of the broth were collected by centrifugation at 10,000 rpm for 15 sec at ambient temperature and the supernatant (phage solution that was used for the large scale preparation of RF DNA in the subsequent experiment) was stored at 4° C. before use. The cells were suspended in 100 μl of GTE buffer (50 mM glucose, 25 mM Tris.HCl (pH8.0), 25 mM EDTA), mixed gently with 200 μl of Alkali-SDS solution (0.2N NaOH, 1% SDS) and mixed vigorously with 150 μl of High-salt buffer (3M KOAc, 3M AcOH) by a VoltexTM mixer. The resulting mixture was centrifuged at 10,000 rpm for 5 min at ambient temperature. The supernatant (400 μl) was treated with 300 μl of isopropyl alcohol and centrifuged at 10,000 rpm for 5 min. The upper layer (300 μl) was separated and mixed with 600 μl of ethanol. After centrifugation (10,000 rpm, 5 min), the precipitates were washed with 500 μl of ice cooled 70% ethanol, dried in vacuo and suspended in 50 μl of TE buffer containing 100 μg/ml of RNase (Sigma) to give RF DNA mp18VVRC305S solution. A portion of the RF DNA solution (10 μl) was used for the restriction endonuclease mapping with SphI, because DNA oligomer SN-6 has strategically introduced SphI site in the sequence to check the mutation.

(3) Preparation of RF DNA coding for A mutant CC acylase M269Y:

The mutant RF DNA (named as p183M269Y) was prepared from single strand U-DNA of mp18p183 (as template) and a primer Z61 (SEQ ID NO:15) (ATGCTGCGCATAATAGCCAGGGATTTCG) in a similar manner as described above.

(4) Preparation of RF DNA coding for a mutant CC acylase A271Y:

The mutant RF DNA (named as mp18VVRA271Y) was prepared from mp18VVR and synthetic DNA oligomer SN-16 (SEQ ID NO:20) in a similar manner as described above.

(5) Preparation of RF DNA named as mp18VVR(SN-21(SEQ ID NO:20)):

Mutant RF DNA for BamHI silent mutant at Gly$^{238}$/Ser$^{239}$ was prepared from mp18VVR and synthetic DNA oligomer SN-21 in a similar manner as described above.

EXAMPLE 5

(Construction of expression vector)

(1) Construction of ampicillin resistant type expression vectors:

(i) Construction of pYSC305S:

The obtained RF DNA (10 μg), in the above Example 4, (designated as mp18VVRC305S), was digested with BstBI (5 units, New England Biolabs.) and XhoI (5 units, TOYOBO). The resultant 162 bp DNA fragment was isolated from the digestion mixture by 5% PAGE. On the other hand, pCC013A (10 μg) was digested with XhoI (5 units) and NcoI (5 units, TOYOBO) and the resulting 128 bp DNA fragment was isolated. Furthermore, pCC013A (10 μg) was digested with BstBI (5 units) and NcoI (5 units) and the large DNA was isolated. The 162 bp BStBI/XhoI DNA, the 128 bp XhoI/NcoI DNA and the 6 kb BstBI/NcoI DNA were ligated at 4° C. for 16 hours in 20 μl of a ligation buffer. The ligation mixture was used to transform E. coli JM109. From one of transformants resistant to ampicillin, the desired plasmid, designated as pYSC305S was isolated and characterized by restriction endonuclease digestion.

(ii) Construction of pYSA271Y:

An expression vector(pYSA271Y) for a mutant CC acylase A271Y was prepared from mp18VVRA271Y in a similar manner as described above.

(iii) Construction of pEX21:

An expression vector(pEX21) for BamHI silent mutant for Gly$^{238}$/Ser$^{239}$ was prepared from mp18VVR(SN-21) in a similar manner as described above.

(2) Costruction of kanamycin resistant type expression vectors (i) Construction of pCK305:

Plasmid pYSC305S was digested with MluI and NcoI and the 872 bp DNA was isolated. On the other hand, pCK013 was digested with NcoI and MluI and the large DNA (ca 6.0 kb) was isolated. The resultant DNA was ligated to the 872 bp DNA fragment with T4 DNA ligase to obtain the desired plasmid pCK305 carrying kanamycin resistant gene for marker.

(ii) Construction of pCK271Y:

Plasmid pCK271Y was also prepared from pCK013 and pYSA271Y in a similar manner as described above.

(iii) Construction of pCK305B:

Plasmid pCK305B was prepared from the large DNA of pCK305 digested with BstB1 and MluI and the small DNA of pEX21 digested with BstB1 and MluI.

(iv) Construction of pCK269Y:

p183M269Y was digested with MluI and NcoI. The small DNA fragment (872 bp) was isolated and ligated to the large DNA (5.9 kb) of pCK013 digested with MluI and NcoI in 20 μl of a ligation buffer [50 mM Tris-HCl (pH 7.8), 10 mM $MgCl_2$, 20 mM dithiothreitol, 1 mM ATP, 50 μg/ml BSA]. The ligation mixture was used to transform E. coli JM109. From one of the transformants, the desired plasmid pCK269Y was isolated and characterized by restriction endonuclease digestion.

EXAMPLE 6

(Construction of p269Y305S for M269YC305S Double Mutant Acylase)

(1) Mutation and amplification of BstBI/NcoI DNA of pCK305:

Mutation and amplification were performed with Taq polymerase (TAKARA) in Taq buffer [50 mM KCl, 50 mM Tris-HCl (pH 8.3), 1.5 mM $MgCl_2$, 0.001% (w/v) gelatin] using Zymoreactor AB-180 (ATTO Co. Ltd.). Primers SN-57 (SEQ ID NO:17) (CATCGCGTCTT-CGAAATCCCTGGCTATTATGCGCAGCAT) and SN-42 (SEQ ID NO:18) (ATAACCGGGCCATGG-CGAGTCTCGACG)(125 pmol, respectively) were mixed with pCK305 (0.5 fmol) in Taq buffer(100 μl) containing dNTP (200 μmol, respectively) and Taq polymerase (1.25 U). The liquid surface of the mixture was covered by addition of a few drops of mineral oil. The mixture underwent initial denaturation (98° C. for 2 min), 30 cycles of amplification (98° C. for 2 min, 48° C. for 2 min, 72° C. for 3 min) and final extension (72° C. for 8 min). The aqueous layer of the resultant mixture was washed with $CHCl_3$, extracted with phenol and precipitated with EtOH. After centrifugation, the recovered DNA was digested with BstI and NcoI. The resultant 290 bp DNA was isolated and ligated to the large DNA fragment of pCK305 digested with BstI and NcoI. The ligation mixture was used to transform E. coli JM109. From one of the transformants, the desired plasmid p269Y305S was isolated and characterized by restriction endonuclease digestion.

EXAMPLE 7

(DNA sequence of Mutant Acylases)

(1) Sequence of pYSC305S:

i) Subclonig to M13mp18: pYSC305S was digested with EcoRV and SmaI and the 265 bp DNA coding for Gly268 to Asp315 of the mutant CC acylase C305S was isolated. On the other hand, M13mp18 was digested with SmaI and the linearized DNA was isolated. The resultant DNA was ligated to the 265 bp SmaI/EcoRV DNA with T4 DNA ligase and the ligation mixture was used to transform E. coli JM103. From one of the plaques, the desired single stranded phage DNA mp18C305S(+) that is carrying the part of mutant acylase DNA (from $NH_2$ to COOH) in the clockwise direction with plus ori of M13 phage was obtained.

ii) Subcloning to M13mp19: RF DNA of mp18C305S was prepared from the cells transformed with mp18C305S(+) and was digested with EcoRI and HindIII to obtain 316 bp DNA fragment. On the other hand, M13mp19 was digested with EcoRI and HindIII, and the large DNA (ca 7.2 kb) was isolated. The resultant DNA was ligated to the 316 bp DNA with T4 DNA ligase and the ligation mixture was used to transform E. coli JM103. From one of the plaques, the desired single stranded phage DNA mp19C305S(−) carrying the part of the mutant acylase DNA in the reverse direction to mp18C305S(+).

iii) Sequence reaction: DNA sequence of single stranded phage DNA mp18C305S(+) and mp19C305S(−) were performed with T7 polymerase (Sequenase TM) using model 370A DNA sequencer (Applied Biosystems Inc.). From the determination of nucleotide sequences of both strand, the DNA sequence in pYSC305S was confirmed to be correct as expected one.

The DNA sequence of pYSA271Y was determined in a similar manner as described above, and proved to be correct as expected one.

(3) Nucleotide sequencing of pCK269Y, p269Y305S and pCK305B:

The nucleotide sequences of pCK269Y, p269Y305S and pCK305B were directly determined by Dye Deoxy TM method with 373A DNA sequencer (Applied Biosystems Inc.). DNA oligomers SN63 (SEQ ID NO:22) (GATGCGCTGCTGAAGGCGATG, coding strand: nucleotide No. 671-691) and SN64 (SEQ ID NO:23) (GGGCTCGAAATCGTTGCCGAA, reverse strand: nucleotide No. 998-1018) were used for the primers. The determined sequence were identical with those of expected.

(4) Nucleotide sequencing of pCKM269F, pCKM269L, pCKM269I and pCKM269H

The nucleotide sequences of pCKM269F, pCKM269L, pCKM269I and pCKM269H were determined in a similar manner as described in Example 7-(3).

Each of expression vectors obtained in the above Examples were introduced into E. coli JM109, respectively before cultivation. A single colony of E. coli JM109 carrying an expression vector was cultivated in L broth (5 ml) containing 50 μg/ml ampicillin (or kanamycin) at 37° C. for 16 h. The resultant broth (0.8 ml) was mixed with 80% aqueous glycerol (0.2 ml) and stored at −80° C. before use.

EXAMPLE 8

(Cultivation of recombinant E. coli)

(1) Cultivation of E. coli JM109/pYSC305S:

A glycerol stock of E. coli JM109/pYSC305S which is a transformant prepared by transforming E. coli JM109 with pYSC305S (1 ml) was transferred to 100 ml of L broth (1% Bactotrypton, 0.5% Yeast Extract, 0.5% NaCl, pH 7.4) containing 50 μg/ml ampicillin and the mixture was cultured at 30° C. for 8 hours. The cultured broth (0.2 mi) was added to 20 ml of MS broth (1.2% Bactotrypton, 2.4% Yeast Extract, 1.25% glycerol, 0.11% leucine, 0.11% proline, 0.11% isoleucine, 1.25% $K_2HPO_4$, 0.38% $KH_2PO_4$, 50 μg/ml thiamine.HCl, 2 mM $MgSO_4.7H_2O$, 0.2 mM $CaCl_2.2H_2O$, 0.05 mM $FeSO_4.7H_2O$) containing 50 μg ampicillin and the mixture was cultured at 30° C. for 16 hours. The resultant cultured broth (3.4 ml) was added to 25 ml of 2% M9CA broth (2% casamino acid, 1.52% $Na_2HPO_4.12-H_2O$, 0.3% $KH_2PO_4$, 0.1% $NH_4Cl$, 0.05% NaCl, 2 mM $MgSO_4.7H_2O$, 0.2 mM $CaCl_2.2H_2O$, 50 μg/ml thiamine.HCl, pH 7.2) containing 1% glycerol and 25 μg/ml ampicillin and the mixture was incubated at 20° C. with vigorous shaking (350–400 rpm per min). At 8 hours, 3-indoleacrylic acid was added to the cultured broth to a final concentration of 20 µg/ml and the cultivation was continued for additional 40 hours. Cells from 20 ml of the resultant broth were harvested by centrifugation at 7,000 rpm for 5 min at 4° C., suspended in 20 ml of TE buffer (pH 8.0) and lysed by sonication. The lysate was centrifuged at 15,000 rpm for 20 min at 4° C. to remove any insoluble materials. The resultant supernatant was stored at 4° C. and used for the determination of CC acylase and GL-7ACA acylase activity and for the preparation of purified mutant CC acylase C305S.

All other E. coli carrying ampicillin resistant expression vectors pCC002A, pCC013A, pYSC305S, pY-SA271Y and pEX21 were cultured in a similar manner as described above.

Other E. coli carrying kanamycin resistant expression vectors pCK013, pCK305B, pCK305, pCK269Y, pCK271Y and p269Y305S were cultured in the corresponding broth containing kanamycin instead of ampicillin in a similar manner as described above.

EXAMPLE 9

(Purification and characterization of acylases)

(1) Purification of CC acylase N176:

To the lysate (20 ml) of the E. coli JM109/pCC013A from 20 ml of cultured broth, ammonium sulfate (4.18 g, final conc: 35% saturation) was added and the mixture was stirred at the ambient temperature for 20 min. The resulting mixture was centrifuged (20° C. 15,000 rpm, 20 min) and the supernatant was collected to treat ammonium sulfate (5.56 g, final conc.: 75% saturation). The precipitates were collected by centrifugation (20° C., 15,000 rpm, 20 min) and dissolved in 5 ml of 100 mM Tris.HCl (pH 9.0). The resulting solution was dialyzed 2 times against each of 4 liters of 100 mM Tris.HCl buffer at 4° C. The resulting dialyzate was filtered with Millex-HV TM (0.45 µm,Millipore) and purified by high performance liquid chromatography [column; TSK-gel TM DEAE TOYOPEARL-5PW (TOSOH), eluate; A: 20 mM Tris.HCl (pH 8.0), B: 0.5M NaCl-Tris.HCl (ph 8.0), gradient; initial: A(80%)+B(20%), final (at 30 min): A(50%)+B(50%), flow rate; 1.0 ml/min]. The main peak eluted with approximately 0.16M NaCl was collected and dialyzed against 4 liters of Tris.HCl (pH 9.0) to obtain pure native type recombinant CC acylase N176.

The purified acylase was analyzed by reverse phase HPLC [column; COSMOSIL 4.6 mm×50 mm (nacalai tesques), eluate; A: 0.05% trifluoroacetic acid (TFA), B: 60% acetonitrile in 0.05% TFA, gradient; initial: A(40%)+B(60%), final (at 20 min): A(0%)+B(100%)] and by sodium dodecyl sulfate polyacrylamide gel electrophoresis (SDS-PAGE). The purity of the acylase so obtained was approximately 95% by HPLC and SDS-PAGE.

Other mutant acylases were purified and analyzed in a similar manner as described above.

(2)Determination of specific activity:

i) GL-7ACA acylase activity: To 200 µl of GL-7ACA solution [10 mg/ml in 0.15M Tris.HCl(pH 8.7), pH was readjusted with 1N NaOH to pH 8.7] that was pre-incubated at 37° C. for 10 min, 20 µl of sample acylase was added and the mixture was incubated at 37° C. for 5 min. The reaction was stopped by the addition of 220 µl of 5% acetic acid. After centrifugation (10,000 rpm for 5 min at ambient temperature) of the resulting mixture, the supernatant was used for the assay of 7ACA formation.

HPLC conditions: column; TSKgel ODS-80 TMCTR 4.4 mm×100 (TOSOH) eluate; 5% (W/V) ammonium acetate in 3% (V/V) acetonitrile, flow rate; 1.0 ml/min, injection volume; 10 µl, detector 254 nm.

One unit was defined as the activity capable of synthesizing 1.0µ mole of 71CA from GL-7ACA per minute at 37° C.

ii) CC acylase activity: To 200 µl of CC solution [10 mg/ml sodium salt of cephalosporin C in 0.15M Tris.HCl (pH 8.7), pH was readjusted with 1N NaOH to pH 8.7] that was pre-incubated at 37° C. for 10 min, 20 µl of sample acylase was added and the mixture was incubated at 37° C. for 30 min. The reaction was stopped by the addition of 220 µl of 5% acetic acid. After centrifugation (10,000 rpm for 5 min at ambient temperature) of the resulting mixture, the supernatant was used for the assay of 7ACA formation.

HPLC conditions: column; TSKgel ODS-80 TMCTR 4.4 mm×100 mm (TOSOH) eluate; 20 mM tertrabutylammonium bromide-10% (W/V) acetonitrile, flow rate; 1.0 ml/min, injection volume; 20 µl, detector 254 nm.

One unit was defined as the activity capable of synthesizing 1.0µ mole of 7ACA from sodium salt of Cephalosporin C per minute at 37° C.

Specific activities of mutant acylases were determined according to the procedure mentioned above.

(3)Determination of amino terminal sequence of native and mutant acylase:

i) Isolation of both chains of CC acylase N176: The purified CC acylase N176 was performed to reverse phase HPLC [column; Cosmosil 5C4 (4.6 mm×35 mm, nacalai tesques), eluate; linear gradient from 36 to 60% acetonitrile in 0.05% TFA over 20 min, flow rate; 1.0 ml/min]. Beta and alpha chains of CC acylase N176 were eluted with approximately 48% and 51% acetonitrile concentration, respectively. Each eluate was collected and lyophilized to obtain alpha (beta) chain of the acylase.

ii) Determination of amino terminal sequence: The amino terminal sequence of alpha (beta) chain was determined by a gas-phase sequencer 470A (Applied Biosystems Inc.) and confirmed to be correct as expected one.

EXAMPLE 10

(I) Cultivation of E. coli JM109/p269Y305S

A glycerol stock of E. coli JM109/p269Y305S was added to 100 ml of L broth containing 50 µg/ml of kanamycin and cultured at 30° C. for 8 hours. A portion of the resultant broth (3.75 ml) was added to 25 ml of N-3 broth (ingredients: 5% hydrolyzed soybean, 1% glycerol, 0.608% $Na_2HPO_4$, 0.7% $KH_2PO_4$, 0.7% $K_2HPO_4$, 0.12% $(NH_4)_2SO_4$, 0.02% $NH_4Cl$, 0.0011% $FeSO_4$, 0.096% $MgSO_4$, 0.0025% kanamycin, 0.0011% $CaCl_2$, 0.00028% $MnSO_4.nH_2O$, 0.00028% $AlCl_3.6-H_2O$, 0.00011% $CoCl_2.6H_2O$, 0.000055% $ZnSO_4.7H_2O$, 0.000055% $NaMoO_4.2H_2O$, 0.000028% $CuSO_4.7H_2O$, 0.000014% $H_3BO_4$). The cultivation was carried out at 20–22° C. At 16 hour, glycerol and IAA were added to the broth in a final concentration of 1% and 20 µg/ml, respectively. At 24 h, glycerol was added to the broth in a final concentration of 1% again. At 30 h, when the A600 of the cultured broth was reached to 15.0, the cells were harvested by centrifugation (4° C., 7000 rpm, 10 min) and lysed by sonication. After centrifugation, the supernatant was collected and assayed on its GL-7ACA acylase activity (41.1 units/ml broth).

(II) Purification of a mutant CC acylase M269Y/C305S E. coli JM109/p269Y305S was cultivated in a 5 liter jar fermenter in a similar manner as mentioned above. The cells from 2 liter broth were suspended in 1.5 liter of 20 mM Tris.HCl (pH 8.0) and lysed by Manton-Golin (500 kg/cm, 2, 3 times). After centrifugation (4° C., 7,000 rpm, 30 min), the supernatant was treated with Polymin P (final concentration of 0.01%). The mixture was centrifuged at 7,000 rpm for 30 min and 15,000 rpm for 20 min, successively. The supernatant was filter-sterilized with 0.45 μm MF membrane to give 20.1 g (HPLC analysis) of the crude acylase. The acylase (4.8 g) was purified by QAE-TOYOPEARL 550C column chromatography [conditions: column; 5.0×13 cm (260 ml), initial equilibration; 20 mM Tris.HCl (pH 8.0), elution; 0.5M NaCl-20 mM Tris.HCl (pH 8.0), flow rate; 10 ml/min] to give 3.45 g of purified a mutant CC acylase M269Y/C305S. The specific activity of the purified M269Y/C305S was 2.14 units/mg as CC acylase determined according to the method described in Example 9-(2).

(III) Comparison of expression of native CC acylase and a mutant CC acylase C305S Glycerol stock solution (1 ml) of E. coli HB101/pCK305 (or HB101/pCK013) which had been prepared by transforming E. coli HB101 with the plasmid pCK305 or pCK013 in a conventional manner was transferred to 20 ml of L broth containing 50 μg/ml kanamycin and the mixture was cultured at 30° C. for 8 hours. The cultured broth (0.2 ml) was added to 20 ml of MS broth (ingredients: 1.2% Bactotrypton, 2.4% Yeast Extract, 1.25% glycerol, 0.11% leucine, 0.11% proline, 0.11% isoleucine, 1.25% $K_2HPO_4$, 0.38% $KH_2PO_4$, 50 μg/ml thiamine.HCl, 2 mM $MgSO_4.7H_2O$, 0.2 mM $CaCl_2.2H_2O$, 0.05 mM $FeSO_4.7H_2O$) containing 50 μg kanamycin and the mixture was cultured at 30° C. for 16 hours. The resultant cultured broth (6 ml) was added to 40 ml of 2% M9CA broth (ingredients: 2% casamino acid, 1.52% $Na_2HPO_4.12H_2O$, 0.3% $KH_2PO_4$, 0.1% $NH_4Cl$, 0.05% NaCl, 2 mM $MgSO_4.7H_2O$, 0.2 mM $CaCl_2.2H_2O$, 50 μg/ml thiamine.HCl, pH 7.2) containing 1% glycerol and 25 μg/ml kanamycin and the mixture was incubated at 30° C. with vigorous shaking (350–400 rpm per min). At 6 h, 3-indoleacrylic acid (IAA) was added to the cultured broth in a final concentration of 40 μg/ml and the cultivation was continued additional 40 hours. Cells were harvested by centrifugation at 14,000 rpm for 15 min at 4° C., suspended in 40 ml of TE buffer (pH 8.0) and lysed by sonication. The lysate was centrifuged at 14,000 rpm for 20 min at 4° C. to obtain the supernatant (designated as "soup" fraction). The residues were resuspended in 40 ml of a buffer containing of 100 mM Tris.HCl (pH 8.0), 1 mM EDTA and 8M urea and lysed by sonication. After centrifugation to remove insoluble materials, the supernatant was collected (designated as "ppt" fraction). The "soup" and "ppt" fractions of a mutant CC acylase C305S and a native CC acylase N176 were analyzed by 15% SDS-PAGE. The cellular insoluble precursor protein was greatly decreased by mutation from a native CC acylase to a mutant CC acylase C305S. The results were corresponding to the amounts of mature acylases (native CC acylase or mutant CC acylase C305S) in "soup" assayed by reversed phase HPLC (in the following Table).

| C305S (μg/ml broth) | | native (μg/ml broth) |
|---|---|---|
| #1 | 329 | 104 |
| #2 | 306 | 103 |
| average | 318 | 104 |

EXAMPLE 11

[Preparation of Mutant CC Acylases M269(Met$^{269}$→other amino acid at the position 269) by cassette mutation]

M269 mutants except mutant CC acylases M269Y and M269T were prepared by replacing the DNA between BstBI and NheI in pCKH274Q with synthetic DNA oligomers that encode the corresponding mutated amino acid sequences (cassette mutation method).

1) Preparation of pCKH274Q i) Preparation of mp18p183(H274Q)

Mutant RF DNA mp18p183(H274Q) carrying NheI site on the DNA sequence for His$^{274}$-Ala$^{276}$ was prepared from mp18p183 and synthetic DNA oligomer Z84 (SEQ ID NO:24) (30-mer, 5'-CCGGTCGCAGG-CTAGCTGATGCTGCGCATA) by Kunkel's method as described in Example 4.

ii) Preparation of pCKH274Q pCKH274Q was prepared by replacing the small DNA between MluI and NcoI of pCK013 with the corresponding DNA from mp18p183(H274Q) in a similar manner as described in Example 5-(2)-(iv).

2) Preparation of M269V

Synthetic oligomers SO-M269Vc (SEQ ID NO:25) (5'-CGAAATCCCAGGCGTCTATGCGCAGCAT-CAT) and SO-M269Vr (SEQ ID NO:26) (5'-CTAGATGATGCTGCGCATAGACGCCTG-GGATTT) were phosphorylated with T4 polynucleotide kinase in a similar manner as described in Example 2-(1)-(ii). The resulting oligomers were ligated to the large DNA of pCKH274Q digested with BstBI and NheI to give the desired expression vector pCKM269V.

Other expression vectors for mutant CC acylases M269E, M269L, M269W, M269S, M269N, M269A, M269I, M269K, M269H, M269P, M269R, M269C, M269D, M269G, M269Q and M269F were prepared from pCKH274Q and synthetic oligomers listed in the following table in a similar manner as described above. pCKM269E and pCKM269L for M269E and M269L mutants, respectively, were prepared by insertion of a pair of oligomers SO-M269E (coding strand) and SO-M269L (reverse strand) to the large DNA digested with BstBI and NheI. The vectors were distinguished with (pCKM269E) or without (pCKM269L) SmaI restriction enzyme sites.

| name/length | synthetic oligomer |
|---|---|
| SO-M269E/31 (SEQ ID NO:27) | 5'-CGAGATCCCGGGCGAGTATGCGCAGCATCAT |
| SO-M269L/33 | TCTAGGGTCCGAATATACGCGTCGTAGTAGATC-5' |
| SO-M269Wc/31 (SEQ ID NO:28) | 5'-CGAGATCCCAGGCTGGTATGCGCAGCATCAT |
| SO-M269Wr/33 | TCTAGGGTCCGACCATACGCGTCGTAGTAGATC-5' |

| name/length | synthetic oligomer |
|---|---|
| SO-M269Sc/31 (SEQ ID NO:29) | 5'-CGAGATCCCAGGCAGCTATGCGCAGCATCAT |
| SO-M269Sr/33 | TCTAGGGTCCGTCGATACGCGTCGTAGTAGATC-5 |
| SO-M269Nc/31 (SEQ ID NO:30) | 5'-CGAGATCCCAGGCAACTATGCGCAGCATCAT |
| SO-M269Nr/33 | TCTAGGGTCCGTTGATACGCGTCGTAGTAGATC-5 |
| SO-M269Vc/31 (SEQ ID NO:25) | 5'-CGAAATCCCAGGCGTCTATGCGCAGCATCAT |
| SO-M269Vr/33 (SEQ ID NO:26) | TTTAGGGTCCGCAGATACGCGTCGTAGTAGATC-5 |
| SO-M269Ac/31 (SEQ ID NO:31) | 5'-CGAAATCCCAGGCGCGTATGCGCAGCATCAT |
| SO-M269Ar/33 | TTTAGGGTCCGCGCATACGCGTCGTAGTAGATC-5' |
| SO-M269Ic/31 (SEQ ID NO:32) | 5'-CGAGATCCCAGGCATCTATGCGCAGCATCAT |
| SO-M269Ir/33 | TCTAGGGTCCGTAGATACGCGTCGTAGTAGATC-5 |
| SO-M269Kc/31 (SEQ ID NO:33) | 5'-CGAAATCCCAGGCAAGTATGCGCAGCATCAT |
| SO-M269Kr/33 | TTTAGGGTCCGTTCATACGCGTCGTAGTAGATC-5 |
| SO-M269Hc/31 (SEQ ID NO:34) | 5'-CGAAATCCCAGGCCATTATGCGCAGCATCAT |
| SO-M269Hr/33 | TTTAGGGTCCGGTAATACGCGTCGTAGTAGATC-5 |
| SO-M269Pc/31 (SEQ ID NO:35) | 5'-CGAAATCCCAGGCCCGTATGCGCAGCATCAT |
| SO-M269Pr/33 | TTTAGGGTCCGGGAATACGCGTCGTAGTAGATC-5' |
| SO-M269Rc/31 (SEQ ID NO:36) | 5'-CGAAATCCCAGGCCGCTATGCGCAGCATCAT |
| SO-M269Rr/33 | TTTAGGGTCCGGCGATACGCGTCGTAGTAGATC-5 |
| SO-M269Cc/31 (SEQ ID NO:37) | 5'-CGAAATCCCAGGCTGCTATGCGCAGCATCAT |
| SO-M269Cr/33 | TTTAGGGTCCGACGATACGCGTCGTAGTAGATC-5 |
| SO-M269Dc/31 (SEQ ID NO:38) | 5'-CGAAATCCCAGGCGATTATGCGCAGCATCAT |
| SO-M269Dr/33 | TTTAGGGTCCGCTAATACGCGTCGTAGTAGATC-5 |
| SO-M269Gc/31 (SEQ ID NO:39) | 5'-CGAAATCCCAGGCGGCTATGCGCAGCATCAT |
| SO-M269Gr/33 | TTTAGGGTCCGCCGATACGCGTCGTAGTAGATC-5' |
| SO-M269Qc/31 (SEQ ID NO:40) | 5'-CGAAATCCCAGGCCAGTATGCGCAGCATCAT |
| SO-M269Qr/33 | TTTAGGGTCCGGTCATACGCGTCGTAGTAGATC-5 |
| SO-M269Fc/31 (SEQ ID NO:41) | 5'-CGAAATCCCTGGTTTCTATGCGCAGCATCAT |
| SO-M269Fr/33 | TTTAGGGACCAAAGATACGCGTCGTAGTAGATC-5 |

3) Preparation of pCKM269T pCKM269T was prepared by replacing the small DNA between MluI and NcoI of pCK013 with the corresponding DNA from mp18p183(M269T), constructed from synthetic oligomer Z63 (SEQ ID NO:42) (24 mer, 5'-GCTGCGCATAGGTACCCGGGATTT) and mp18p183 by Kunkel's method, in a similar manner as described in Example 4.

4) Preparation of pCKM269F

Synthetic oligomers SO-M269Fc (5'-CGAAATCCCTGGTTTCTATGCGCAGCATCAT) and SO-M269Fr (5'-CTAGATGATGCTGCGCATAGAAACCAGGGATTT) (SEQ ID NO:41) were phosphorylated with T4 polynucleotide kinase in a similar manner as described in Example 2-(1)-(ii). The resulting oligomers were ligated to the large DNA of pCKH274Q digested with BstBI and NheI to give the desired expression vector pCKM269F.

5) Preparation of pCKM269L

Synthetic oligomers SO-M269E (coding strand, 5'-CGAGATCCCGGGCGAGTATGCGCAGCATCAT) and SO-M269L (reverse strand, 5'-CTAGATGATGCTGCGCATATAAGCCTGGGATCT) (SEQ ID NO:27) were phosphorylated with T4 polynucleotide kinase in a similar manner as described in Example 2-(1)-(ii). The resulting oligomers were ligated to the large DNA of pCKH274Q digested with BstBI and NheI. The ligation mixture was used to transform E. coli JM109. From the resultant transformants, a plasmid with one SmaI site and without BstBI nor NheI sites was confirmed to be the desired plasmid pCKM269L.

(6) Cultivation of E. coli JM109 carrying M269 mutant acylase expression vectors E. coli JM109 was transformed with pCKM269Y (pCKM269F or pCKM269L). A single colony was cultivated in L broth containing 50 μg/ml kanamycin (5 ml) at 37° C. for 16 h. A portion (0.8 ml) of the resultant broth was mixed wish 80% aqueous glycerol (0.2 ml) to give a glycerol stock of E. coli JM109/pCKM269Y. The stock of E. coli JM109/pCKM269Y (pCKM269F or pCKM269L) (1 ml) was cultivated in a similar manner as described in Example 8.

(7) Purification and characterization of M259 mutant acylases

M269Y, M269F and M269L were purified from the corresponding lyzates obtained in step (V) in a similar manner as described in Example 9-(1). The purified M269Y, M269F and M269L were used to determine their specific activities according to the method described in Example 9-(2). The results are listed in the following table.

TABLE

Specific activity of M269 mutants

| acylase | CC acylase activity (% of native) |
|---|---|
| native | 1.55 (100)) |
| M269Y | 2.11 (136) |
| M269F | 2.62 (169) |

| | |
|---|---|
| M269L | 1.67 (108) |

Note: Each value means specific activity (units/mg protein).

TABLE-continued
Specific activity of M269 mutants

We claim:

1. A mutant cephalosporin C acylase derived from a precursor of the formula:

$$A^{1-268}-X^1-Tyr-X^2-A^{272-304}-X^3-A^{306-773}$$

(SEQ ID NO:1), wherein:
 $A^{1-268}$ is the same amino acid sequence as that from $Thr^1$ to $Gly^{268}$ of native CC acylase,
 $A^{272-304}$ is the same amino acid sequence as that from $Gln^{272}$ to $Tyr^{304}$ of native CC acylase,
 $A^{306-773}$ is the same amino acid sequence as that from $Val^{306}$ to $Ala^{773}$ of native CC acylase,
 $X^1$ is Met or other amino acid,
 $X^2$ is Ala or Tyr, and
 $X^3$ is Cys or Ser,
provided that when $X^1$ is Met and $X^2$ is Ala, $X^3$ is Ser; and that said mutant cephalosporin C acylase has a property selected from the group consisting of higher enzymatic potency and higher processing efficiency, as compared to said native CC acylase.

2. The mutant cephalosporin C acylase of claim 1, wherein said property is higher enzymatic potency.

3. The mutant cephalosporin C acylase of claim 1, wherein:
 $X^1$ is selected from the group consisting of Tyr, Phe and Leu,
 $X^2$ is Ala, and
 $X^3$ is Cys or Ser.

4. The mutant cephalosporin C acylase of claim 3, wherein $X^1$ is selected from the group consisting of Tyr and Phe.

5. The mutant cephalosporin C acylase of claim 4, wherein $X^1$ is Tyr and $X^3$ is Ser.

6. The mutant cephalosporin C acylase of claim 1, wherein said precursor of the formula:

$$A^{1-268}-X^1-Tyr-X^2-A^{272-304}-X^3-A^{306-773}$$

(SEQ ID NO:1) has an increase in cellular solubility relative to the precursor of said native CC acylase.

7. The mutant cephalosporin C acylase of claim 6, wherein $X^1$ is Met, $X^2$ is Ala and $X^3$ is Ser.

8. The mutant Cephalosporin C acylase of claim 1, in which $X^1$ is Tyr, $X^2$ is Ala and $X^3$ is Ser. (SEQ ID NO:8).

9. A DNA which encodes cephalosporin C acylase of claim 1.

10. An expression vector which comprises DNA of claim 9.

11. A host cell transformed by expression vector of claim 10.

* * * * *